(12) United States Patent
Lee et al.

(10) Patent No.: US 11,450,821 B2
(45) Date of Patent: Sep. 20, 2022

(54) ORGANIC ELECTROLUMINESCENCE DEVICE AND POLYCYCLIC COMPOUND FOR ORGANIC ELECTROLUMINESCENCE DEVICE

(71) Applicant: Samsung Display Co., LTD., Yongin-si (KR)

(72) Inventors: Yeseul Lee, Busan (KR); Soo-Byung Ko, Yongin-si (KR); Hyeongmin Kim, Suwon-si (KR); HeeChoon Ahn, Seoul (KR); Hyunah Um, Seoul (KR); Yirang Im, Daejeon (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 288 days.

(21) Appl. No.: 16/897,744

(22) Filed: Jun. 10, 2020

(65) Prior Publication Data
US 2021/0066620 A1 Mar. 4, 2021

(30) Foreign Application Priority Data
Sep. 3, 2019 (KR) .................. 10-2019-0108817

(51) Int. Cl.
*H01L 29/08* (2006.01)
*H01L 51/00* (2006.01)
*H01L 51/50* (2006.01)

(52) U.S. Cl.
CPC ...... *H01L 51/0074* (2013.01); *H01L 51/0072* (2013.01); *H01L 51/0073* (2013.01); *H01L 51/0094* (2013.01); *H01L 51/5024* (2013.01)

(58) Field of Classification Search
CPC .......... H01L 51/0074; H01L 51/0073; H01L 51/0072; H01L 51/0094; H01L 51/5024
(Continued)

(56) References Cited

U.S. PATENT DOCUMENTS

2014/0239281 A1\* 8/2014 Ise .................. C07D 495/06
585/27
2017/0018720 A1 1/2017 Adachi et al.
(Continued)

FOREIGN PATENT DOCUMENTS

| CN | 102786508 | 11/2012 |
|---|---|---|
| JP | 5867840 | 2/2016 |

(Continued)

*Primary Examiner* — Phuc T Dang
(74) *Attorney, Agent, or Firm* — Kile Park Reed & Houtteman PLLC

(57) ABSTRACT

An organic electroluminescence device comprises a first electrode, a second electrode disposed on the first electrode, and an emission layer disposed between the first electrode and the second electrode. The emission layer comprises a polycyclic compound represented by Formula 1 and achieves high efficiency and a low driving voltage. In Formula 1, at least one of $Ar_1$ to $Ar_4$ is represented by Formula 2.

[Formula 1]

(Continued)

-continued

[Formula 2]

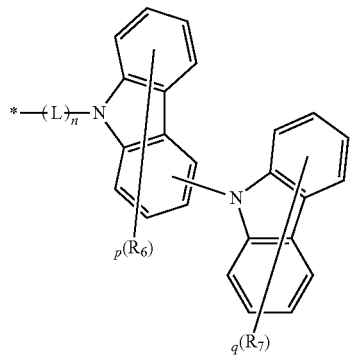

20 Claims, 2 Drawing Sheets

(58) Field of Classification Search
USPC .......................................................... 257/40
See application file for complete search history.

(56) References Cited

U.S. PATENT DOCUMENTS

2017/0179395 A1   6/2017  Kim et al.
2017/0213980 A1*  7/2017  Nakano ............... H01L 51/0058
2019/0097157 A1*  3/2019  Takada ................ H01L 51/0094
2019/0207112 A1*  7/2019  Hatakeyama ....... H01L 51/0061

FOREIGN PATENT DOCUMENTS

KR   10-2017-0075123   7/2017
KR   10-2018-0045696   5/2018

* cited by examiner

ORGANIC ELECTROLUMINESCENCE DEVICE AND POLYCYCLIC COMPOUND FOR ORGANIC ELECTROLUMINESCENCE DEVICE

CROSS-REFERENCE TO RELATED APPLICATION(S)

This application claims priority to and benefits of Korean Patent Application No. 10-2019-0108817 under 35 U.S.C. § 119, filed on Sep. 3, 2019 in the Korean Intellectual Property Office, the entire contents of which are incorporated herein by reference.

BACKGROUND

The disclosure herein relates to an organic electroluminescence device and a polycyclic compound used therein.

The development of an organic electroluminescence device as an image display device is being actively conducted. The organic electroluminescence device is called a self-luminescent display device in which holes and electrons injected from a first electrode and a second electrode, respectively, recombine in an emission layer, and a light-emitting material which is an organic compound included in the emission layer emits light to achieve display.

In the application of an organic electroluminescence device to a display device, improvements to the life of the organic electroluminescence device is required, and development of materials for a stable organic electroluminescence device meeting these requirements is being continuously demanded.

SUMMARY

The disclosure provides an organic electroluminescence device having high efficiency and a low driving voltage, and a polycyclic compound used therein.

A polycyclic compound according to an embodiment may be represented by Formula 1:

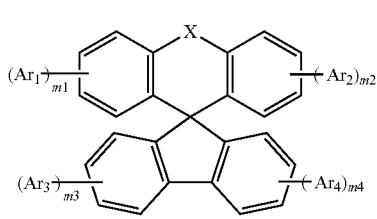

[Formula 1]

In Formula 1, X may be O, S, $CR_1R_2$, $NR_3$, or $SiR_4R_5$. $R_1$ to $R_5$ may be each independently a hydrogen atom, a deuterium atom, a substituted or unsubstituted alkyl group of 1 to 20 carbon atoms, or a substituted or unsubstituted aryl group of 6 to 30 carbon atoms for forming a ring. At least one of $Ar_1$ to $Ar_4$ may be represented by Formula 2 and the remainder may be each independently a hydrogen atom, a deuterium atom, a substituted or unsubstituted alkyl group of 1 to 20 carbon atoms, or a substituted or unsubstituted aryl group of 6 to 30 carbon atoms for forming a ring. In Formula 1, m1 to m4 may be each independently an integer from 0 to 4, where at least one of m1 to m4 may be an integer from 1 to 4.

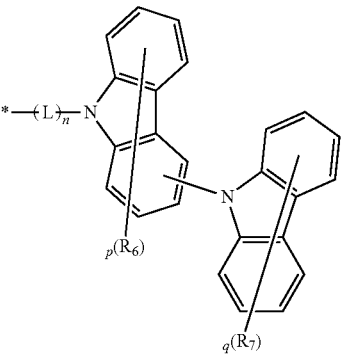

[Formula 2]

In Formula 2, $R_6$ and $R_7$ may be each independently a hydrogen atom, a deuterium atom, a substituted or unsubstituted alkyl group of 1 to 20 carbon atoms, a substituted or unsubstituted silyl group, a substituted or unsubstituted aryl group of 6 to 30 carbon atoms for forming a ring, or a substituted or unsubstituted heteroaryl group of 2 to 30 carbon atoms for forming a ring. In Formula 2, L may be a direct linkage, a substituted or unsubstituted divalent alkyl group of 1 to 20 carbon atoms, a substituted or unsubstituted arylene group of 6 to 30 carbon atoms, or a substituted or unsubstituted heteroarylene group of 2 to 30 carbon atoms. In Formula 2, n may be 0 or 1, p may be an integer from 0 to 7, and q may be an integer from 0 to 8.

In an embodiment, $Ar_1$ to $Ar_4$ may be each independently represented by Formula 2 above.

In an embodiment, Formula 1 may be represented by Formula 1-1 to Formula 1-5:

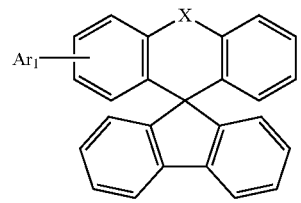

[Formula 1-1]

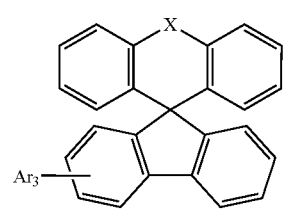

[Formula 1-2]

[Formula 1-3]

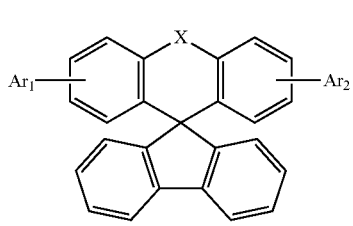

[Formula 1-4]

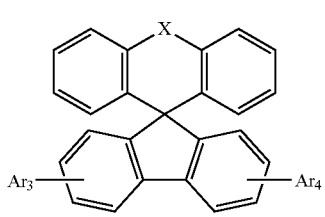

[Formula 1-5]

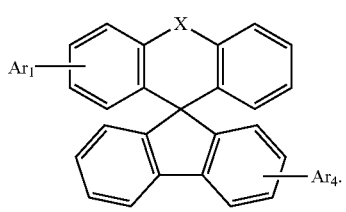

In Formula 1-1 to Formula 1-5, $Ar_1$ to $Ar_4$ may be independently represented by Formula 2 above.

In an embodiment, Formula 2 may be represented by Formula 2-1:

[Formula 2-1]

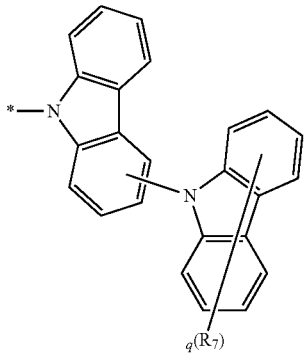

In Formula 2-1, $R_7$ and q may be the same as defined in Formula 2.

In an embodiment, $R_1$ to $R_5$ may be substituted or unsubstituted alkyl groups of 1 to 5 carbon atoms, or substituted or unsubstituted phenyl groups.

In an embodiment, $R_7$ may be a hydrogen atom, a t-butyl group, an aryl silyl group, a substituted or unsubstituted phenyl group, a substituted or unsubstituted naphthyl group, a substituted or unsubstituted dibenzofuran group, or a substituted or unsubstituted dibenzothiophene group.

In an embodiment, a polycyclic compound may be represented by Formula 3:

[Formula 3]

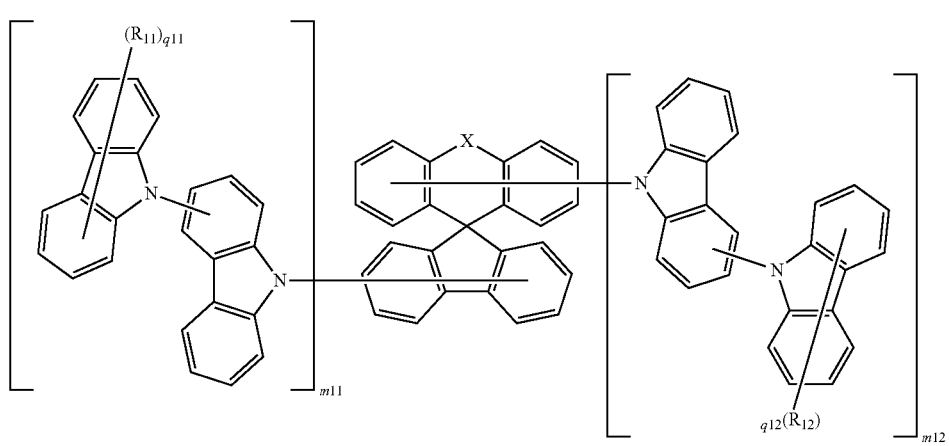

In Formula 3, X may be O, S, $CR_1R_2$, $NR_3$, or $SiR_4R_5$. $R_1$ to $R_5$ may be each independently a hydrogen atom, a deuterium atom, a substituted or unsubstituted alkyl group of 1 to 20 carbon atoms, or a substituted or unsubstituted aryl group of 6 to 30 carbon atoms for forming a ring. $R_{11}$ and $R_{12}$ may be each independently a hydrogen atom, a deuterium atom, a substituted or unsubstituted alkyl group of 1 to 20 carbon atoms, a substituted or unsubstituted silyl group, a substituted or unsubstituted aryl group of 6 to 30 carbon atoms for forming a ring, or a substituted or unsubstituted heteroaryl group of 2 to 30 carbon atoms for forming a ring. In Formula 3, q11 and q12 may be each independently an integer from 0 to 8. In Formula 3, m11 and m12 may be each independently an integer from 0 to 2, where at least one of m11 or m12 may be 1 or 2.

In an embodiment, Formula 3 may be represented by Formula 3-1:

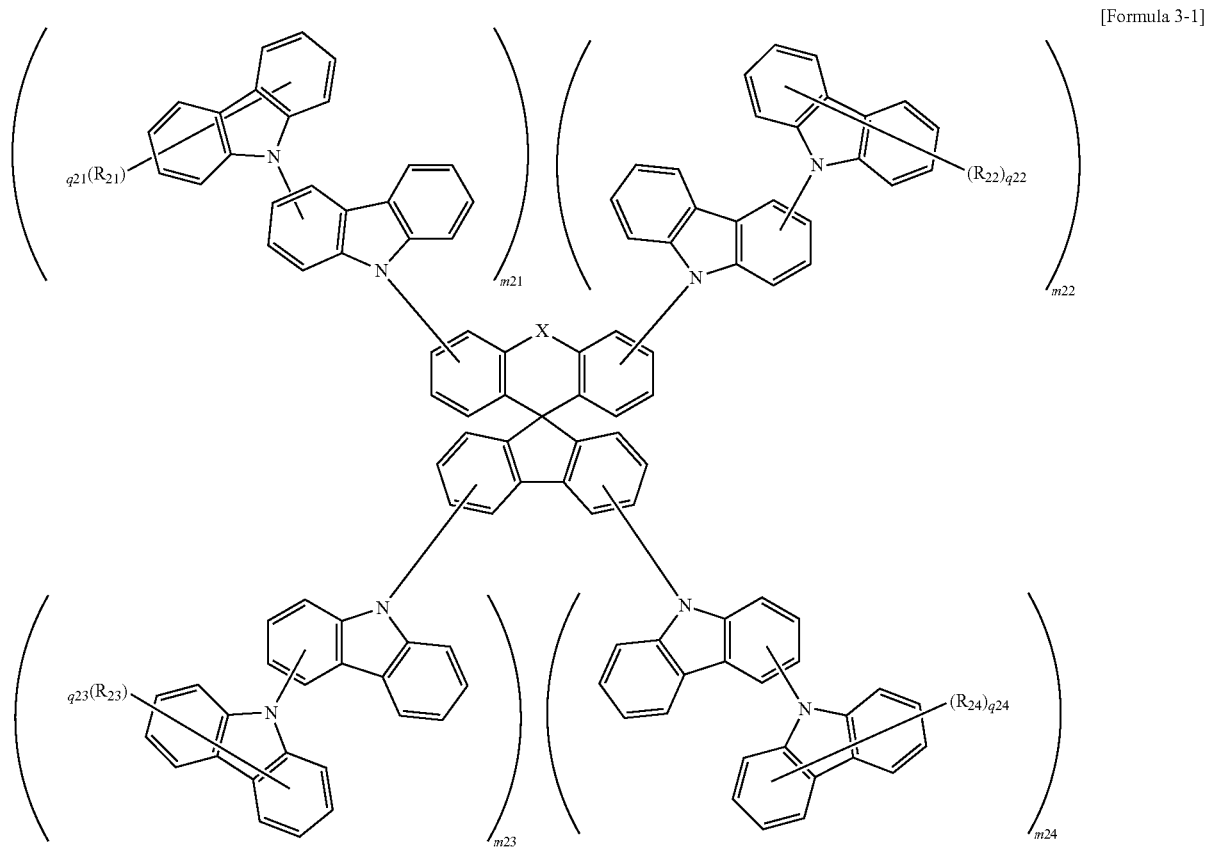

[Formula 3-1]

In Formula 3-1, $R_{21}$ to $R_{24}$ may be each independently a hydrogen atom, a deuterium atom, a substituted or unsubstituted alkyl group of 1 to 20 carbon atoms, a substituted or unsubstituted silyl group, a substituted or unsubstituted aryl group of 6 to 30 carbon atoms for forming a ring, or a substituted or unsubstituted heteroaryl group of 2 to 30 carbon atoms for forming a ring. In Formula 3-1, m21 to m24 may be each independently 0 or 1, where at least one of m21 to m24 may be 1. In Formula 3-1, q21 to q24 may be each independently an integer from 0 to 8. X may be the same as defined in Formula 3.

Formula 1, or Formula 3 may be any one among the compounds represented in the following Compound Group 1:
[Compound Group 1]
1
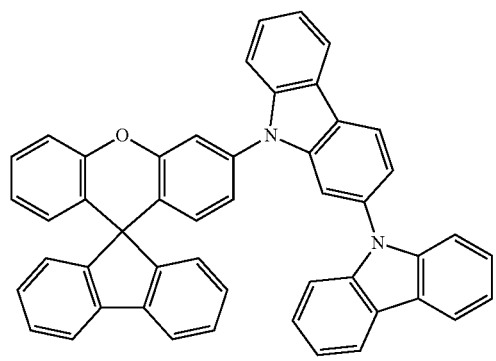
2
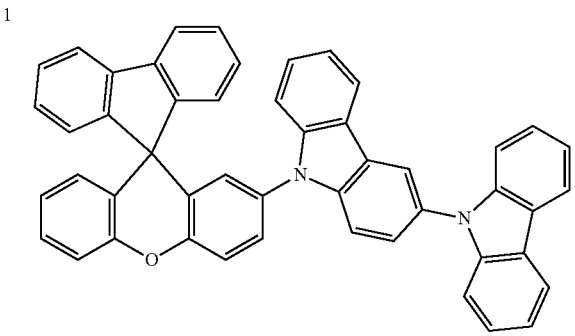
3
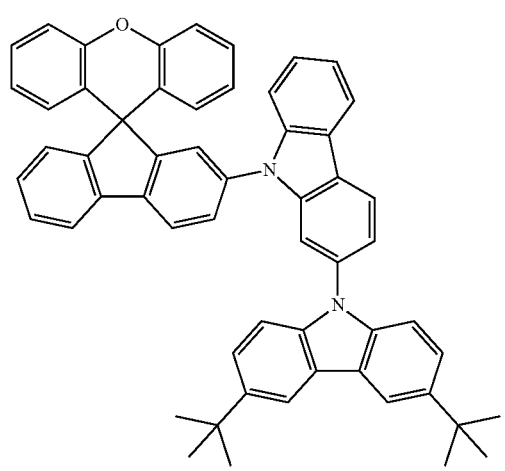
4
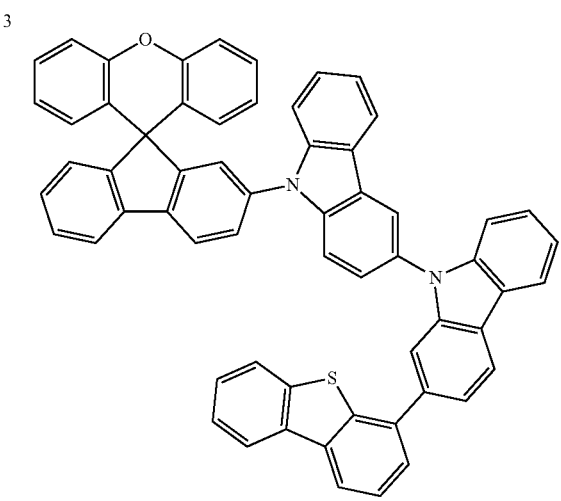
5
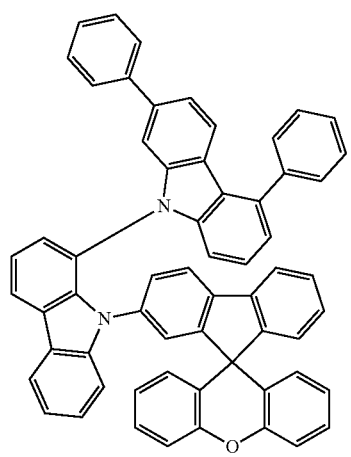
6
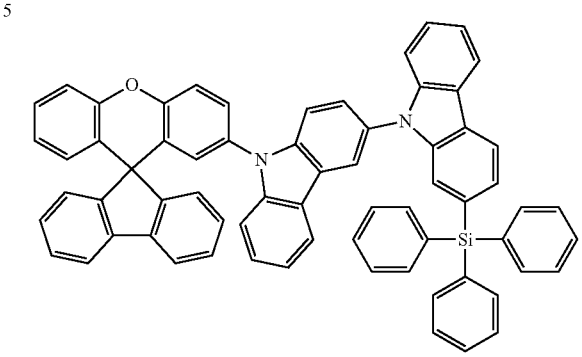

-continued
7
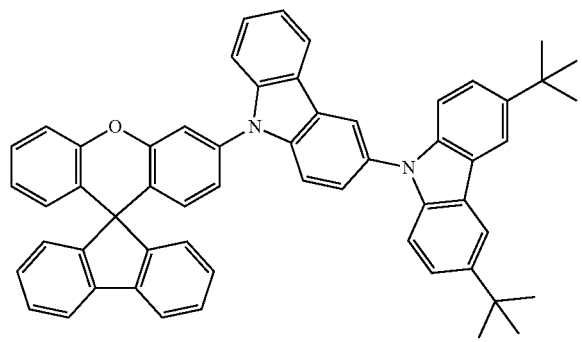
8
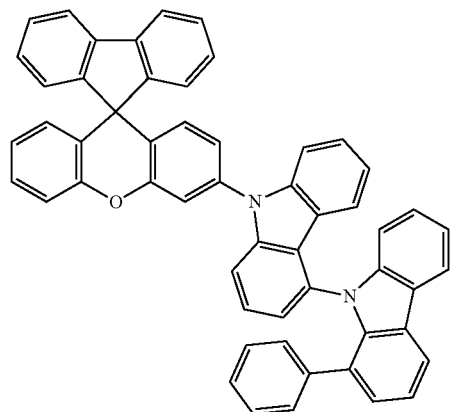
9
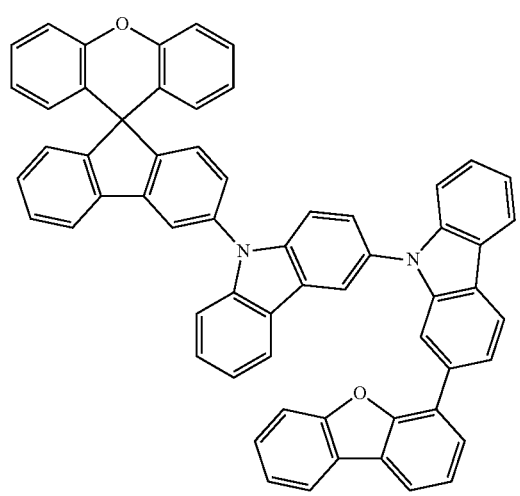
10
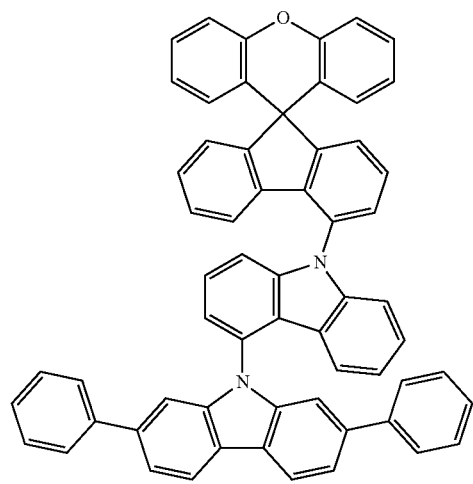
11
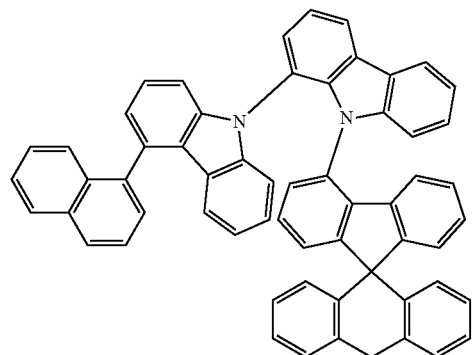
12
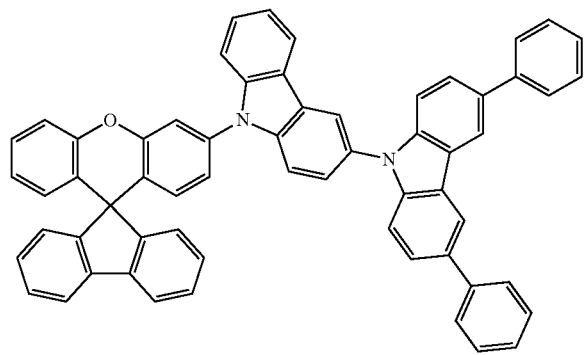

-continued
13
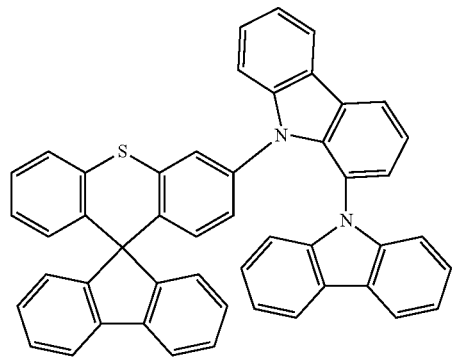
14
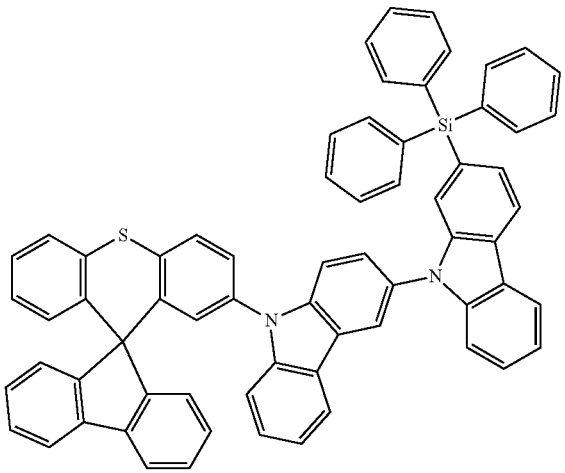
15
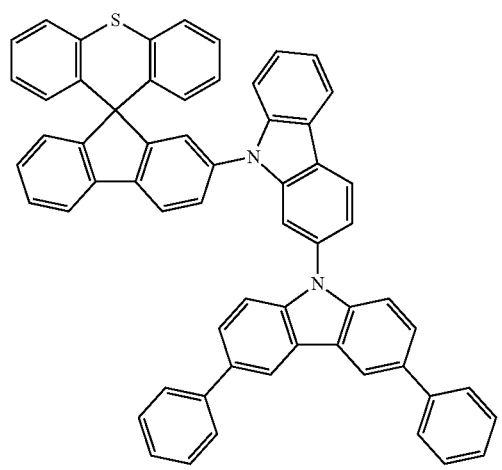
16
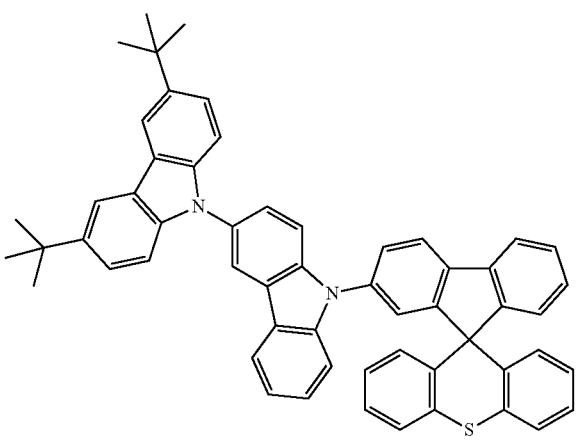
17
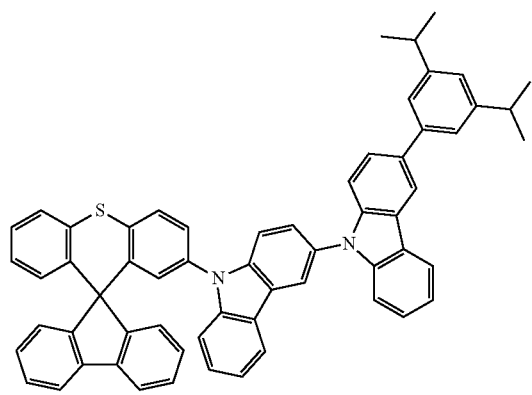
18
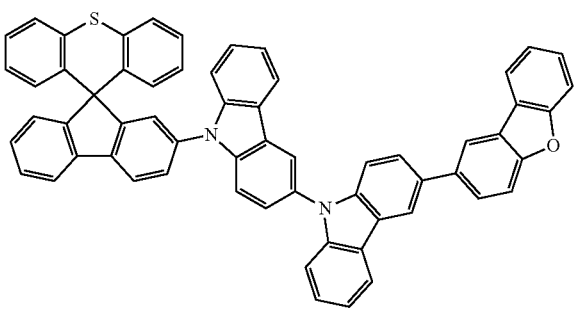

-continued
19
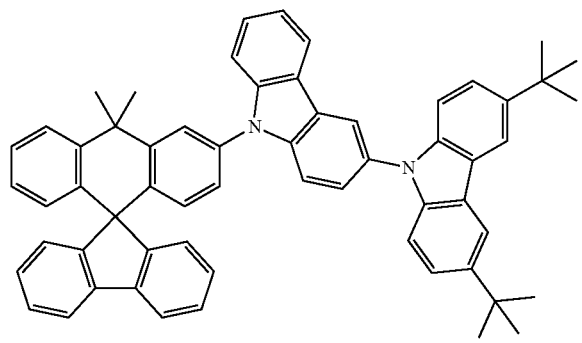
20
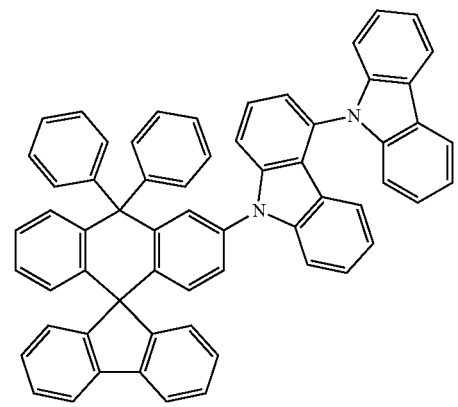
21
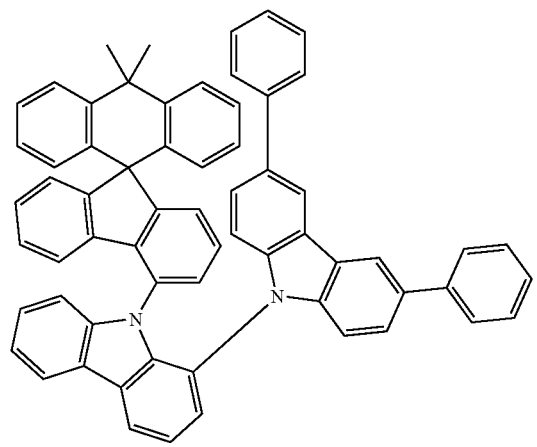
22
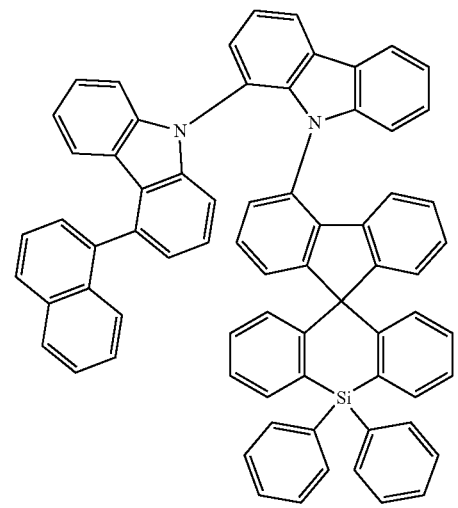
23
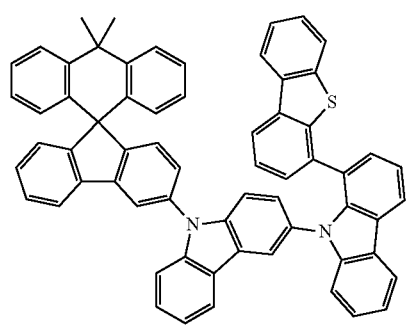
24
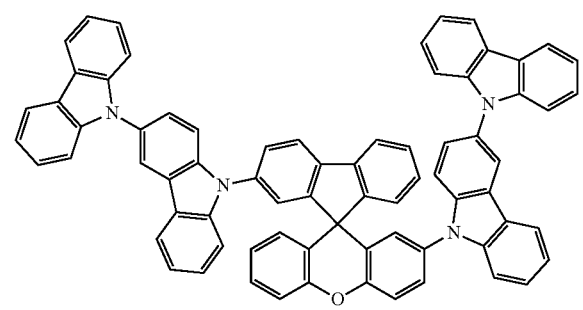
25
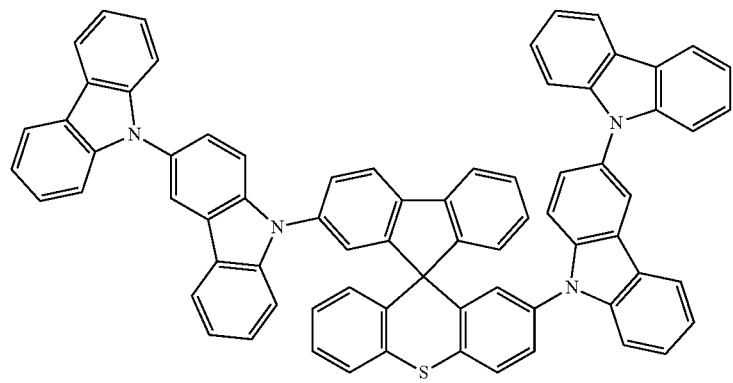

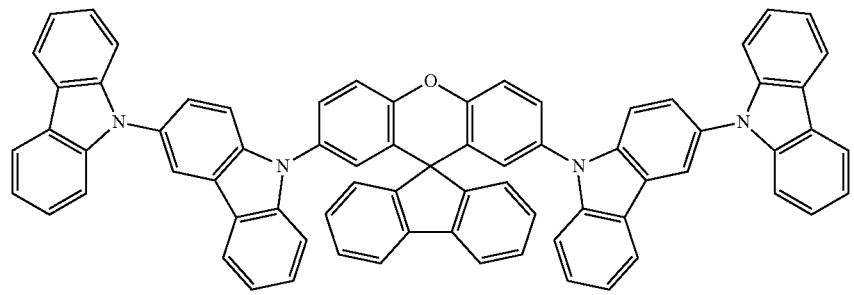
26
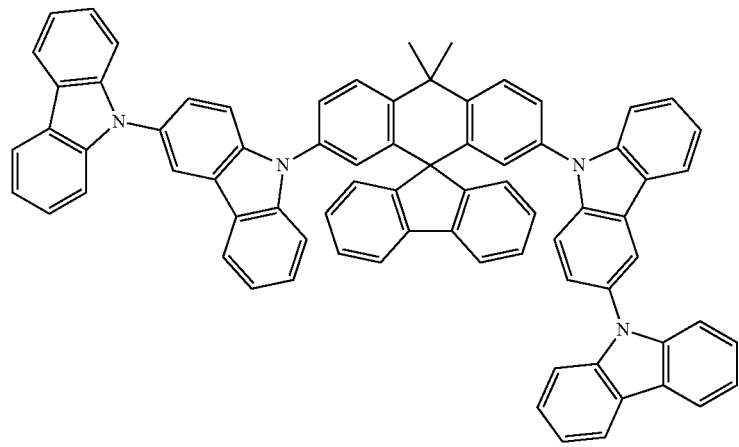
27
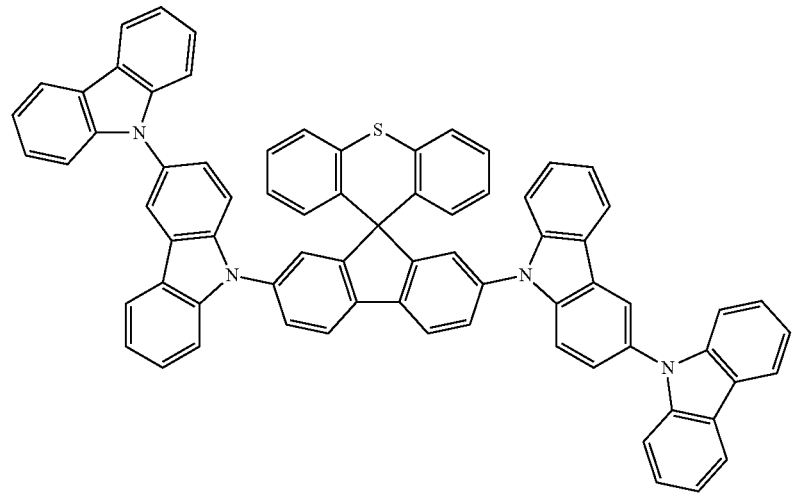
28
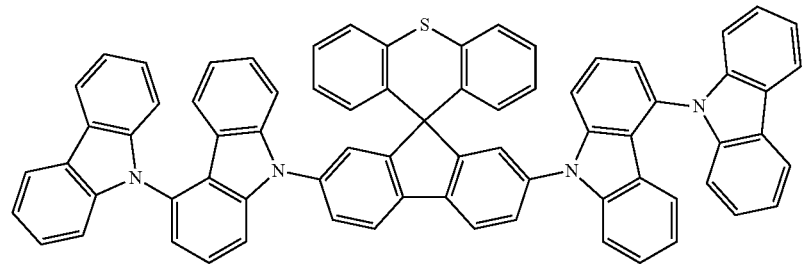
29

30
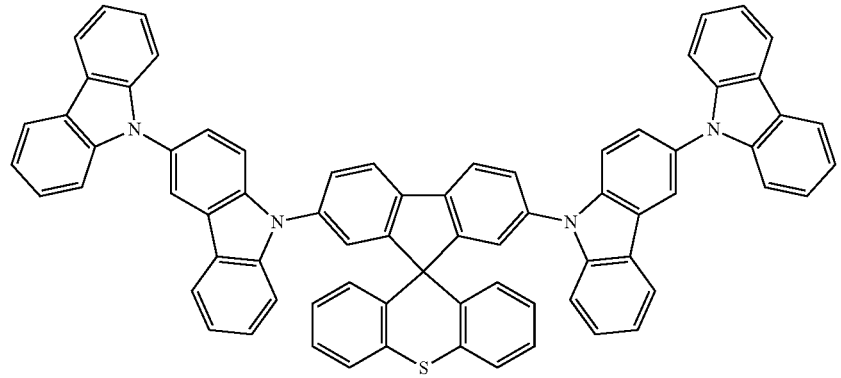
31
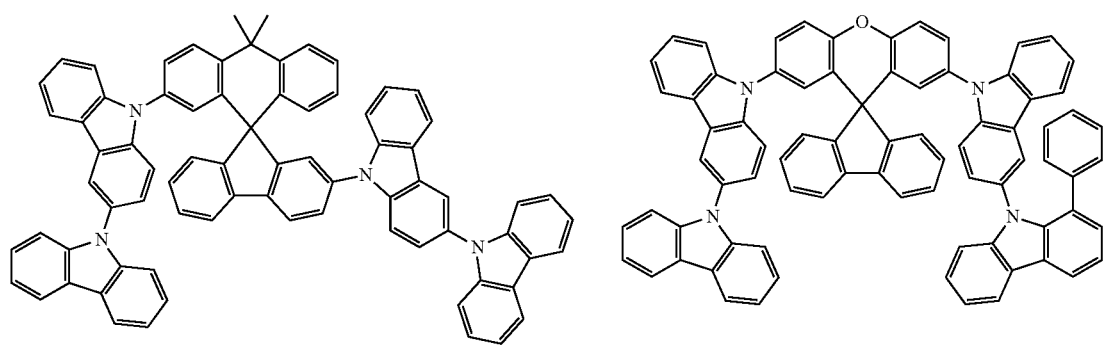
32
33
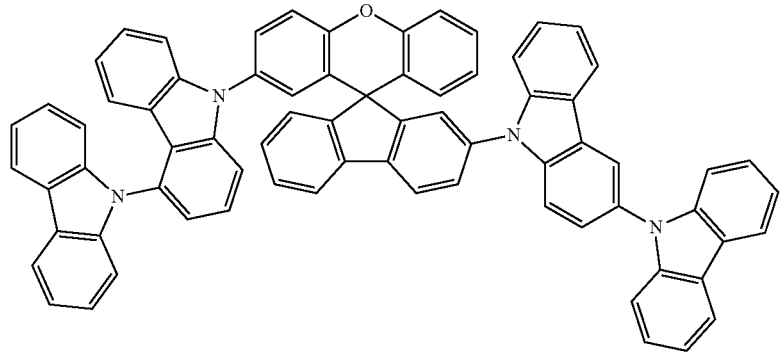
34
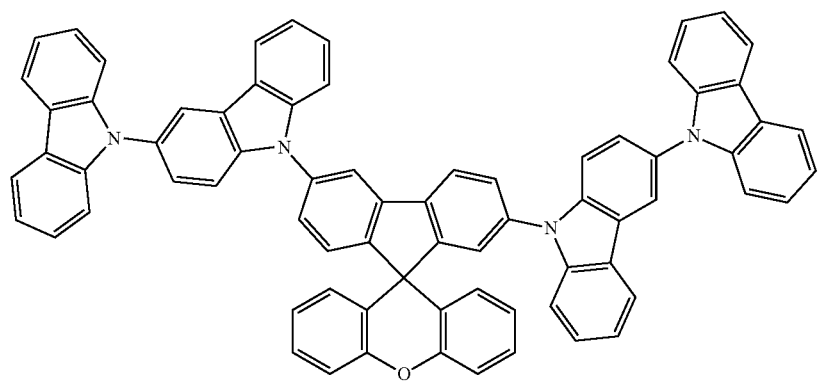

35
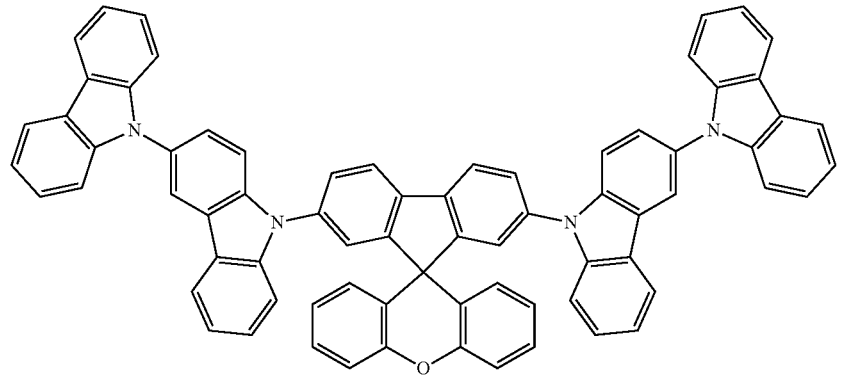
36
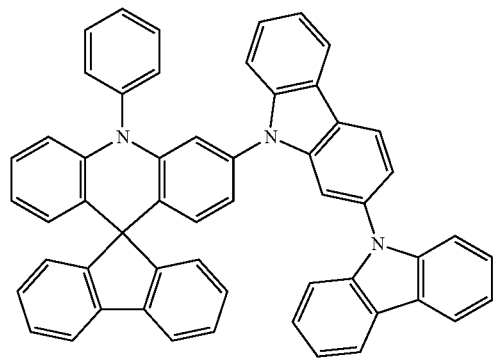
37
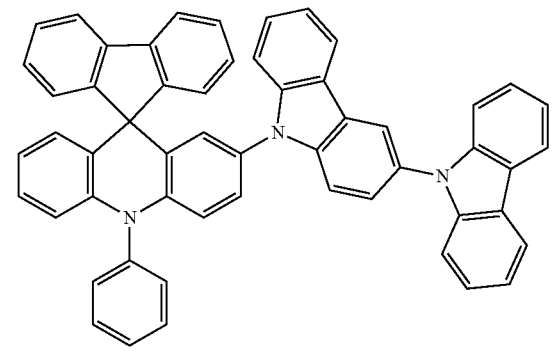
38
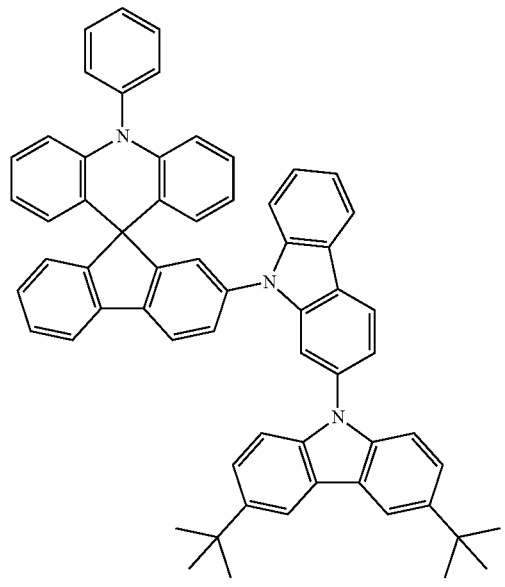
39
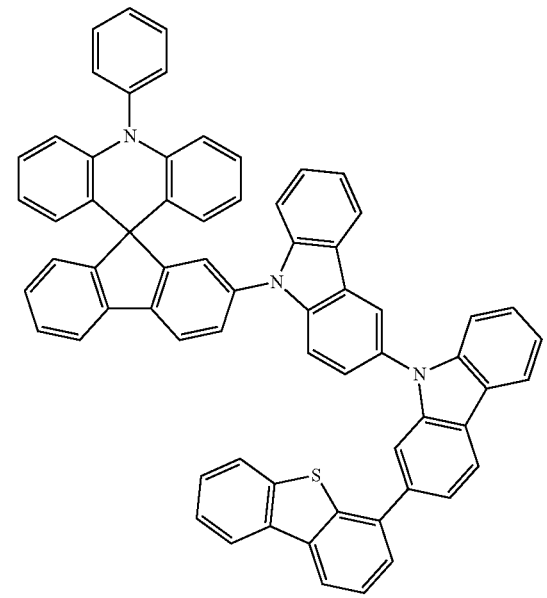

-continued
40
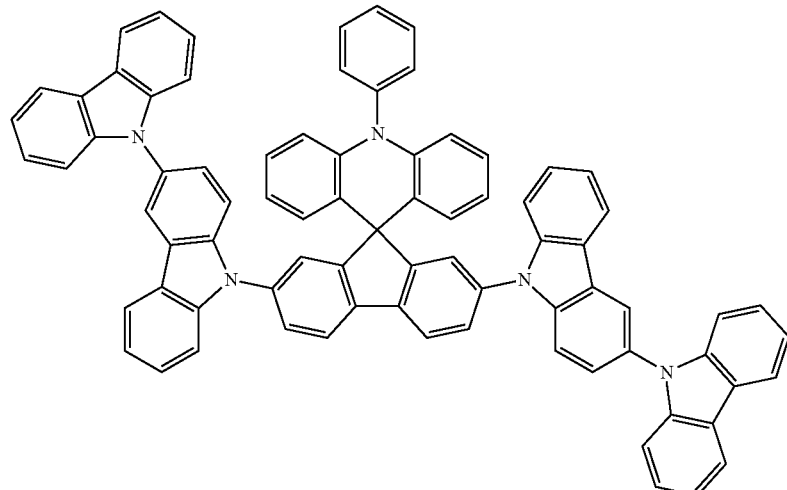
41
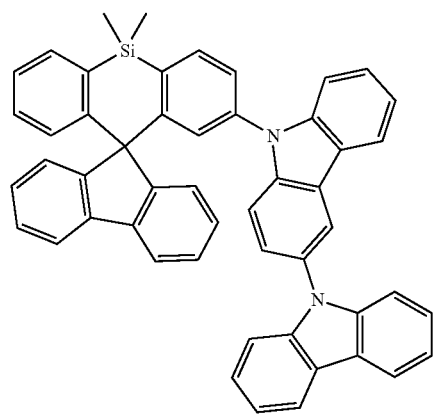
42
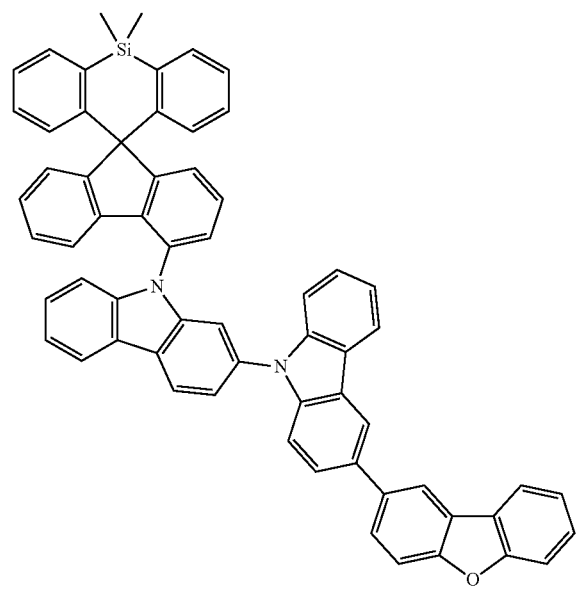
43
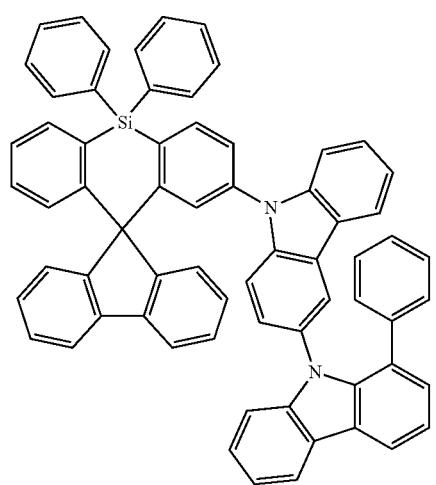
44
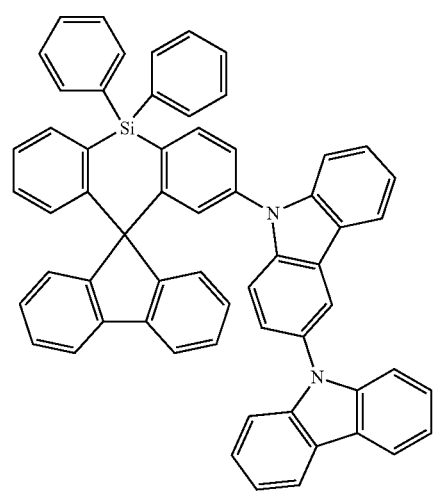

45
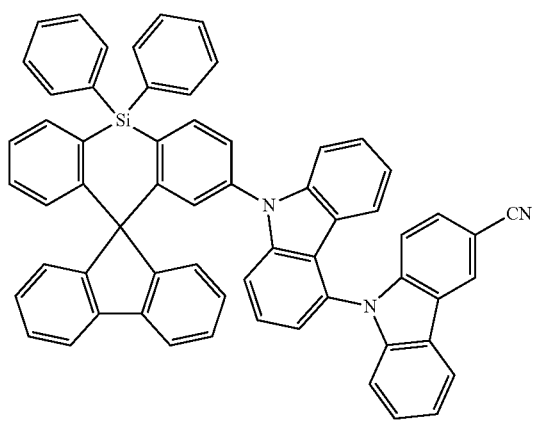

46
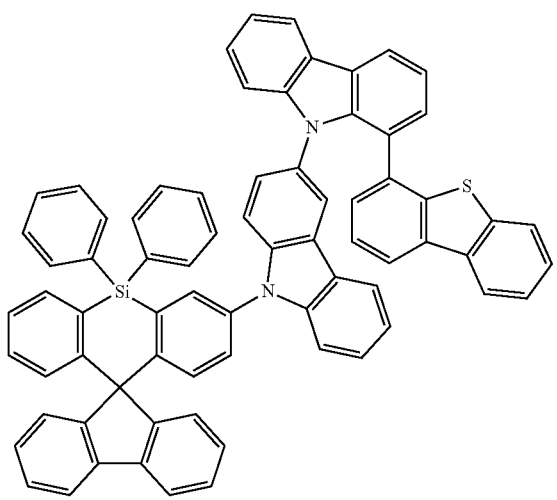

47
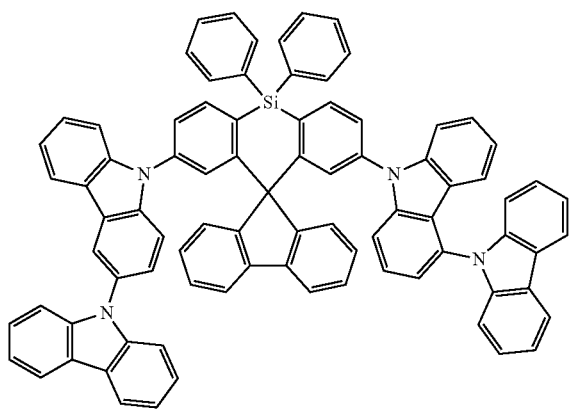

48
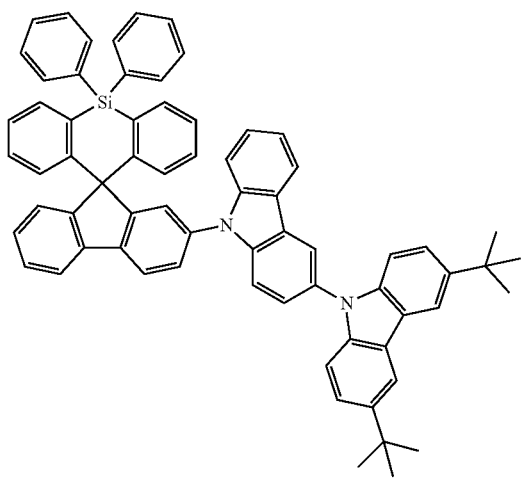

An organic electroluminescence device according to an embodiment may include a first electrode, a second electrode disposed on the first electrode, and an emission layer disposed between the first electrode and the second electrode. The first electrode and the second electrode may each independently include at least one selected from the group consisting of Ag, Mg, Cu, Al, Pt, Pd, Au, Ni, Nd, Ir, Cr, Li, Ca, LiF/Ca, LiF/Al, Mo, Ti, In, Sn, Zn, an oxide thereof, a compound thereof, and a mixture thereof. The emission layer may include a polycyclic compound of an embodiment.

In an embodiment, the emission layer may include a host and a dopant. The host may include the polycyclic compound.

In an embodiment, the dopant may be a phosphorescence dopant, or a thermally activated delayed fluorescence dopant.

In an embodiment, the emission layer may emit blue light.

BRIEF DESCRIPTION OF THE DRAWINGS

The accompanying drawings are incorporated in and constitute a part of this specification. The drawings illustrate embodiments of the invention and, together with the description, serve to explain the embodiments. In the drawings.

DETAILED DESCRIPTION OF THE EMBODIMENTS

Figure 1:
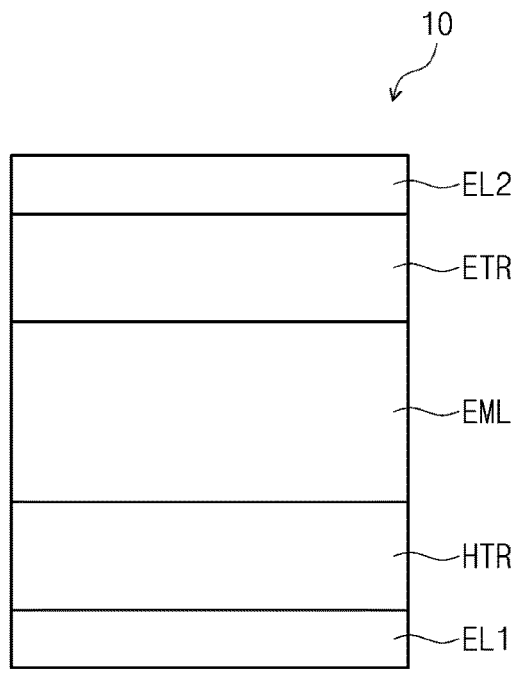
FIG. 1 is a schematic cross-sectional view illustrating an organic electroluminescence device according to an embodiment.

The invention may have various modifications and may be embodied in different forms, and example embodiments will be explained in detail with reference to the accompany drawings. The invention may, however, be embodied in different forms and should not be construed as limited to the embodiments set forth herein. Rather, all modifications, equivalents, and substituents which are included in the spirit and technical scope of the invention should be included.

Like reference numerals refer to like elements throughout. In the drawings, the dimensions of structures are exaggerated for clarity of illustration. It will be understood that, although the terms first, second, etc. may be used herein to describe various elements, these elements should not be limited by these terms. These terms are only used to distinguish one element from another element. Thus, a first element could be termed a second element without departing from the teachings of the invention. Similarly, a second element could be termed a first element. As used herein, the singular forms are intended to include the plural forms as well, unless the context clearly indicates otherwise.

In the specification and the claims, the term "and/or" is intended to include any combination of the terms "and" and "or" for the purpose of its meaning and interpretation. For example, "A and/or B" may be understood to mean "A, B, or A and B." The terms "and" and "or" may be used in the conjunctive or disjunctive sense and may be understood to be equivalent to "and/or".

The phrase "at least one of" is intended to include the meaning of "at least one selected from the group of" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be further understood that the terms "comprises," "comprising," "includes," and/or "including," when used in this specification, specify the presence of stated features, numerals, steps, operations, elements, parts, or the combination thereof, but do not preclude the presence or addition of one or more other features, numerals, steps, operations, elements, parts, or the combination thereof.

It will also be understood that when a layer, a film, a region, a plate, etc. is referred to as being "on" or "above" another part, it can be "directly on" the other part, or intervening layers may also be present. It will also be understood that when a layer, a film, a region, a plate, etc. is referred to as being "under" or "below" another part, it can be "directly under" the other part, or intervening layers may also be present. When an element is referred to as being disposed "on" another element, it can be disposed under the other element.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

Unless otherwise defined, all terms used herein (including technical and scientific terms) have the same meaning as commonly understood by those skilled in the art to which this disclosure pertains. It will be further understood that terms, such as those defined in commonly used dictionaries, should be interpreted as having a meaning that is consistent with their meaning in the context of the relevant art and will not be interpreted in an ideal or excessively formal sense unless clearly defined in the specification.

The term "substituted or unsubstituted" corresponds to substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. In addition, each of the substituents may be substituted or unsubstituted. For example, a biphenyl group may be interpreted as an aryl group or a phenyl group substituted with a phenyl group.

The alkyl may be a linear, branched or cyclic type. The carbon number of the alkyl may be in a range from 1 to 50. In an embodiment, the carbon number of the alkyl may be in a range from 1 to 30. In an embodiment, the carbon number of the alkyl may be in a range from 1 to 20. In an embodiment, the carbon number of the alkyl may be in a range from 1 to 10. In an embodiment, the carbon number of the alkyl may be in a range from 1 to 6. For example, the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without being limited thereto.

The hydrocarbon ring group may be an optional functional group or substituent derived from an aliphatic hydrocarbon ring. The hydrocarbon ring group may be a saturated hydrocarbon ring group of 5 to 20 carbon atoms for forming a ring.

The aryl group may be an optional functional group or substituent derived from an aromatic hydrocarbon ring. The aryl group may be a monocyclic aryl group or a polycyclic aryl group. The carbon number for forming a ring in the aryl group may be in a range from 6 to 30. In an embodiment, the carbon number for forming a ring in the aryl group may be in a range from 6 to 20. In an embodiment, the carbon number for forming a ring in the aryl group may be in a range from 6 to 15. For example, the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., without being limited thereto.

The heterocyclic group may include one or more among B, O, N, P, Si and S as heteroatoms. If the heterocyclic group includes two or more heteroatoms, two or more heteroatoms may be the same or different. The heterocyclic group may be a monocyclic heterocyclic group or a polycyclic heterocyclic group, and has a concept including a heteroaryl group. The carbon number for forming a ring of the heteroaryl group may be in a range from 2 to 30. In an embodiment, the carbon number for forming a ring of the heteroaryl group may be in a range from 2 to 20. In an embodiment, the carbon number for forming a ring of the heteroaryl group may be in a range from 2 to 10.

The carbon number for forming a ring of the heteroaryl group may be in a range from 2 to 30. In an embodiment, the carbon number for forming a ring of the heteroaryl group may be in a range from 2 to 20. In an embodiment, the carbon number for forming a ring of the heteroaryl group may be in a range from 2 to 10. For example, the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, isooxazole, oxadiazole, thiadiazole, phenothiazine, dibenzosilole, dibenzofuran, etc., without being limited thereto.

The explanation for the alkyl group may be applied to the divalent alkyl group except that the divalent alkyl group is a divalent group. The explanation for the aryl group may be applied to the arylene group except that the arylene group is a divalent group. The explanation for the heteroaryl group may be applied to the heteroarylene group except that the heteroarylene group is a divalent group.

The silyl group may include an alkyl silyl group and an aryl silyl group. For example, the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., without being limited thereto.

The alkenyl group may be a linear chain or a branched chain. The carbon number is not specifically limited but may be in a range from 2 to 30. In an embodiment, the carbon number for the alkenyl group may be in a range from 2 to 20. In an embodiment, the carbon number for the alkenyl group may be in a range from 2 to 10. For example, the alkenyl group may include a vinyl group, a 1-butenyl group, a 1-pentenyl group, a 1,3-butadienyl aryl group, a styrenyl group, a styrylvinyl group, etc., without being limited thereto.

The aryl group in the aryl silyl group may be the same as the examples of the above-described aryl group.

The direct linkage may mean a single bond.

FIG. 1 is a schematic cross-sectional view showing an organic electroluminescence device according to an embodiment. The organic electroluminescence device 10 according to an embodiment may include a first electrode ELL a hole transport region HTR, an emission layer EML, an electron transport region ETR, and a second electrode EL2 stacked in order.

FIGS. 1 to 4 are schematic cross-sectional views showing organic electroluminescence devices according to embodiments. Referring to FIGS. 1 to 4, in an organic electroluminescence device 10 according to an embodiment, a first electrode EL1 and a second electrode EL2 are oppositely disposed, and between the first electrode EL1 and the second electrode EL2, an emission layer EML may be disposed.

In addition, the organic electroluminescence device 10 of an embodiment further includes a plurality of functional groups between the first electrode EL1 and the second electrode EL2 in addition to the emission layer EML. The plurality of the functional groups may include a hole transport region HTR and an electron transport region ETR. For example, the organic electroluminescence device 10 of an embodiment may include a first electrode EL1, a hole transport region HTR, an emission layer EML, an electron transport region ETR, and a second electrode EL2, stacked in order. In addition, the organic electroluminescence device 10 of an embodiment may include a capping layer CPL which is disposed on the second electrode EL2.

The organic electroluminescence device 10 of an embodiment may include a polycyclic compound of an embodiment in the emission layer EML, which is disposed between the first electrode EL1 and the second electrode EL2. However, an embodiment is not limited thereto, and the organic electroluminescence device 10 of an embodiment may include a polycyclic compound of an embodiment in the hole transport region HTR or the electron transport region ETR, which are functional groups disposed between the first electrode EL1 and the second electrode EL2, or include a polycyclic compound of an embodiment in the capping layer CPL disposed on the second electrode EL2 in addition to the emission layer EML.

Figure 2:
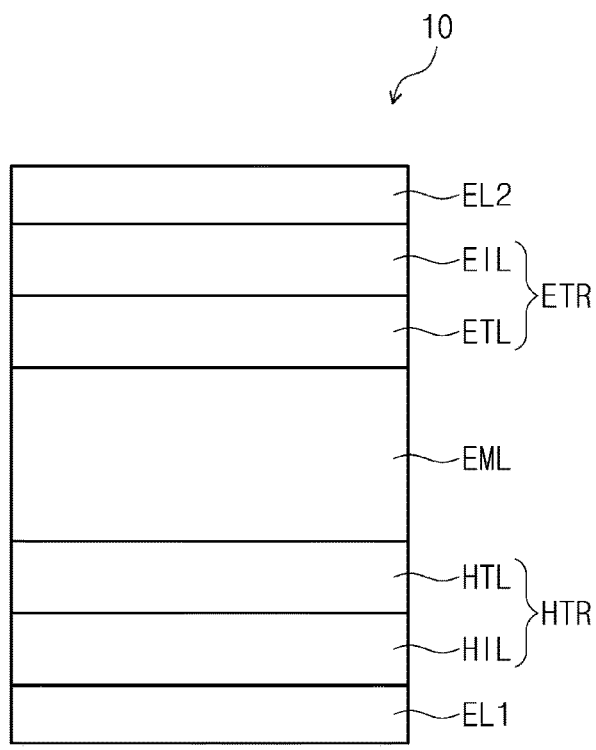
FIG. 2 is a schematic cross-sectional view illustrating an organic electroluminescence device according to an embodiment.
Figure 3:
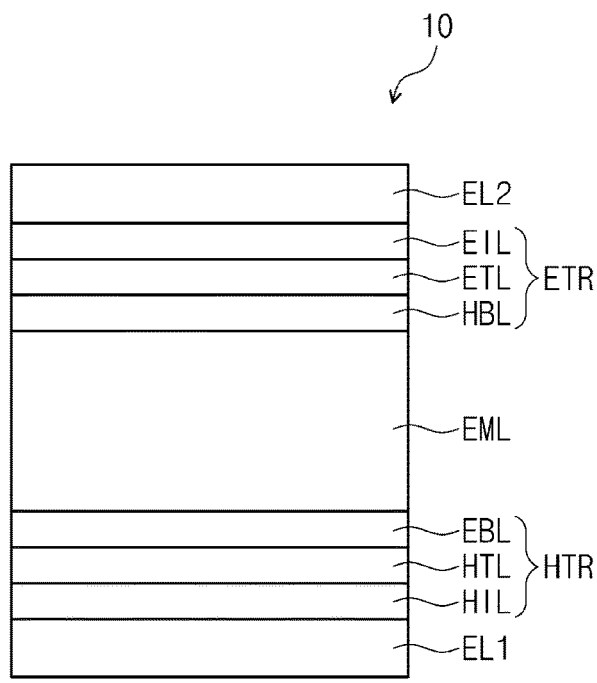
FIG. 3 is a schematic cross-sectional view illustrating an organic electroluminescence device according to an embodiment.
Figure 4:
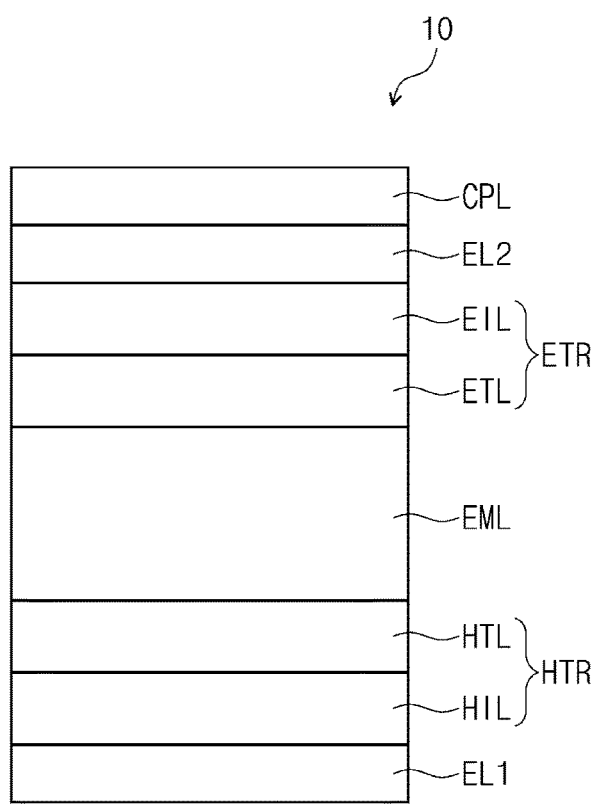
FIG. 4 is a schematic cross-sectional view illustrating an organic electroluminescence device according to an embodiment.

In comparison with FIG. 1, FIG. 2 shows the schematic cross-sectional view of an organic electroluminescence device 10 of an embodiment, wherein a hole transport region HTR includes a hole injection layer HIL and a hole transport layer HTL, and an electron transport region ETR includes an electron injection layer EIL and an electron transport layer ETL. In comparison with FIG. 1, FIG. 3 shows the schematic cross-sectional view of an organic electroluminescence device 10 of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. In comparison with FIG. 2, FIG. 4 shows the schematic cross-sectional view of an organic electroluminescence device 10 of an embodiment, including a capping layer CPL disposed on the second electrode EL2.

The first electrode EL1 has conductivity. The first electrode EL1 may be formed using a metal alloy or a conductive compound. The first electrode EL1 may be an anode. The first electrode EL1 may be a pixel electrode. The first electrode EL1 may be a transmissive electrode, a transflective electrode, or a reflective electrode. If the first electrode EL1 is the transmissive electrode, the first electrode EL1 may include a transparent metal oxide, for example, indium tin oxide (ITO), indium zinc oxide (IZO), zinc oxide (ZnO), and indium tin zinc oxide (ITZO), etc. If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The first electrode EL1 may have a structure including a plurality of layers including a reflective layer or a transflective layer formed using the above materials, and a transmissive conductive layer formed using ITO, IZO, ZnO, ITZO, etc. For example, the first electrode EL1 may include a three-layer structure of ITO/Ag/ITO. However, an embodiment is not limited thereto. The thickness of the first electrode EL1 may be in a range from about 1,000 Å to about 10,000 Å. In an embodiment, the thickness of the first electrode EL1 may be in a range from about 1,000 Å to about 3,000 Å.

The hole transport region HTR is disposed on the first electrode EL1. The hole transport region HTR may include at least one of a hole injection layer HIL, a hole transport layer HTL, a hole buffer layer (not shown), and an electron blocking layer EBL.

The hole transport region HTR may have a single layer formed using a single material, a single layer formed using different materials, or a multilayer structure including layers formed using different materials.

For example, the hole transport region HTR may have a single layer structure of the hole injection layer HIL or the hole transport layer HTL, or a single layer structure formed using a hole injection material and a hole transport material. In addition, the hole transport region HTR may have a structure of a single layer formed using different materials, or a structure stacked from the first electrode EL1 of hole injection layer HIL/hole transport layer HTL, hole injection layer HIL/hole transport layer HTL/hole buffer layer (not shown), hole injection layer HIL/hole buffer layer (not shown), hole transport layer HTL/hole buffer layer, or hole injection layer HIL/hole transport layer HTL/electron blocking layer EBL, without being limited thereto.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4',4"-tris(N,N-diphenylamino)triphenylamine (TDATA), 4,4',4"-tris{N,-2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium tetrakis(pentafluorophenyl)borate, and dipyrazino[2,3-f: 2',3'-h]quinoxaline-2,3,6,7,10,11-hexacarbonitrile (HAT-CN).

The hole transport layer HTL may include, for example, carbazole derivatives such as N-phenyl carbazole and polyvinyl carbazole, fluorene-based derivatives, N,N'-bis(3-methylphenyl)-N,N'-diphenyl-[1,1-biphenyl]-4,4'-diamine (TPD), triphenylamine-based derivatives such as 4,4',4"-tris (carbazol-9-yl)triphenylamine (TCTA), N,N'-di(naphthalene-1-yl)-N,N'-diphenyl-benzidine (NPB), 4,4'-cyclohexylidene bis[N,N-bis(4-methylphenyl)benzeneamine] (TAPC), 4,4'-bis[N,N'-(3-tolyl)amino]-3,3'-dimethylbiphenyl (HMTPD), 1,3-bis(N-carbazolyl)benzene (mCP), 9-(4-tert-butylphenyl)-3,6-bis(triphenylsilyl)-9H-carbazole (CzSi), etc.

The thickness of the hole transport region HTR may be in a range from about 100 Å to about 10,000 Å. In an embodiment, the thickness of the hole transport region HTR may be in a range from about 100 Å to about 5,000 Å. The thickness of the hole injection region HIL may be in a range from about 30 Å to about 1,000 Å. The thickness of the hole transport layer HTL may be in a range from about 30 Å to about 1,000 Å. For example, the thickness of the electron blocking layer EBL may be in a range from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material to increase conductivity in addition to the above-described materials. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without being limited thereto. For example, the p-dopant may include quinone derivatives such as tetracyanoquinodimethane (TCNQ) and 2,3,5,6-tetrafluoro-7,7,8,8-tetracyanoquinodimethane (F4-TCNQ), metal oxides such as tungsten oxide and molybdenum oxide, etc., without being limited thereto.

As described above, the hole transport region HTR may further include at least one of a hole buffer layer (not shown) and an electron blocking layer EBL in addition to the hole injection layer HIL and the hole transport layer HTL. The hole buffer layer (not shown) may compensate an optical resonance distance according to the wavelength of light emitted from an emission layer EML to increase light emission efficiency. Materials which may be included in the hole transport region HTR may be used as materials included in the hole buffer layer (not shown). The electron blocking layer EBL is a layer playing the role of preventing the electron injection from the electron transport region ETR to the hole transport region HTR.

The emission layer EML is disposed on the hole transport region HTR. The emission layer EML may have a thickness in a range from about 100 Å to about 1,000 Å. In an embodiment, the emission layer EML may have a thickness in a range from about 100 Å to about 300 Å. The emission layer EML may have a single layer formed using a single material, a single layer formed using different materials, or a multilayer structure having layers formed using different materials.

The emission layer EML may include the polycyclic compound of an embodiment. The polycyclic compound of an embodiment may be represented by Formula 1.

[Formula 1]

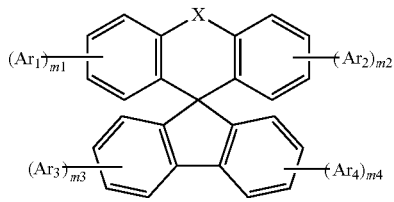

In Formula 1, X may be O, S, $CR_1R_2$, $NR_3$, or $SiR_4R_5$. $R_1$ to $R_5$ may be each independently a hydrogen atom, a deuterium atom, an alkyl group, or an aryl group. The alkyl group may be a substituted or unsubstituted alkyl group of 1 to 20 carbon atoms. The aryl group may be a substituted or unsubstituted aryl group of 6 to 30 carbon atoms for forming a ring.

For example, $R_1$ to $R_5$ may be each independently a substituted or unsubstituted alkyl group of 1 to 5 carbon atoms, or a substituted or unsubstituted phenyl group. The substituted or unsubstituted alkyl group of 1 to 5 carbon atoms may be a methyl group, an ethyl group, an isopropyl group, or a t-butyl group.

At least one of $Ar_1$ to $Ar_4$ may be represented by Formula 2, which will be explained below, and the remainder may be each independently a hydrogen atom, a deuterium atom, an alkyl group, or an aryl group. The alkyl group may be a substituted or unsubstituted alkyl group of 1 to 20 carbon atoms. The aryl group may be a substituted or unsubstituted aryl group of 6 to 30 carbon atoms for forming a ring.

In Formula 1, m1 to m4 may be each independently an integer from 0 to 4. At least one of m1 to m4 may be an integer from 1 to 4. In Formula 1, m1 to m4 may be each independently 0 or 1, and at least one of m1 to m4 may be 1. For example, any one or two among m1 to m4 may be 1. If any two among m1 to m4 are 1 and the remainder are 0, m1 and m2, m1 and m3, m1 and m4, or m3 and m4 may be 1. If m1 is 2 or more, two or more $Ar_1$ groups may be the same or different. If m2 is 2 or more, two or more $Ar_2$ groups may be the same or different. If m3 is 2 or more, two or more $Ar_3$ groups may be the same or different. If m4 is 2 or more, two or more $Ar_4$ groups may be the same or different.

At least one of $Ar_1$ to $Ar_4$ may be represented by the following Formula 2:

[Formula 2]

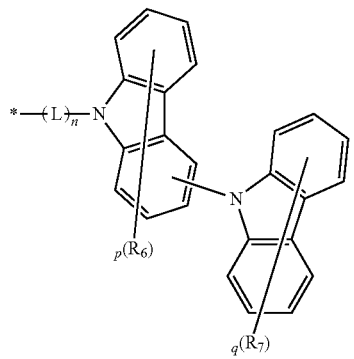

In Formula 2,

—* may mean a connecting part.

In Formula 2, $R_6$ and $R_7$ may be each independently a hydrogen atom, a deuterium atom, an alkyl group, a silyl group, an aryl group, or a heteroaryl group. The alkyl group may be a substituted or unsubstituted alkyl group of 1 to 20 carbon atoms. The silyl group may be a substituted or unsubstituted silyl group. The aryl group may be a substituted or unsubstituted aryl group of 6 to 30 carbon atoms for forming a ring. The heteroaryl group may be a substituted or unsubstituted heteroaryl group of 2 to 30 carbon atoms for forming a ring.

$R_7$ may be a hydrogen atom, an alkyl group of 1 to 5 carbon atoms, a silyl group, a phenyl group, a naphthyl group, or a dibenzoheterocyclic group. The alkyl group of 1 to 5 carbon atoms may be a methyl group, an ethyl group, an isopropyl group or a t-butyl group. The silyl group may be an alkyl silyl group or an aryl silyl group. The aryl silyl group may be a triphenylsilyl group. The phenyl group may be a substituted or unsubstituted phenyl group. The naphthyl group may be a substituted or unsubstituted naphthyl group. The dibenzoheterocyclic group may be a dibenzofuran group, or a dibenzothiophene group. The dibenzofuran group may be a substituted or unsubstituted dibenzofuran group. The dibenzothiophene group may be a substituted or unsubstituted dibenzothiophene group.

L may be a direct linkage, a divalent alkyl group, an arylene group, or a heteroarylene group. The divalent alkyl group may be a substituted or unsubstituted divalent alkyl group of 1 to 20 carbon atoms. The arylene group may be a substituted or unsubstituted arylene group of 6 to 30 carbon atoms. The heteroarylene group may be a substituted or unsubstituted heteroarylene group of 2 to 30 carbon atoms.

In Formula 2, n may be 0 or 1. In Formula 2, p may be an integer from 0 to 7. In Formula 2, q may be an integer from 0 to 8. For example, q may be 1 or 2. If q is an integer of 1 or more, q may not be a hydrogen atom. If q is 2 or more, two or more $R_7$ groups may be the same or different.

For example, $Ar_1$ to $Ar_4$ may be each independently represented by Formula 2.

Formula 1 may be represented by the following Formula 1-1 to Formula 1-5:

[Formula 1-1]

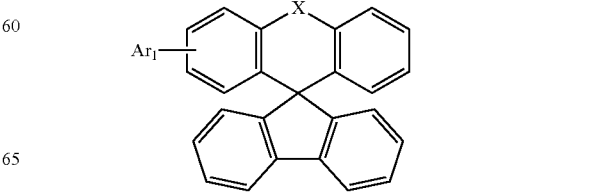

-continued

[Formula 1-2]
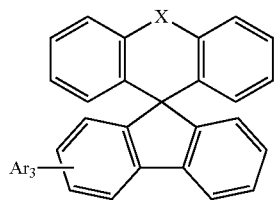

[Formula 1-3]
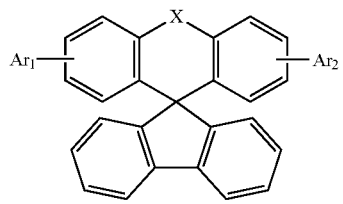

[Formula 1-4]
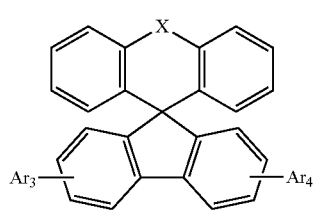

[Formula 1-5]
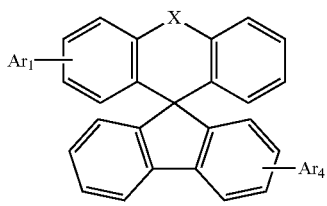

Formula 1-1 to Formula 1-5 are formulae in which m1 to m4 in Formula 1 are specified. In Formula 1-1 to Formula 1-5, $Ar_1$ to $Ar_4$ may be represented by Formula 2.

Formula 2 may be represented by Formula 2-1.

[Formula 2-1]
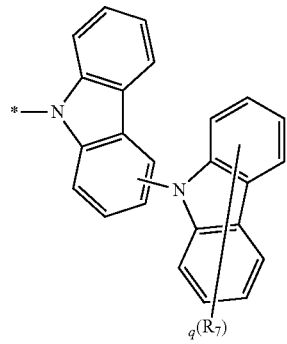

Formula 2-1 is a specified formula where n and p are 0. In Formula 2-1, $R_7$ and q may be the same as defined in Formula 2.

Formula 1 may be represented by Formula 3.

[Formula 3]
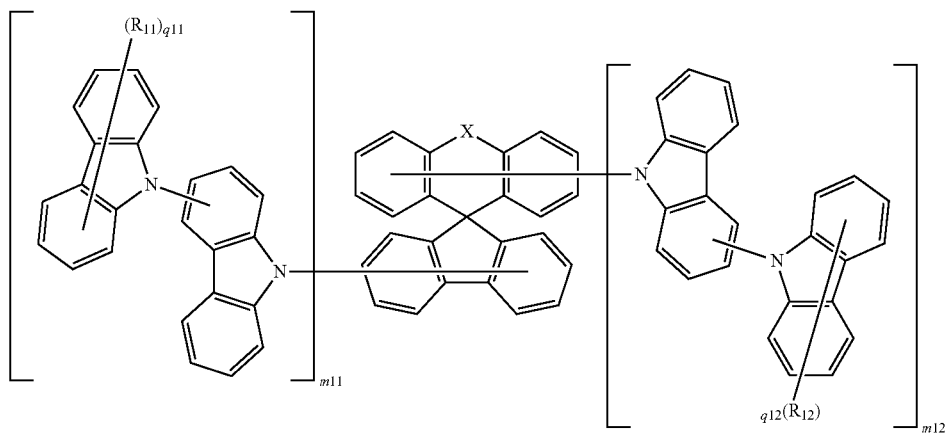

$R_{11}$ and $R_{12}$ may be each independently a hydrogen atom, a deuterium atom, an alkyl group, a silyl group, an aryl group or a heteroaryl group. The alkyl group may be a substituted or unsubstituted alkyl group of 1 to 20 carbon atoms. The silyl group may be a substituted or unsubstituted silyl group. The aryl group may be a substituted or unsubstituted aryl group of 6 to 30 carbon atoms for forming a ring. The heteroaryl group may be a substituted or unsubstituted heteroaryl group of 2 to 30 carbon atoms for forming a ring. $R_{11}$ and $R_{12}$ may be defined by the same manner as $R_7$ in Formula 2.

In Formula 3, q11 and q12 may be each independently an integer from 0 to 8. For example, q11 and q12 may be each independently 1 or 2. If q11 is 1, $R_{11}$ may not be a hydrogen atom. If q12 is 1, $R_{12}$ may not be a hydrogen atom. If q11 is 2, two $R_{11}$ groups may be different from each other. If q12 is 2, two $R_{12}$ groups may be different from each other.

In Formula 3, m11 and m12 may be each independently an integer from 0 to 2. At least one of m11 or m12 may be an integer of 1 or 2.

X may be the same as defined in Formula 1.

Formula 3 may be represented by Formula 3-1.

In Formula 3-1, $R_{21}$ to $R_{24}$ may be each independently a hydrogen atom, a deuterium atom, an alkyl group, a silyl group, an aryl group, or a heteroaryl group. The alkyl group may be a substituted or unsubstituted alkyl group of 1 to 20 carbon atoms. The silyl group may be a substituted or unsubstituted silyl group, and the aryl group may be a substituted or unsubstituted aryl group of 6 to 30 carbon atoms for forming a ring. The heteroaryl group may be a substituted or unsubstituted heteroaryl group of 2 to 30 carbon atoms for forming a ring. In an embodiment, $R_{21}$ to $R_{24}$ may be defined by the same manner as $R_7$ in Formula 2.

In Formula 3-1, m21 to m24 may be each independently 0 or 1, where at least one of m21 to m24 may be 1. For example, any one among m21 to m24 may be 1. If any two among m21 to m24 are 1 and the remainder are 0, m21 and m22, m21 and m23, or m23 and m24 may be 1.

In Formula 3-1, q21 to q24 may be each independently an integer from 0 to 8.

In Formula 3-1, X may be the same as defined in Formula 1. In an embodiment, X may be the same as defined in Formula 3.

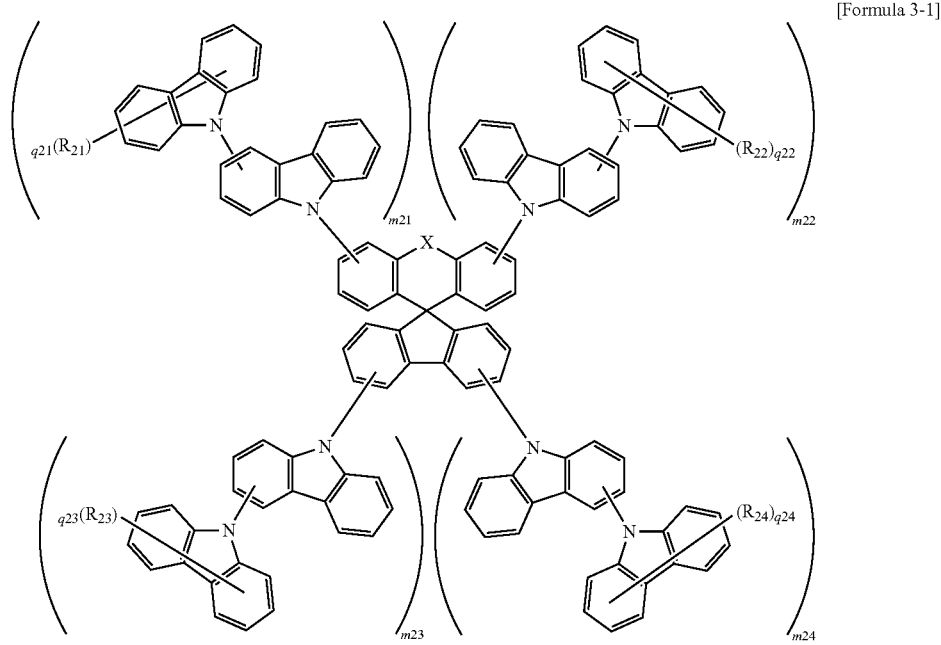

[Formula 3-1]

Formula 1 may be any one among the compounds represented in the following Compound Group 1:
[Compound Group 1]
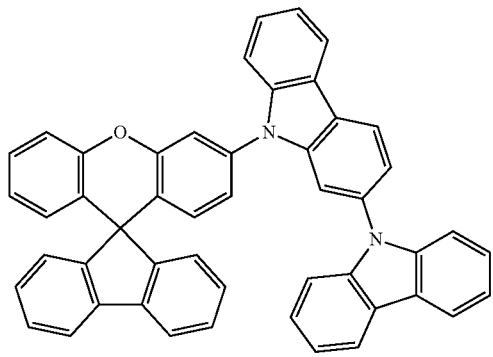
1
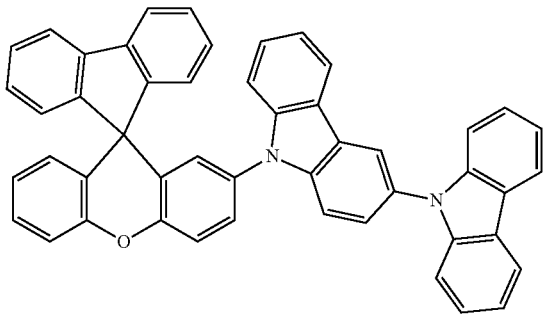
2
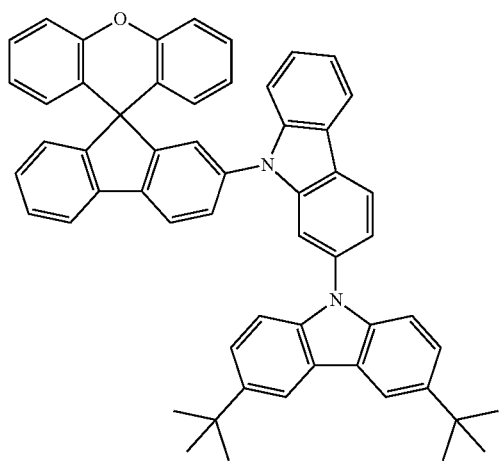
3
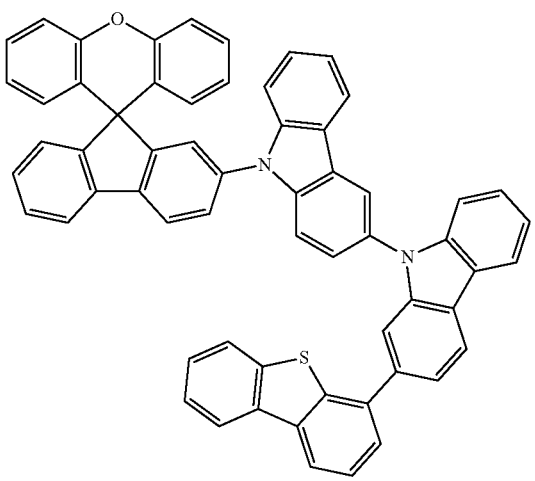
4
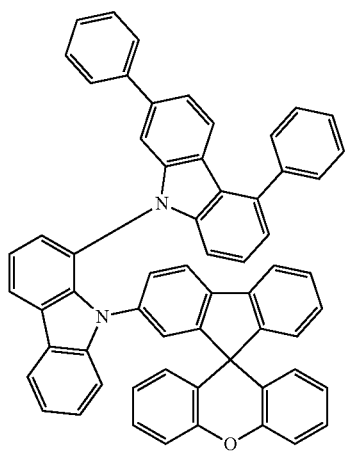
5
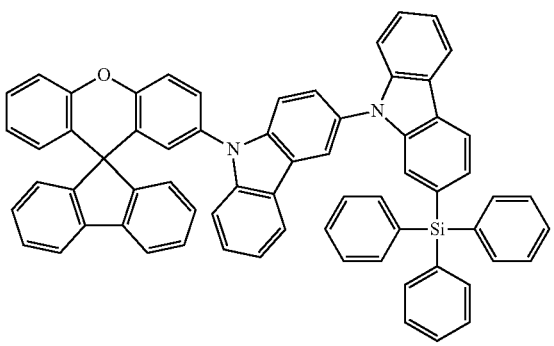
6

7
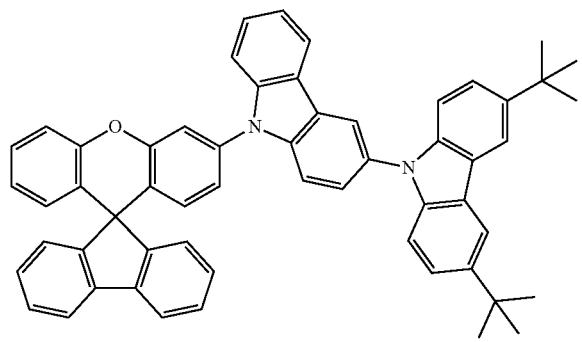
8
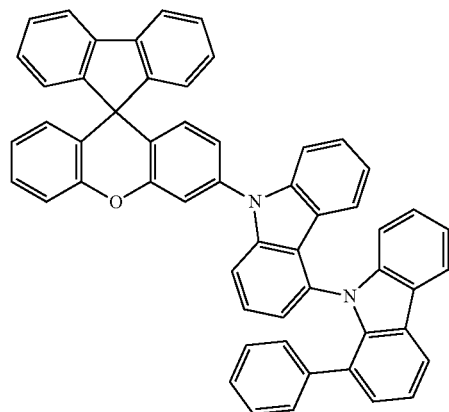
9
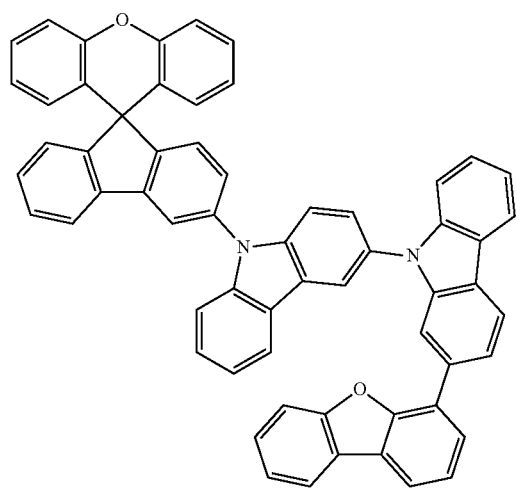
10
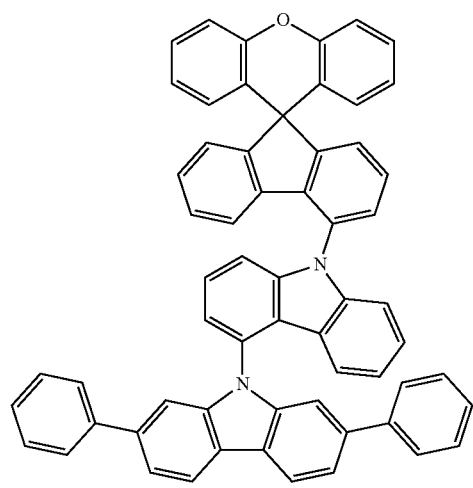
11
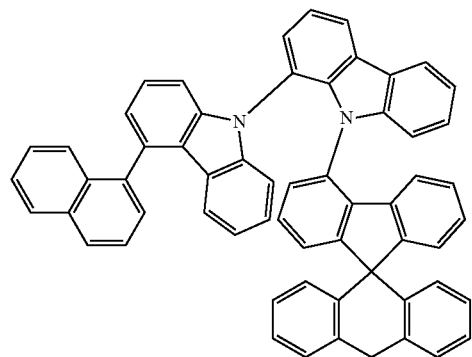
12
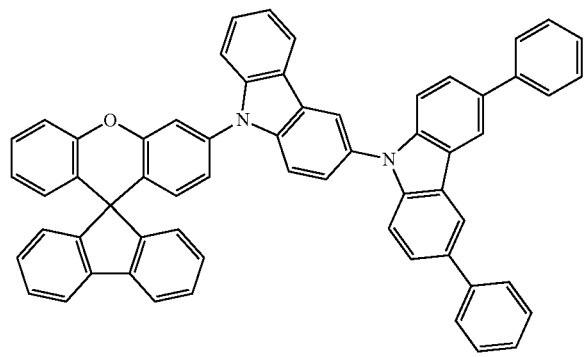

-continued
13
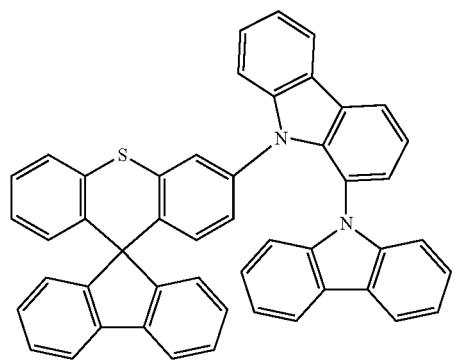
14
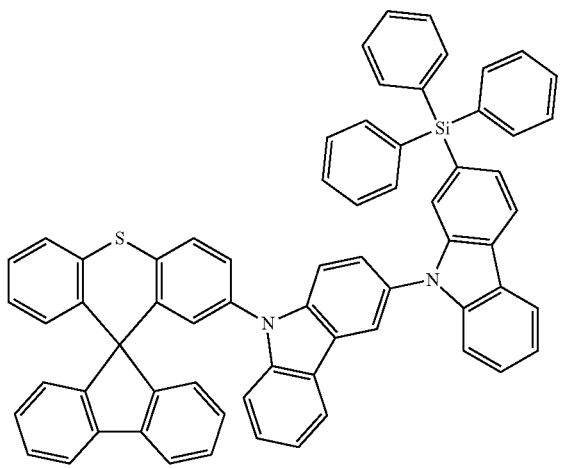
15
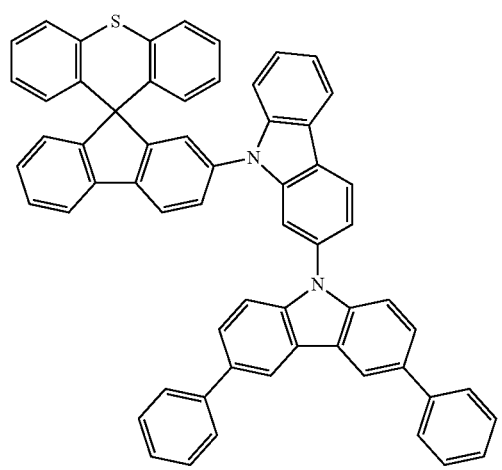
16
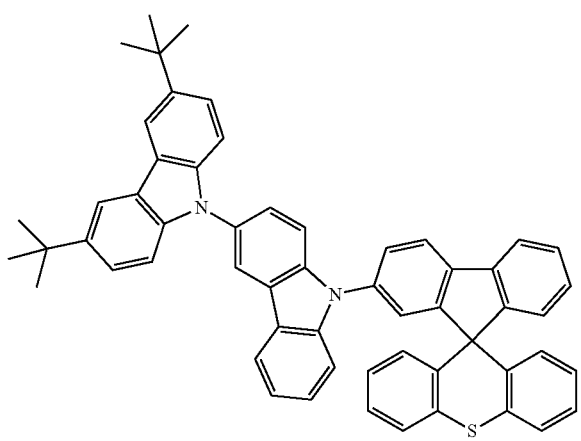
17
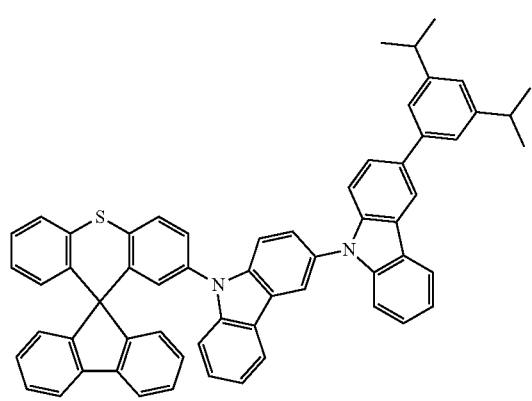
18
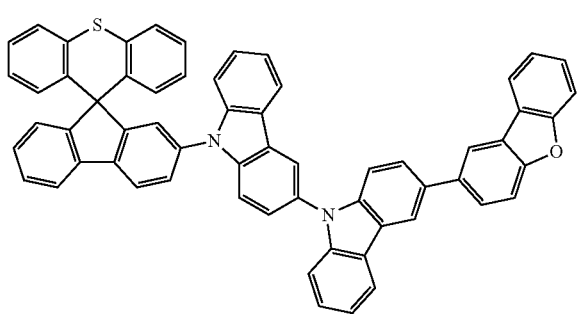

-continued
19
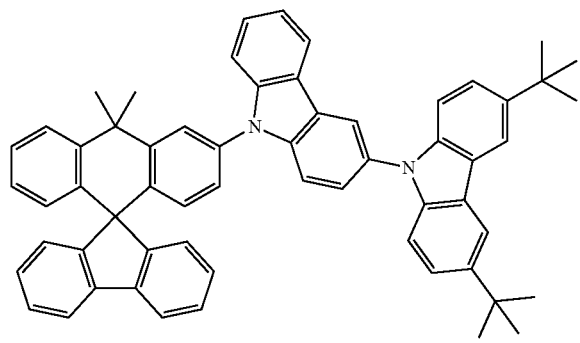
20
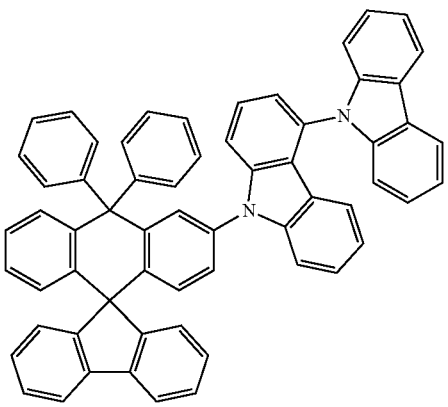
21
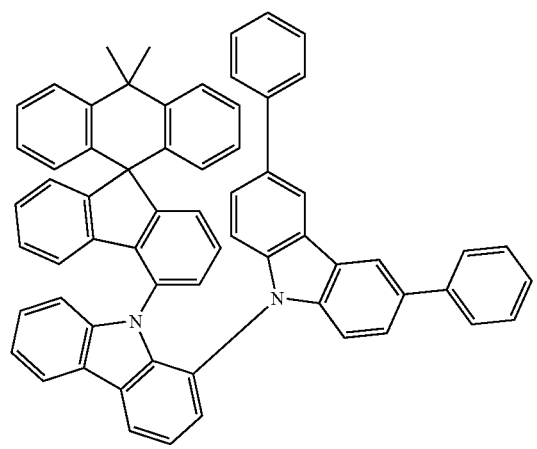
22
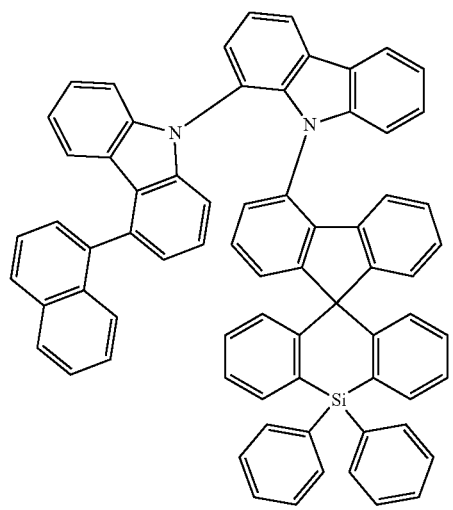
23
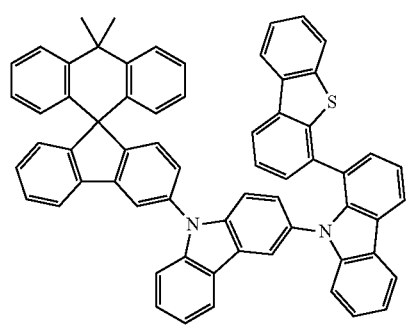
24
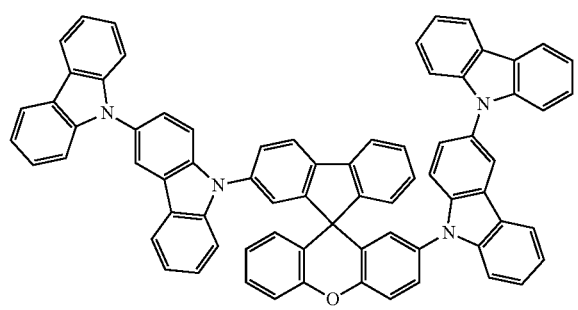
25
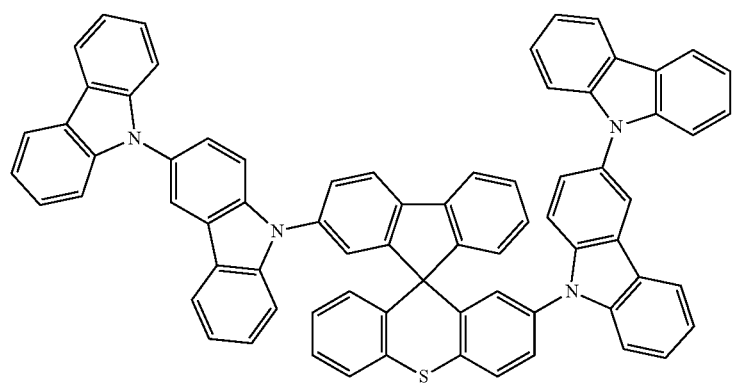

26
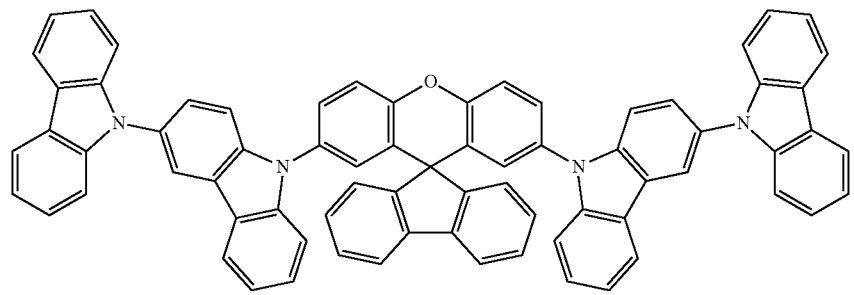
27
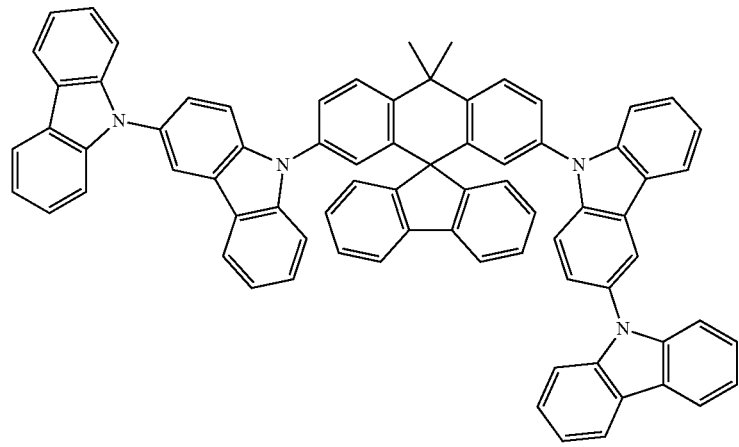
28
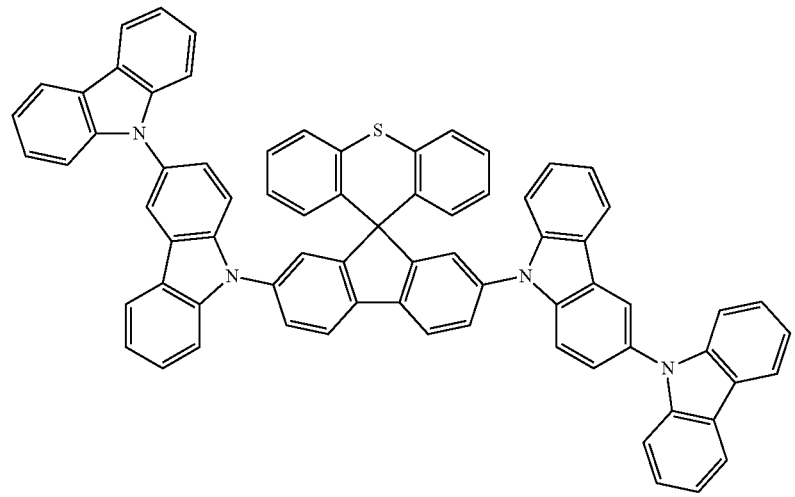
29
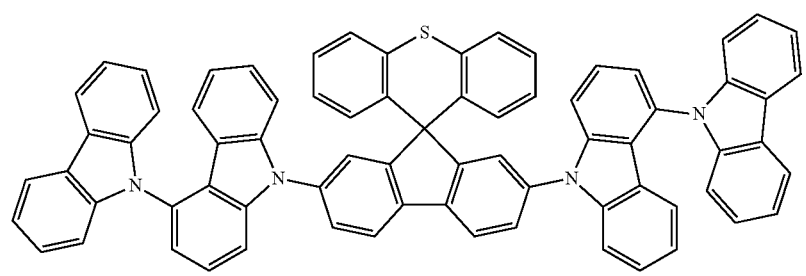

-continued
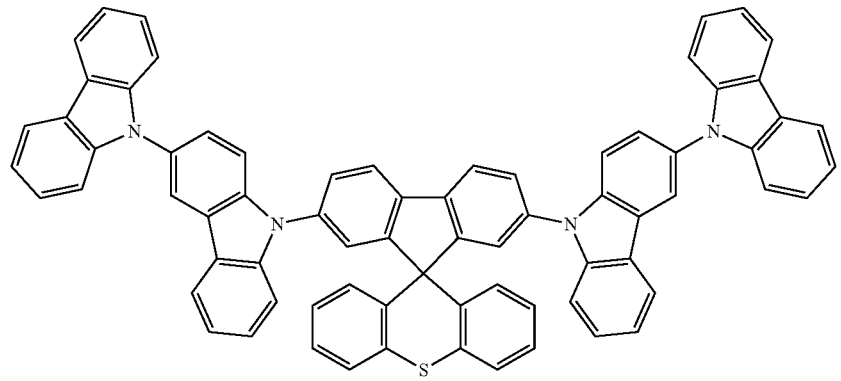
30
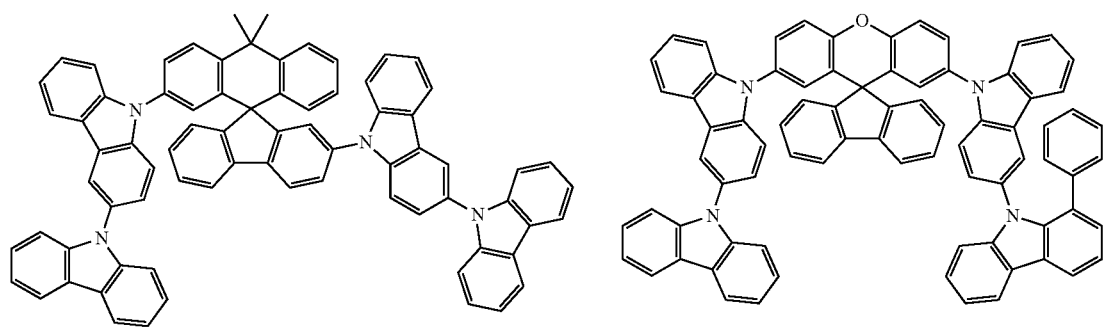
31
32
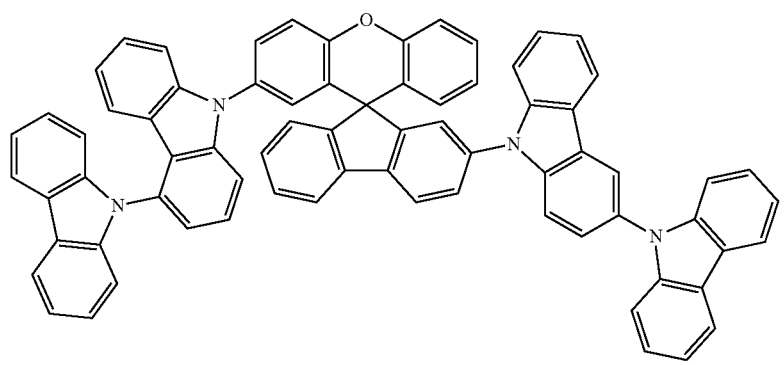
33
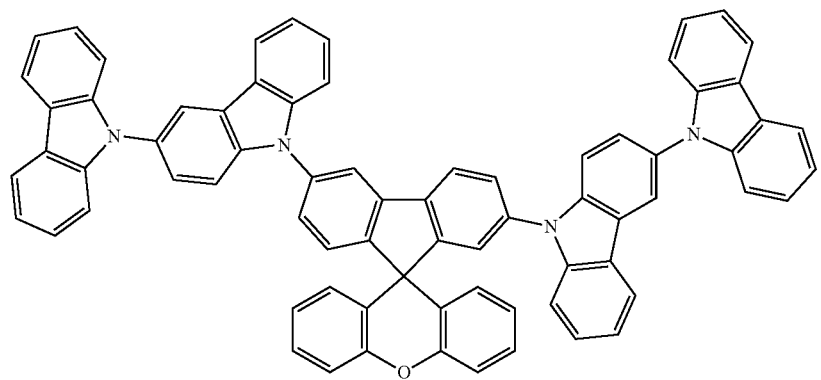
34

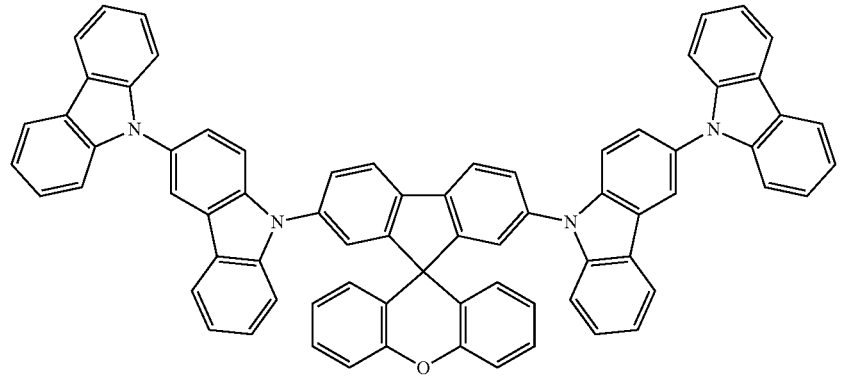
35
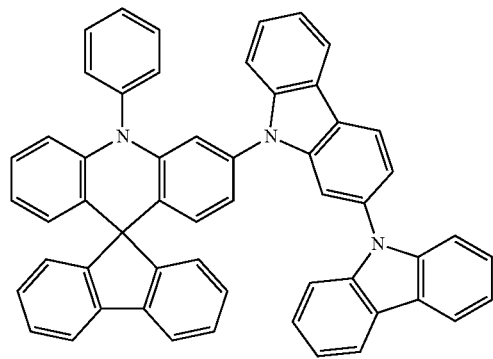
36
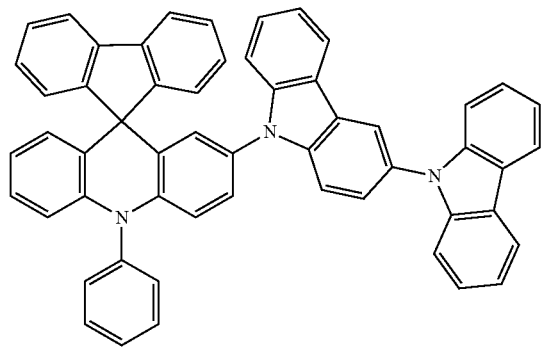
37
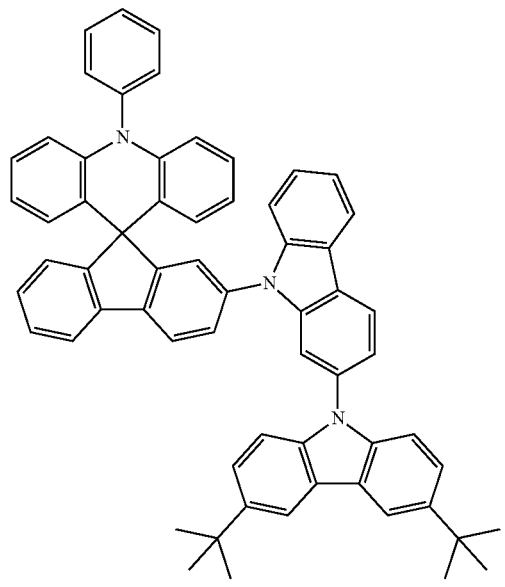
38
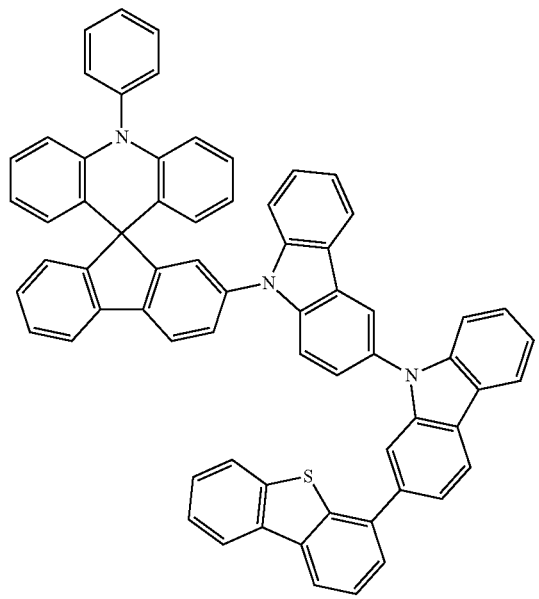
39

40
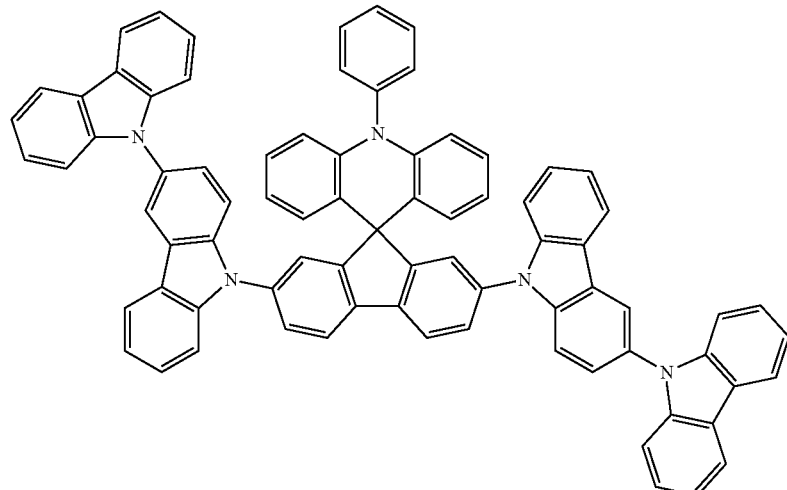
41
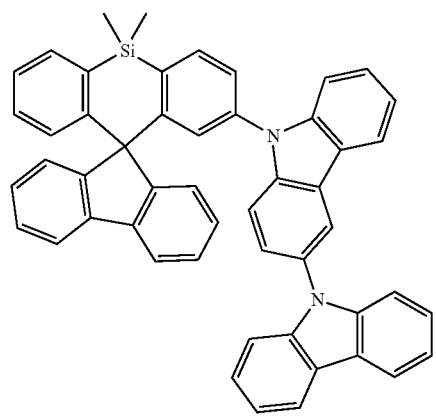
42
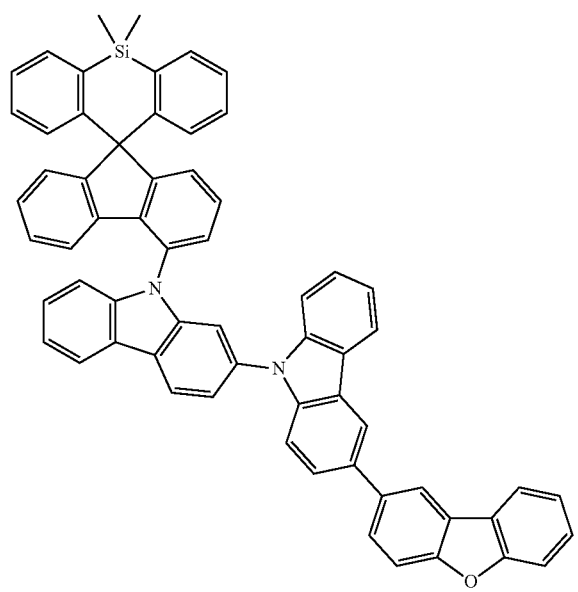
43
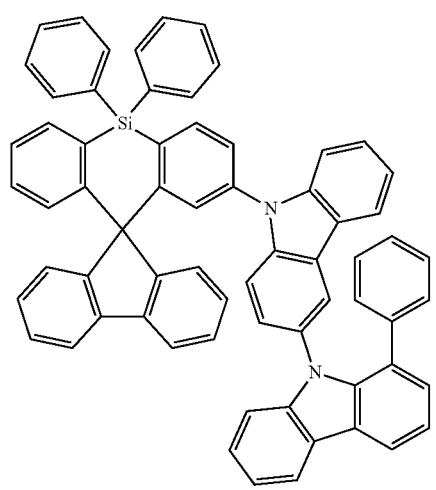
44
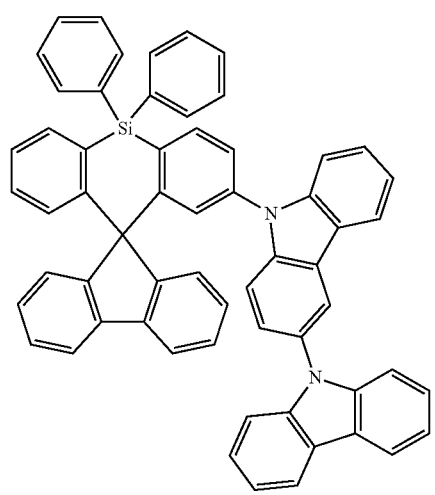

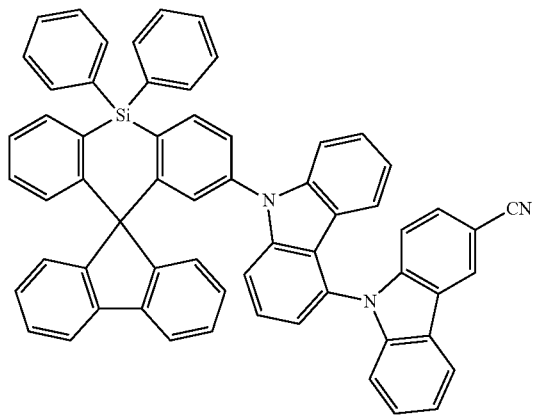

45

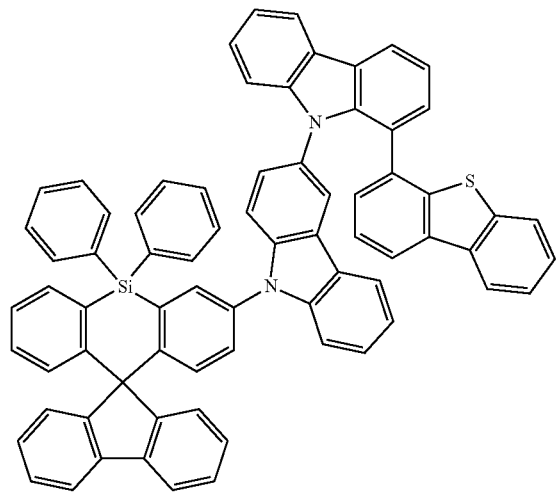

46

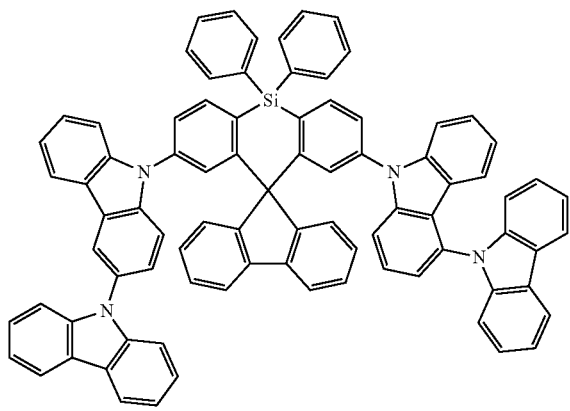

47

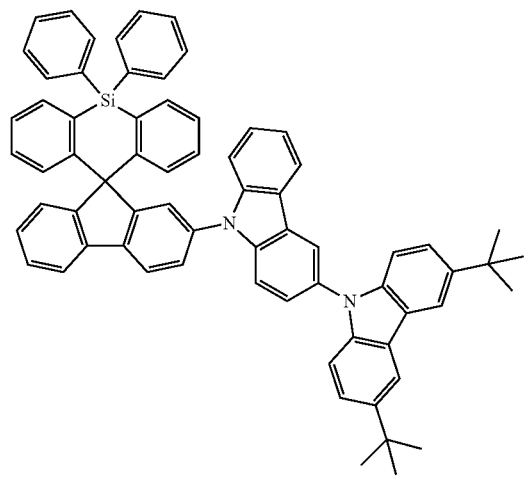

48

In the organic electroluminescence device 10 of an embodiment, the emission layer EML may further include anthracene derivatives, pyrene derivatives, fluoranthene derivatives, chrysene derivatives, dihydrobenzanthracene derivatives, or triphenylene derivatives in addition to the polycyclic compound of an embodiment. Particularly, the emission layer EML may further include anthracene derivatives or pyrene derivatives.

In the organic electroluminescence devices 10 of embodiments as shown in FIG. 1 to FIG. 4, the emission layer EML may include a host and a dopant, and the emission layer EML may include the polycyclic compounds represented by the above-described chemical formulae as host materials. The dopant may include a phosphorescence dopant or a thermally activated delayed fluorescence dopant. However, an embodiment is not limited thereto, and a fluorescence dopant may be included.

The emission layer EML may emit blue light. For example, the emission layer EML may emit blue light having a central wavelength of about 440 nm to about 480 nm.

The emission layer EML may further include commonly used materials well known as the host material in the art. For example, the emission layer EML may include as a host material, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4"-tris (carbazol-9-yl) triphenylamine or 1,3,5-tris(1-phenyl-1H-benzo[d] imidazol-2-yl)benzene (TPBi). However, an embodiment is not limited thereto. For example, tris(8-hydroxyquinolino) aluminum (Alq$_3$), 4,4'-bis(N-carbazolyl)-1,1'-biphenyl (CBP), poly(N-vinylcarbazole) (PVK), 9,10-di(naphthalene-2-yl)anthracene (ADN), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetra siloxane (DPSiO$_4$), 2,8-bis(diphenylphosphoryl)dibenzofuran (PPF), etc. may be used as the host material.

In an embodiment, the emission layer EML may include as the dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl] stilbene (DPAVB), and N-(4-((E)-2-(6-((E)-4-(diphenylamino) styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

In an embodiment, the emission layer EML may include a blue phosphorescence emitting material such as Ir(pmp)$_3$ as the dopant material. Otherwise, a thermally activated delayed fluorescence dopant material emitting blue light may be included. For example, a donor-acceptor type thermally activated delayed fluorescence dopant, or a boron-based thermally activated delayed fluorescence dopant such as DABNA may be included.

In the organic electroluminescence device 10 of an embodiment as shown in FIGS. 1 to 4, the electron transport region ETR is disposed on the emission layer EML. The electron transport region ETR may include at least one of a hole blocking layer HBL, an electron transport layer ETL or an electron injection layer EIL. However, an embodiment is not limited thereto.

The electron transport region ETR may have a single layer formed using a single material, a single layer formed using different materials, or a multilayer structure having layers formed using different materials.

For example, the electron transport region ETR may have a single layer structure of an electron injection layer EIL or an electron transport layer ETL, or a single layer structure formed using an electron injection material and an electron transport material. The electron transport region ETR may have a single layer structure formed using different materials, or a structure stacked from the emission layer EML of electron transport layer ETL/electron injection layer EIL, or hole blocking layer HBL/electron transport layer ETL/electron injection layer EIL, without being limited thereto. The thickness of the electron transport region ETR may be, for example, in a range from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes an electron transport layer ETL, the electron transport region ETR may include an anthracene-based compound. An embodiment is not limited thereto, but the electron transport region ETR may include, for example, tris(8-hydroxyquinolinato)aluminum (Alq3), 1,3,5-tri[(3-pyridyl)-phen-3-yl]benzene, 2,4,6-tri s(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazol e (tBu-PBD), bis(2-methyl-8-quinolinolato-N1,O8)-(1,1'-biphenyl-4-olato) aluminum (BAlq), berylliumbis(benzoquinolin-10-olate (Bebq$_2$), 9,10-di(naphthalene-2-yl)anthracene (ADN), 1,3-bis[3,5-di(pyridine-3-yl)phenyl]benzene (BmPyPhB), or a mixture thereof. The thickness of the electron transport layer ETL may be in a range from about 100 Å to about 1,000 Å. In an embodiment, the thickness of the electron transport layer ETL may be in a range from about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may use a metal halide such as LiF, NaCl, CsF, RbCl and RbI, a metal in lanthanoides such as Yb, a metal oxide such as Li$_2$O and BaO, or lithium quinolate (LiQ). However, an embodiment is not limited thereto. The electron injection layer EIL may also be formed using a mixture material of an electron transport material and an insulating organo metal salt. The organo metal salt may be a material having an energy band gap of about 4 eV or more. Particularly, the organo metal salt may include, for example, metal acetates, metal benzoates, metal acetoacetates, metal acetylacetonates, or metal stearates. The thickness of the electron injection layer EIL may be in a range from about 1 Å to about 100 Å. In an embodiment, the thickness of the electron injection layer EIL may be in a range from about 3 Å to about 90 Å. If the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, an embodiment is not limited thereto.

The second electrode EL2 is disposed on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may be formed using a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

Though not shown, the second electrode EL2 may be electrically connected with an auxiliary electrode. If the second electrode EL2 is electrically connected with the auxiliary electrode, the resistance of the second electrode EL2 may decrease.

On the second electrode EL2 of the organic electroluminescence device 10 of an embodiment, a capping layer CPL may be disposed. The capping layer CPL may include, for example, α-NPD, NPB, TPD, m-MTDATA, Alq$_3$, CuPc, N4,N4,N4',N4'-tetra(biphenyl-4-yl) biphenyl-4,4'-diamine (TPD15), 4,4',4"-tris(carbazol-9-yl)triphenylamine (TCTA), N,N'-bis(naphthalen-1-yl), etc.

The above-described polycyclic compound of an embodiment may be included in a functional layer other than the hole transport region HTR as a material for the organic electroluminescence device 10. The organic electroluminescence device 10 according to an embodiment may include the above-described compound in at least one functional layer disposed between the first electrode EL1 and the second electrode EL2, or in the capping layer CPL disposed on the second electrode EL2.

Hereinafter, the polycyclic compound according to an embodiment and the organic electroluminescence device of an embodiment will be particularly explained referring to embodiments and comparative embodiments. The following embodiments are only illustrations to assist the understanding of the invention, and the scope of the invention is not limited thereto.

The polycyclic compound according to an embodiment may be synthesized, for example, by the following. However, the synthetic method of the polycyclic compound according to an embodiment is not limited thereto.

1-1. Synthesis of Compound 2

Polycyclic Compound 2 of an embodiment may be synthesized, for example, by the following Reaction 1:

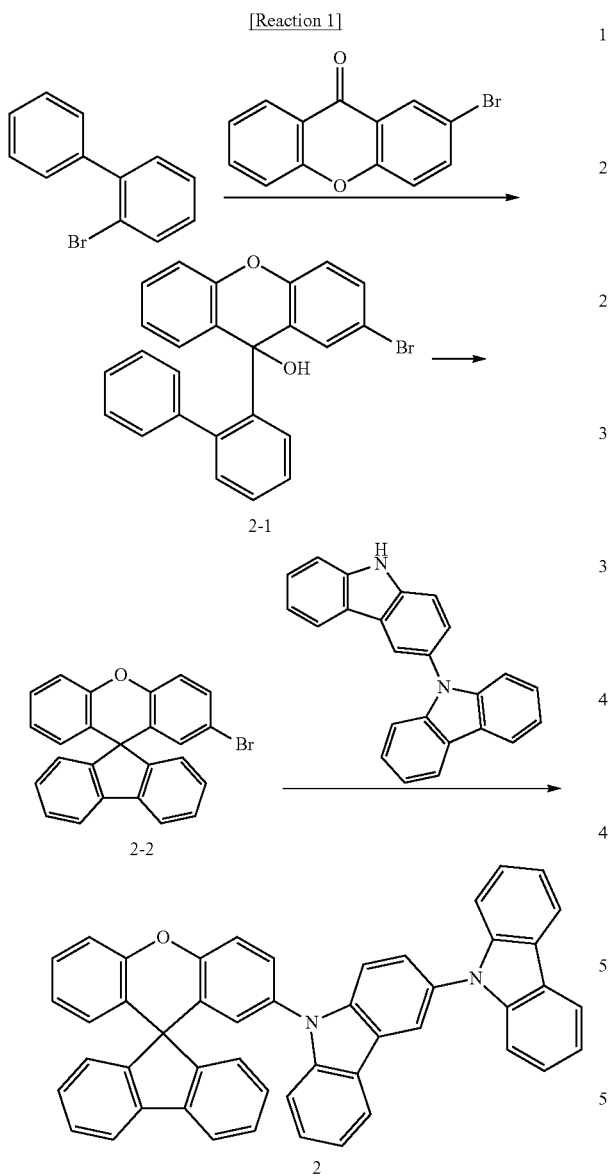

(Synthesis of Intermediate 2-1)

After reacting 2-bromo-1,1'-biphenyl (CAS Number=2052-07-5) with n-BuLi, the resultant product was reacted with 2-bromo-9H-xanthene-9-one (CAS Number=56341-31-2) to obtain Intermediate 2-1. The M+1 peak value of Intermediate 2-1 was found using liquid chromatography mass spectrometry (LC-MS).

$C_{25}H_{17}BrO_2$: M+1 429.12

(Synthesis of Intermediate 2-2)

By reacting Intermediate 2-1 with hydrochloric acid, Intermediate 2-2 was obtained. The M+1 peak value of Intermediate 2-2 was found using liquid chromatography mass spectrometry (LC-MS).

$C_{25}H_{15}BrO$: M+1 410.06

(Synthesis of Compound 2)

5 g of Intermediate 2-2, 4 g of 9H-3,9'-bicarbazole, 1.8 g of sodium tert-butoxide, 0.45 g of tris(dibenzylideneacetone)dipalladium(0), 0.4 ml of tri-tert-butylphosphine, and 60 ml of toluene were put to a reaction vessel, followed by refluxing for about 24 hours. After finishing the reaction, the reaction solution was extracted with ethyl acetate, organic layers collected were dried with magnesium sulfate, and solvents were evaporated. The residue thus obtained was separated and purified by silica gel column chromatography to obtain 6.4 g (Yield: 80%) of Compound 2. Compound 2 was identified by LC-MS and $^1$H-NMR.

1-2. Synthesis of Compound 3

Polycyclic Compound 3 of an embodiment may be synthesized, for example, by the following Reaction 2:

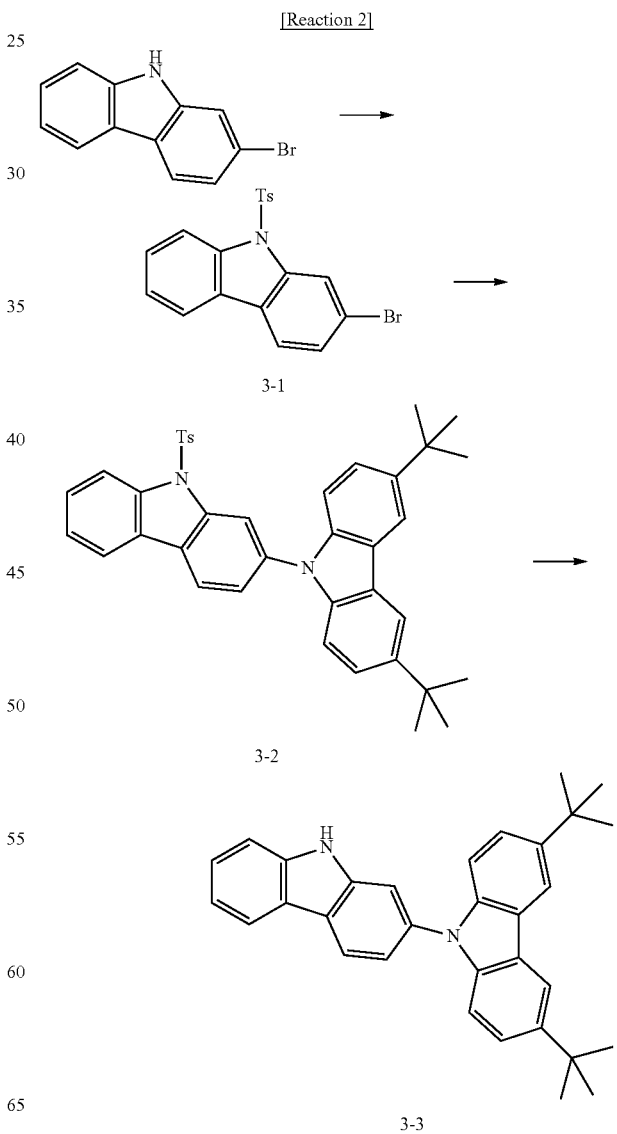

-continued

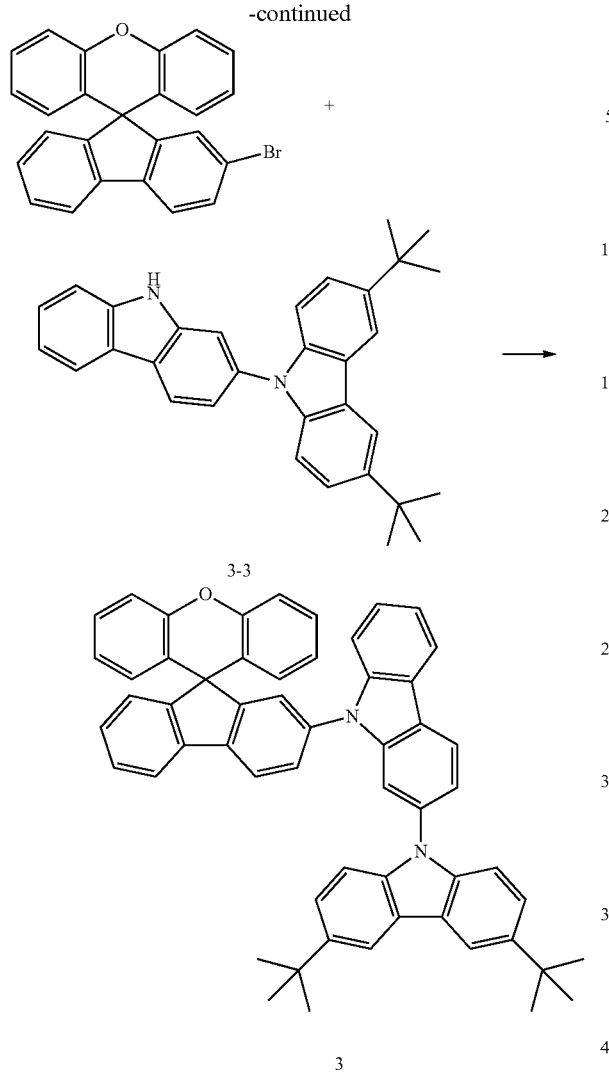

(Synthesis of Intermediate 3-1)

Intermediate 3-1 was obtained by reacting 2-bromo-9H-carbazole (CAS Number=864550-95-8), potassium hydroxide, and 4-toluenesulfonyl chloride. The M+1 peak value of Intermediate 3-1 was found using liquid chromatography mass spectrometry (LC-MS).

$C_{19}H_{14}BrNO_2S$: M+1 399.97

(Synthesis of Intermediate 3-2)

By reacting Intermediate 3-1 with 3,6-di-tert-butylcarbazole (CAS Number=37500-95-1) in Pd catalyst conditions, Intermediate 3-2 was obtained. The M+1 peak value of Intermediate 3-2 was found using liquid chromatography mass spectrometry (LC-MS).

$C_{39}H_{38}N_2O_2S$: M+1 599.31

(Synthesis of Intermediate 3-3)

By reacting Intermediate 3-2 with sodium hydroxide, Intermediate 3-3 was obtained. The M+1 peak value of Intermediate 3-3 was found using liquid chromatography mass spectrometry (LC-MS).

$C_{32}H_{32}N_2$: M+1 444.17

(Synthesis of Compound 3)

Compound 3 was synthesized by the same method as the synthetic procedure of Compound 2 except for using 2-bromo spiro[9H-fluoren-9,9'-[9H]xanthene] (CAS Number=899422-06-1) instead of Intermediate 2-2 and using Intermediate 3-3 instead of 9H-3,9'-bicarbazole. 5.5 g (Yield: 73%) was obtained. Compound 3 was identified by LC-MS and $^1$H-NMR.

1-3. Synthesis of Compound 6

Polycyclic Compound 6 of an embodiment may be synthesized, for example, by the following Reaction 3:

[Reaction 3]

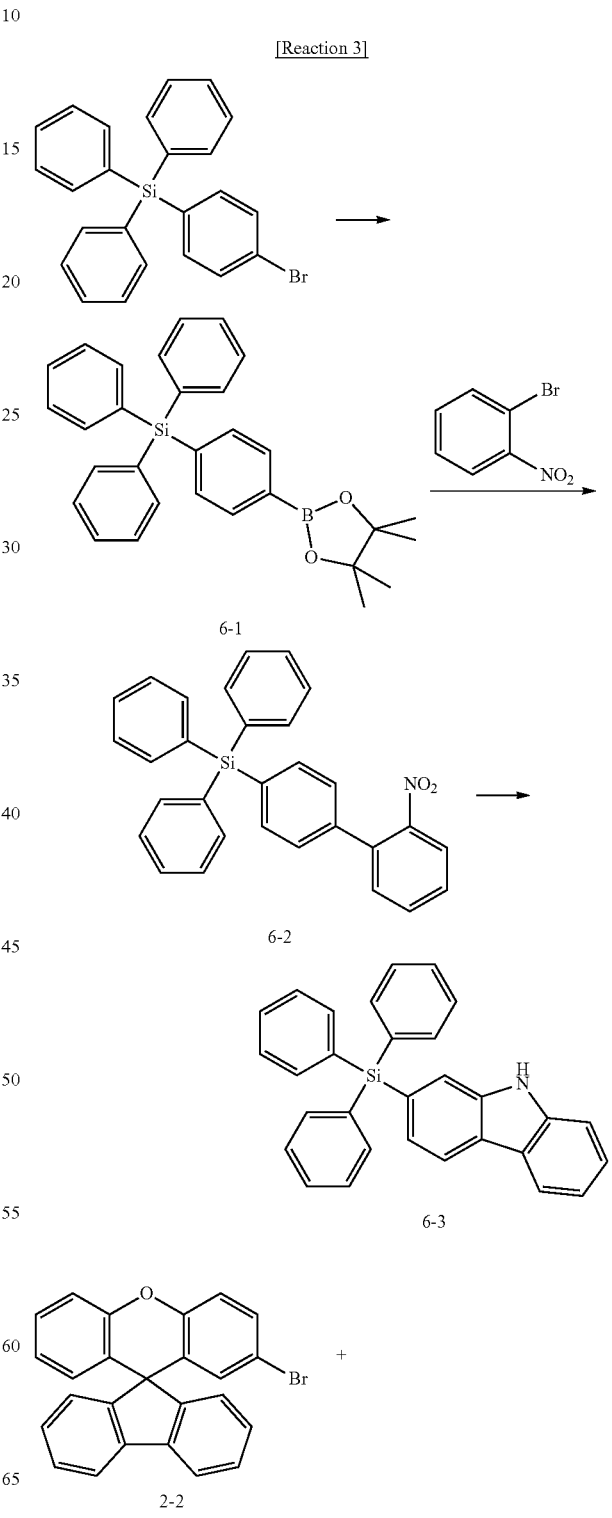

1-4. Synthesis of Compound 13

Polycyclic Compound 13 of an embodiment may be synthesized, for example, by the following Reaction 4:

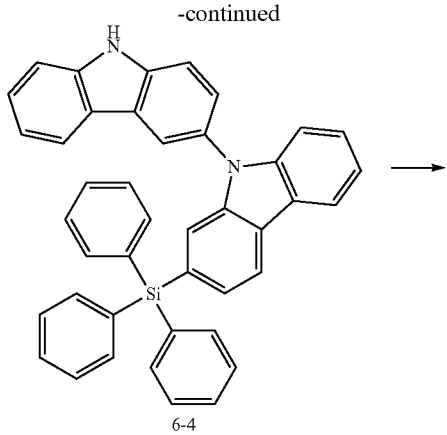

6-4

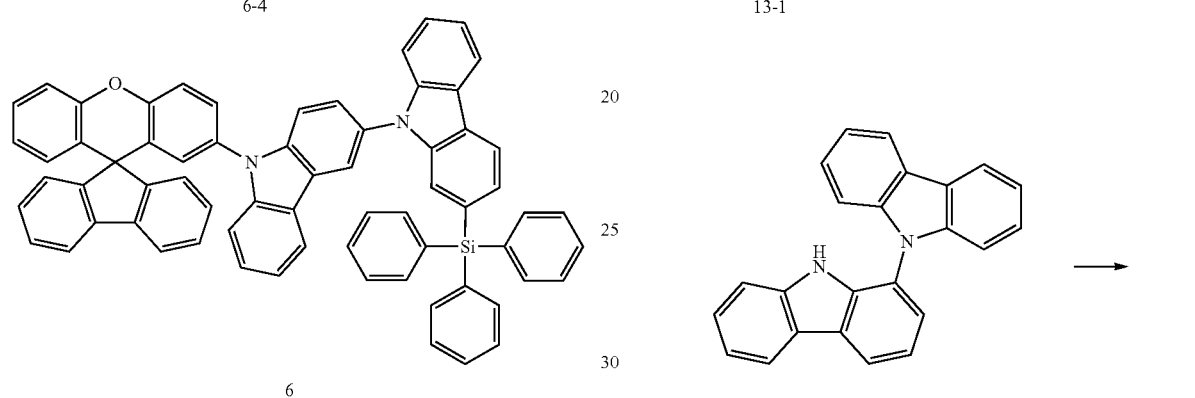

6

(Synthesis of Intermediate 6-1)

Intermediate 6-1 was obtained by reacting (4-bromophenyl)triphenylsilane (CAS Number=18737-40-1) and bis(pinacolato)diboron in Pd catalyst conditions. The M+1 peak value of Intermediate 6-1 was found using liquid chromatography mass spectrometry (LC-MS).

$C_{30}H_{31}BO_2Si$: M+1 463.24

(Synthesis of Intermediate 6-2)

By reacting Intermediate 6-1 with 1-bromo-2-nitrobenzene (CAS Number=577-19-5) in Pd catalyst conditions, Intermediate 6-2 was obtained. The M+1 peak value of Intermediate 6-2 was found using liquid chromatography mass spectrometry (LC-MS).

$C_{30}H_{23}NO_2Si$: M+1 458.03

(Synthesis of Intermediate 6-3)

By reacting Intermediate 6-2 with triphenylphosphine (CAS number=603-35-0), Intermediate 6-3 was obtained. The M+1 peak value of Intermediate 6-3 was found using liquid chromatography mass spectrometry (LC-MS).

$C_{30}H_{23}NSi$: M+1 426.26

(Synthesis of Intermediate 6-4)

Intermediate 6-4 was obtained by the same synthetic procedure of Intermediate 3-3 except for using 3-bromo-9-tosyl-9H-carbazole instead of Intermediate 3-1 and using Intermediate 6-3 instead of 3,6-di-tert-butylcarbazole. The M+1 peak value of Intermediate 6-4 was found using liquid chromatography mass spectrometry (LC-MS).

$C_{42}H_{30}N_2Si$: M+1 591.11

(Synthesis of Compound 6)

Compound 6 was synthesized by the same method as the synthetic procedure of Compound 2 except for using Intermediate 6-4 instead of 9H-3,9'-bicarbazole. 6.2 g (Yield: 70%) was obtained. Compound 6 was identified by LC-MS and $^1$H-NMR.

[Reaction 4]

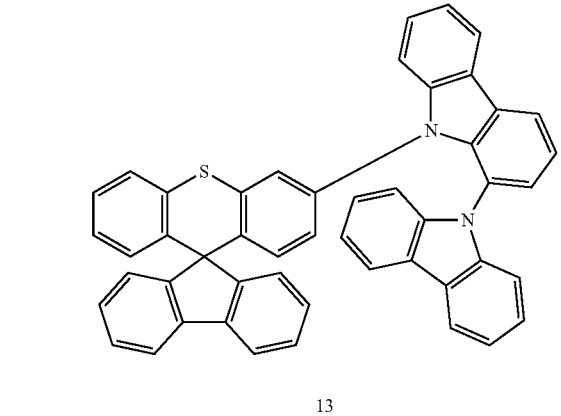

13-1

13

(Synthesis of Intermediate 13-1)

Intermediate 13-1 was obtained by the same synthetic procedure of Intermediate 2-2 except for using 3-bromo-9H-thioxanthene-9-one (CAS Number=96407-89-5) instead of 2-bromo-9H-xanthene-9-one. The M+1 peak value of Intermediate 13-1 was found using liquid chromatography mass spectrometry (LC-MS).

$C_{25}H_{15}BrS$: M+1 427.01

(Synthesis of Compound 13)

Compound 13 was synthesized by the same method as the synthetic procedure of Compound 2 except for using Intermediate 13-1 instead of Intermediate 2-2 and using 9H-1,9'-bicarbazole (CAS Number=27825-35-0) instead of 9H-3,9'-bicarbazole. 3.5 g (Yield: 45%) was obtained. Compound 13 was identified by LC-MS and $^1$H-NMR.

1-5. Synthesis of Compound 15

Polycyclic Compound 15 of an embodiment may be synthesized, for example, by the following Reaction 5:

[Reaction 5]

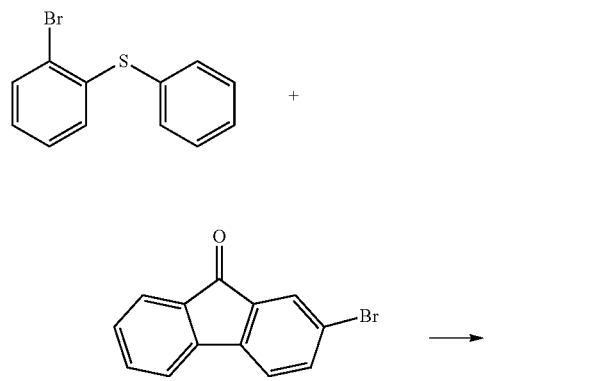

15-1

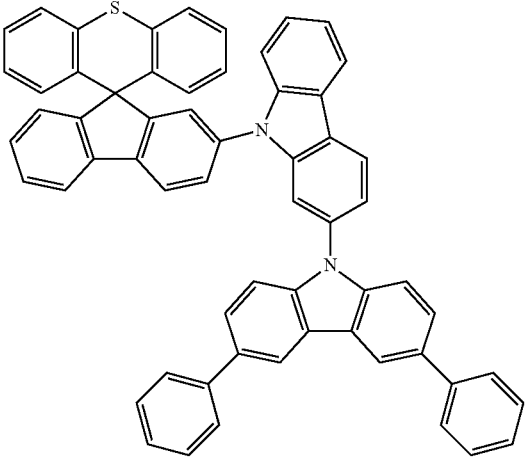

15

(Synthesis of Intermediate 15-1)

By reacting 1-bromo-2-(phenylthiol)benzene (CAS Number=15861-48-0) with n-BuLi and then reacting the resultant product with 2-bromo-9H-fluoren-9-one (CAS Number=3096-56-8), Intermediate 15-1 was obtained. The M+1 peak value of Intermediate 15-1 was found using liquid chromatography mass spectrometry (LC-MS).

$C_{25}H_{15}BrS$: M+1 427.33

(Synthesis of Intermediate 15-2)

Intermediate 15-2 was obtained by the same synthetic procedure of Intermediate 3-3 except for using 3,6-diphenyl-9H-carbazole (CAS Number=56525-79-2) instead of 3,6-di-tert-butylcarbazole. The M+1 peak value of Intermediate 15-2 was found using liquid chromatography mass spectrometry (LC-MS).

$C_{36}H_{24}N_2$: M+1 485.1

(Synthesis of Compound 15)

Compound 15 was synthesized by the same method as the synthetic procedure of Compound 2 except for using Intermediate 15-1 instead of Intermediate 2-2 and using Intermediate 15-2 instead of 9H-3,9'-bicarbazole. 5.2 g (Yield: 67%) was obtained. Compound 15 was identified by LC-MS and $^1$H-NMR.

1-6. Synthesis of Compound 19

Polycyclic Compound 19 of an embodiment may be synthesized, for example, by the following Reaction 6:

[Reaction 6]

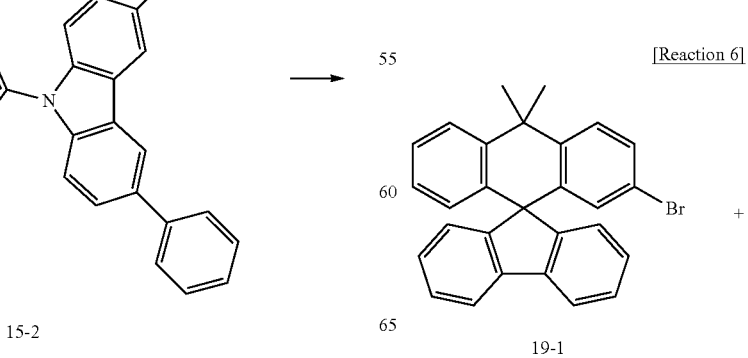

19-1

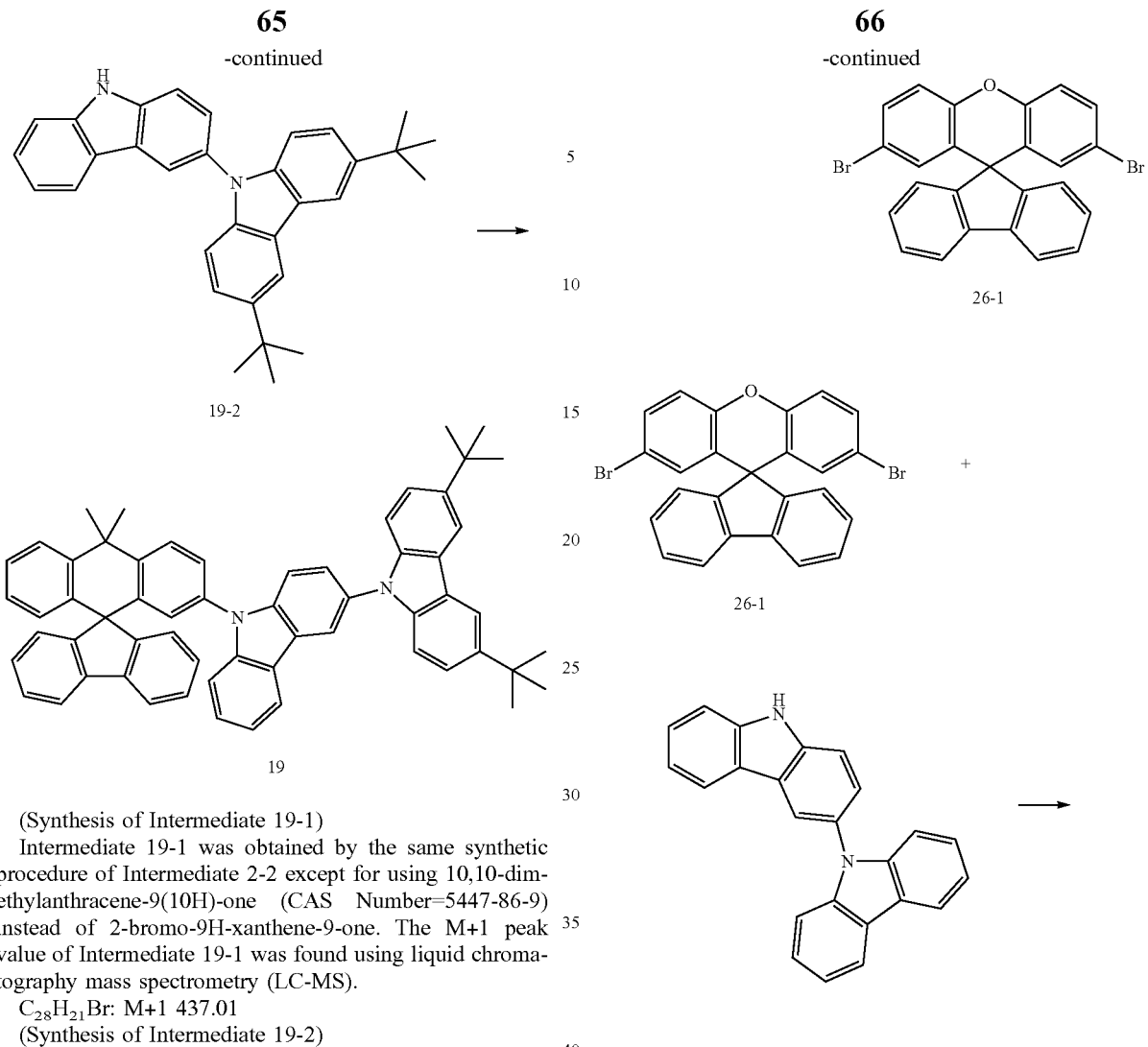

(Synthesis of Intermediate 19-1)

Intermediate 19-1 was obtained by the same synthetic procedure of Intermediate 2-2 except for using 10,10-dimethylanthracene-9(10H)-one (CAS Number=5447-86-9) instead of 2-bromo-9H-xanthene-9-one. The M+1 peak value of Intermediate 19-1 was found using liquid chromatography mass spectrometry (LC-MS).

$C_{28}H_{21}Br$: M+1 437.01

(Synthesis of Intermediate 19-2)

Intermediate 19-2 was obtained by the same synthetic procedure of Intermediate 3-3 except for using 3-bromo-9H-carbazole (CAS Number=1592-95-6) instead of 2-bromo-9H-carbazole. The M+1 peak value of Intermediate 19-2 was found using liquid chromatography mass spectrometry (LC-MS).

$C_{32}H_{32}N_2$: M+1 445.22

(Synthesis of Compound 19)

Compound 19 was synthesized by the same method as the synthetic procedure of Compound 2 except for using Intermediate 19-1 instead of Intermediate 2-2 and using Intermediate 19-2 instead of 9H-3,9'-bicarbazole. 6.2 g (Yield: 85%) was obtained. Compound 19 was identified by LC-MS and $^1$H-NMR.

1-7. Synthesis of Compound 26

Polycyclic Compound 26 of an embodiment may be synthesized, for example, by the following Reaction 7:

[Reaction 7]

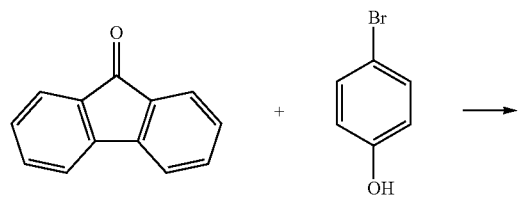

(Synthesis of Intermediate 26-1)

Intermediate 26-1 was obtained by reacting 9H-fluorenone (CAS Number=486-25-9) and 4-bromophenol (CAS Number=106-41-2). The M+1 peak value of Intermediate 26-1 was found using liquid chromatography mass spectrometry (LC-MS).

$C_{25}H_{14}Br_2O$: M+1 488.97

(Synthesis of Compound 26)

Compound 26 was synthesized by the same method as the synthetic procedure of Compound 2 except for using Intermediate 26-1 instead of Intermediate 2-2. 4.7 g (Yield: 78%) was obtained. Compound 26 was identified by LC-MS and $^1$H-NMR.

1-8. Synthesis of Compound 30

Polycyclic Compound 30 of an embodiment may be synthesized, for example, by the following Reaction 8:

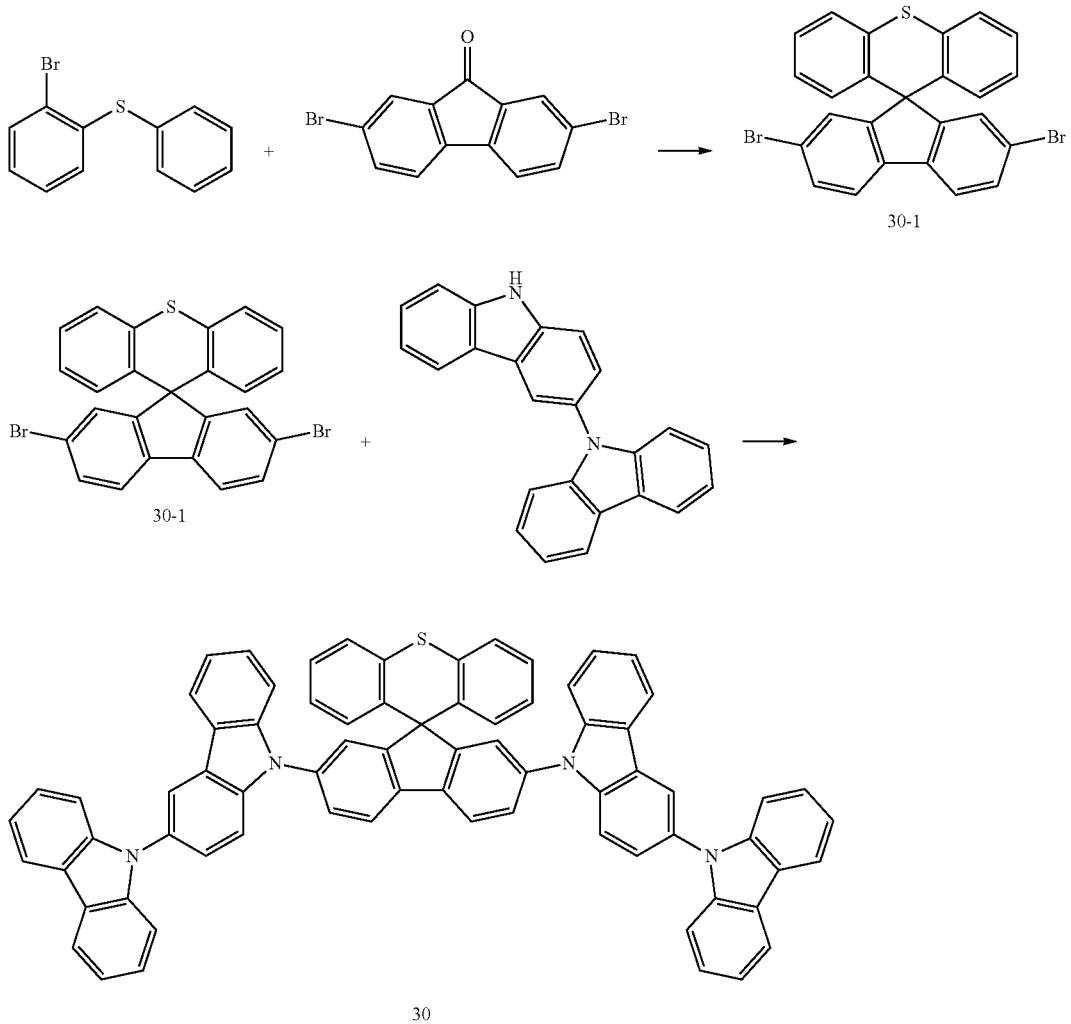

(Synthesis of Intermediate 30-1)

Intermediate 30-1 was synthesized by the same method as the synthetic procedure of Intermediate 15-1 except for using 2,7-dibromo-9H-fluorene-9-one (CAS Number=14348-75-5) instead of 2-bromo-9H-fluoren-9-one. The M+1 peak value of Intermediate 30-1 was found using liquid chromatography mass spectrometry (LC-MS).

$C_{25}H_{14}Br_2S$: M+1 504.78

(Synthesis of Compound 30)

Compound 30 was synthesized by the same method as the synthetic procedure of Compound 2 except for using Intermediate 30-1 instead of Intermediate 2-2. 4.5 g (Yield: 77%) was obtained. Compound 30 was identified by LC-MS and $^1$H-NMR.

1-9. Synthesis of Compound 37

Polycyclic Compound 37 of an embodiment may be synthesized, for example, by the following Reaction 9:

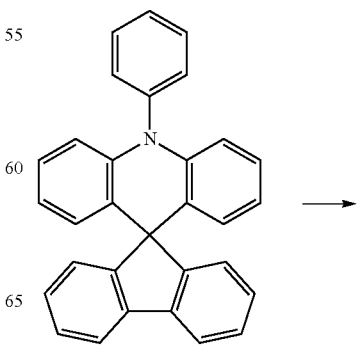

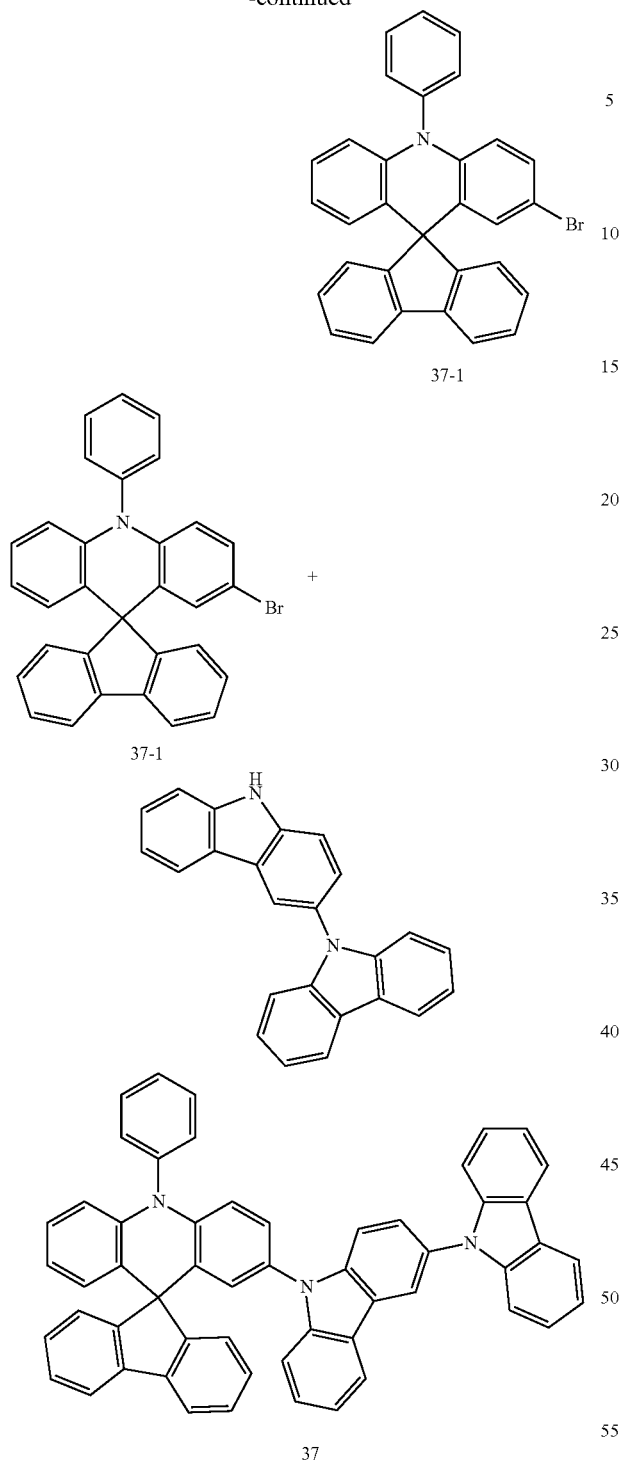

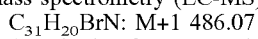

37

(Synthesis of Intermediate 37-1)
Intermediate 37-1 was synthesized by reacting 10-phenyl-10H-spiro[acridine-9,9'-fluorene] (CAS Number=1206626-92-7) with N-bromosuccinimide. The M+1 peak value of Intermediate 37-1 was found using liquid chromatography mass spectrometry (LC-MS).
$C_{31}H_{20}BrN$: M+1 486.07
(Synthesis of Compound 37)
Compound 37 was synthesized by the same method as the synthetic procedure of Compound 2 except for using Intermediate 37-1 instead of Intermediate 2-2. 5 g (Yield: 83%) was obtained. Compound 37 was identified by LC-MS and $^1$H-NMR.

1-10. Synthesis of Compound 43

Polycyclic Compound 43 of an embodiment may be synthesized, for example, by the following Reaction 10:

[Reaction 10]

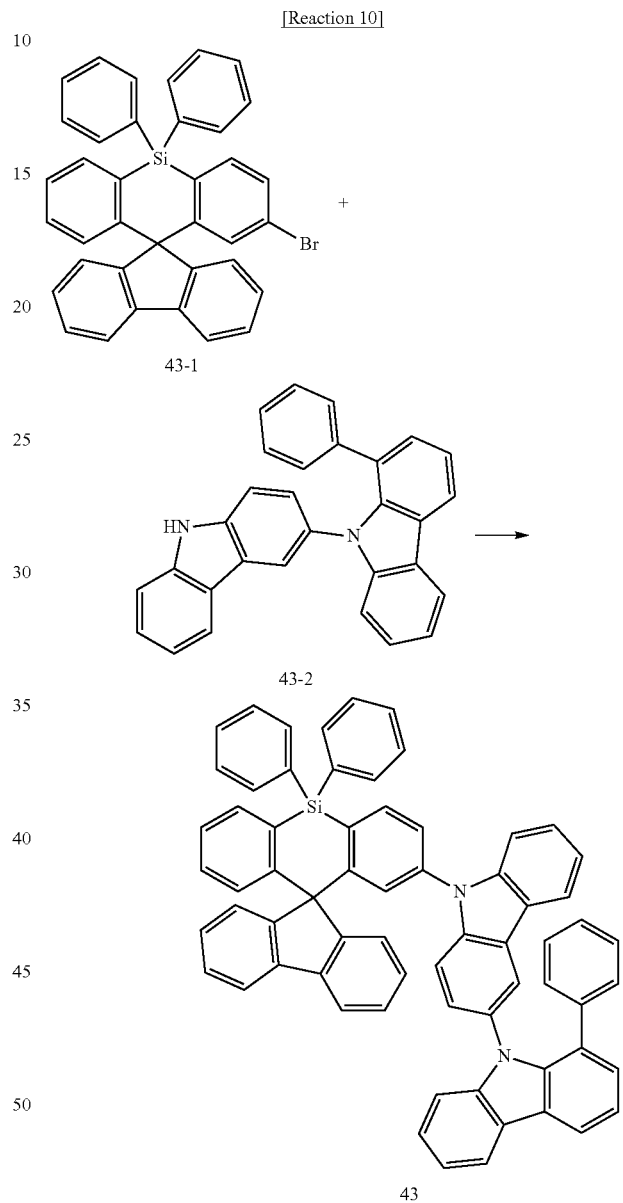

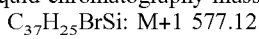

(Synthesis of Intermediate 43-1)
Intermediate 43-1 was obtained by the same method as the synthetic procedure of Intermediate 2-2 except for using 5,5-diphenyl dibenzo[b,e]siline-10(5H)-on (CAS Number=53689-83-1) instead of 2-bromo-9H-xanthene-9-one. The M+1 peak value of Intermediate 43-1 was found using liquid chromatography mass spectrometry (LC-MS).
$C_{37}H_{25}BrSi$: M+1 577.12
(Synthesis of Intermediate 43-2)
Intermediate 43-2 was synthesized by the same method as the synthetic procedure of Intermediate 19-2 except for using 1-phenyl-9H-carbazole (CAS Number=104636-53-5)

instead of 3,6-di-tert-butylcarbazole. The M+1 peak value of Intermediate 43-2 was found using liquid chromatography mass spectrometry (LC-MS).

$C_{30}H_{20}N_2$: M+1 489.16

(Synthesis of Compound 43)

Compound 43 was synthesized by the same method as the synthetic procedure of Compound 2 except for using Intermediate 43-1 instead of Intermediate 2-2 and using Intermediate 43-2 instead of 9H-3,9'-bicarbazole. 3.3 g (Yield: 70%) was obtained. Compound 43 was identified by LC-MS and $^1$H-NMR.

$^1$H NMR and LC-MS data of the compounds synthesized in the Synthetic Examples are shown in Table 1 below.

A person skilled in the art could easily synthesize compounds other than the compounds shown in Table 1 referring to the synthetic procedure and raw materials above.

TABLE 1

| Compound | $^1$H NMR (CDCl3, 400 MHz) | LC-MS Found [M + 1] | calc. |
|---|---|---|---|
| 2 | 8.55 (2H, d), 8.19 (1H, d), 7.94-7.90 (4H, m), 7.74-7.67 (3H, m), 7.57-7.50 (5H, m), 7.38-7.13 (14H, m), 7.01 (1H, d) | 663.12 | 662.24 |
| 3 | 8.95 (1H, s), 8.55 (1H, d), 8.36 (1H, s), 8.26 (1H, d), 8.04 (1H, d), 7.90-7.86 (3H, m), 7.67-7.62 (2H, m), 7.55-7.50 (4H, m), 7.38-7.28 (6H, m), 7.17-7.11 (6H, m), 7.01 (2H, t), 1.43 (18H, s) | 775.44 | 774.36 |
| 6 | 8.55 (2H, d), 8.22 (1H, d), 7.94-7.90 (4H, q), 7.72-7.67 (4H, m), 7.59-7.55 (3H, m), 7.46-7.28 (24H, m), 7.17-7.13 (5H, m), 7.01 (1H, t) | 921.36 | 920.32 |
| 13 | 8.55 (2H, d), 8.19-8.15 (2H, q), 7.94-7.90 (4H, q), 7.69 (1H, d), 7.58-7.16 (18H, m), 7.03-6.98 (3H, m) | 679.24 | 678.21 |
| 15 | 8.55 (1H, d), 8.30-8.26 (2H, q), 8.13 (1H, d), 8.04-7.89 (6H, m), 7.77-7.67 (8H, m), 7.55-7.28 (15H, m), 7.16 (1H, t), 7.03-6.98 (4H, m) | 831.19 | 830.28 |
| 19 | 8.95 (1H, s), 8.55 (1H, d), 8.36 (1H, s), 7.94-7.86 (4H, m), 7.72-7.67 (3H, m), 7.50-7.27 (14H, m), 7.19-7.11 (4H, m), 1.69 (6H, s), 1.43 (18H, s) | 801.44 | 800.41 |
| 26 | 8.55 (4H, d), 8.19 (2H, d), 7.94-7.90 (6H, m), 7.74-7.50 (14H, m), 7.38-7.16 (18H, m) | 993.42 | 992.35 |
| 30 | 8.55 (4H, d), 8.19 (2H, d), 8.04 (2H, d), 7.94 (4H, d), 7.72-7.67 (8H, m), 7.58-7.56 (6H, m), 7.38-7.33 (8H, m), 7.20-7.16 (6H, m), 7.03-6.98 (4H, m) | 1009.23 | 1008.33 |
| 37 | 8.55 (2H, d), 8.19 (1H, d), 7.94-7.90 (4H, m), 7.74-7.67 (3H, m), 7.59-7.50 (5H, m), 7.38-6.95 (20H, m) | 738.32 | 737.28 |
| 43 | 8.55 (2H, d), 8.29 (1H, d), 8.06 (1H, d), 7.94-7.88 (5H, m), 7.73-7.67 (3H, m), 7.48-7.16 (32H, m) | 905.11 | 904.33 |

2. Manufacture and Evaluation of Organic Electroluminescence Device Including Polycyclic Compound 2-1. Examples of Organic Electroluminescence Devices Including Polycyclic Compound Organic electroluminescence devices of Examples 1 to 10 and Comparative Examples 1 to 4 were manufactured using Example Compounds 2, 3, 6, 13, 15, 19, 26, 30, 37 and 43 and Comparative Compounds C1 to C4 as the host materials of emission layers EML, respectively.

(Example Compounds)

2

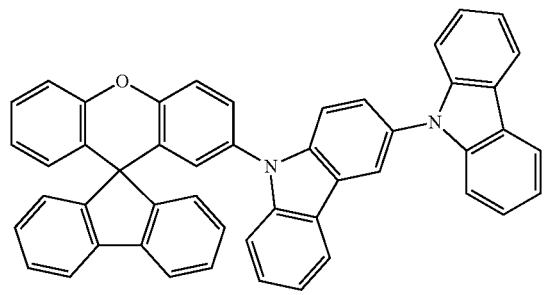

3

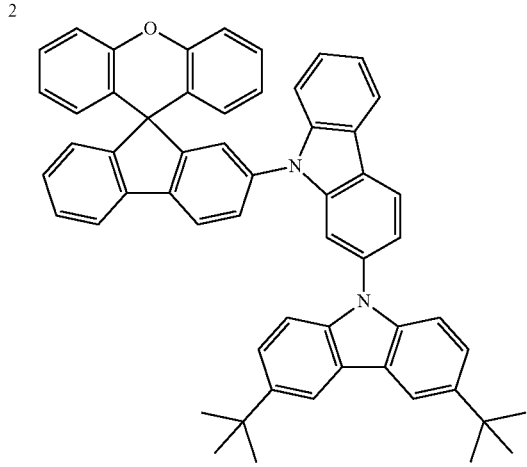

-continued
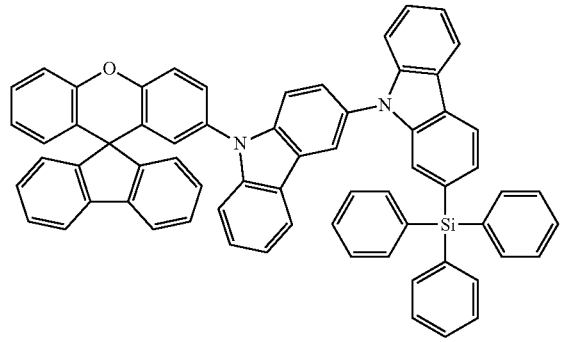
6
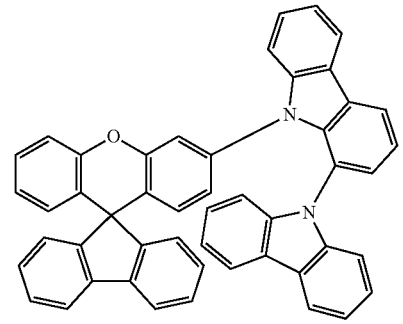
13
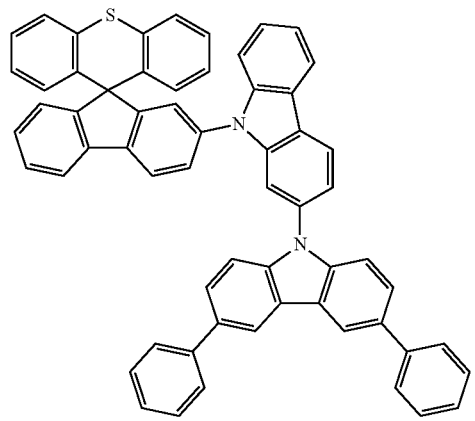
15
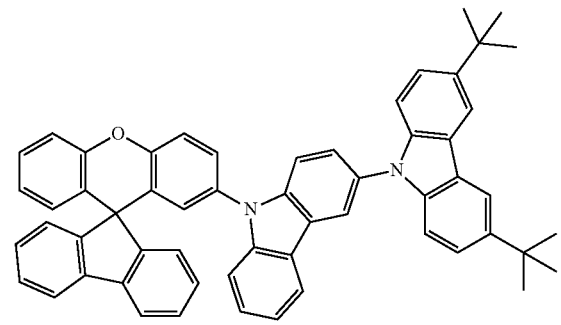
19
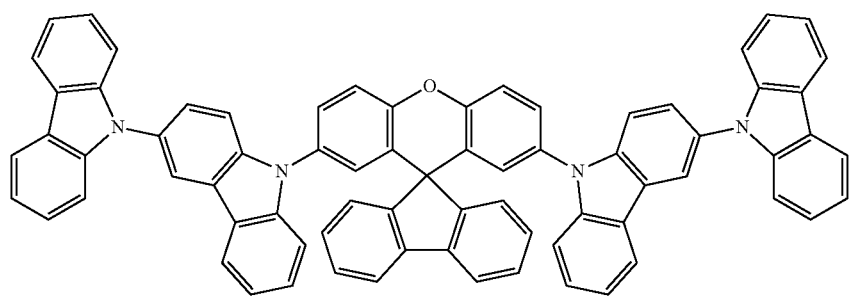
26
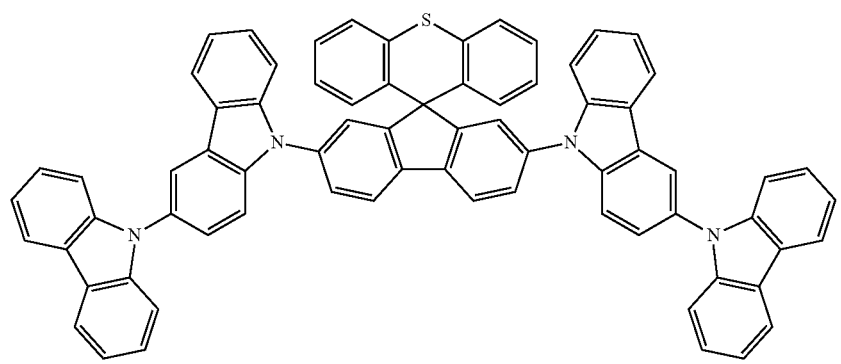
30

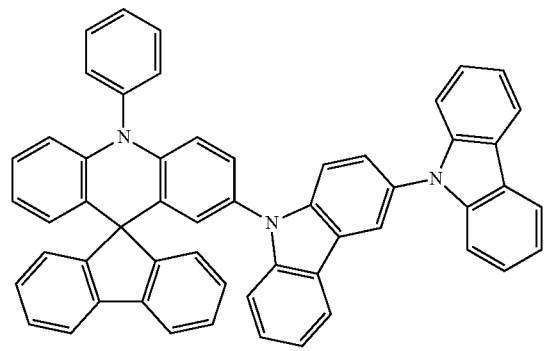
37
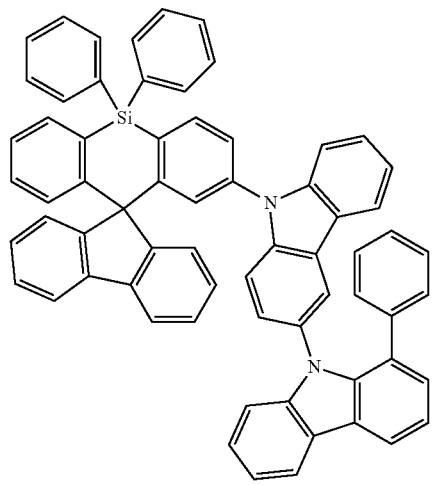
43
(Comparative Compounds)
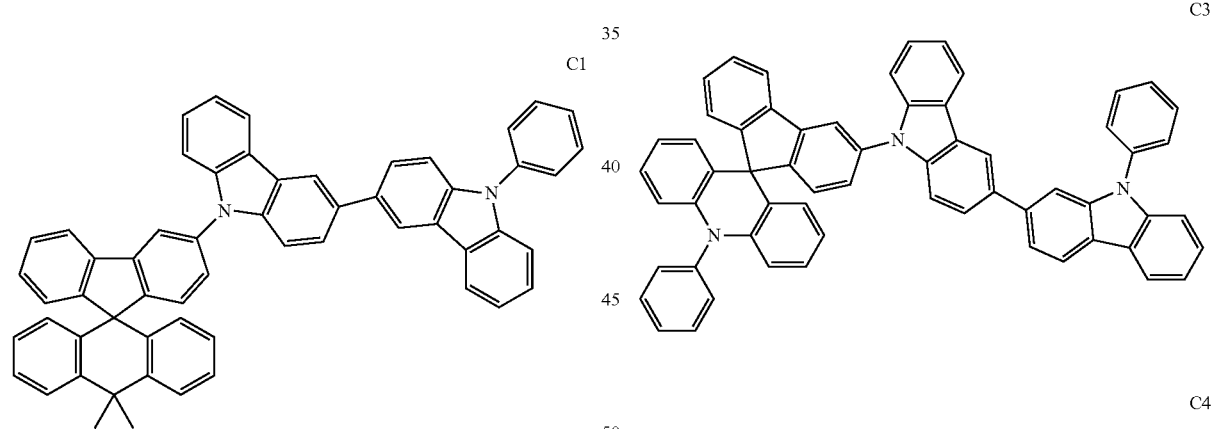
C1
C2
C3
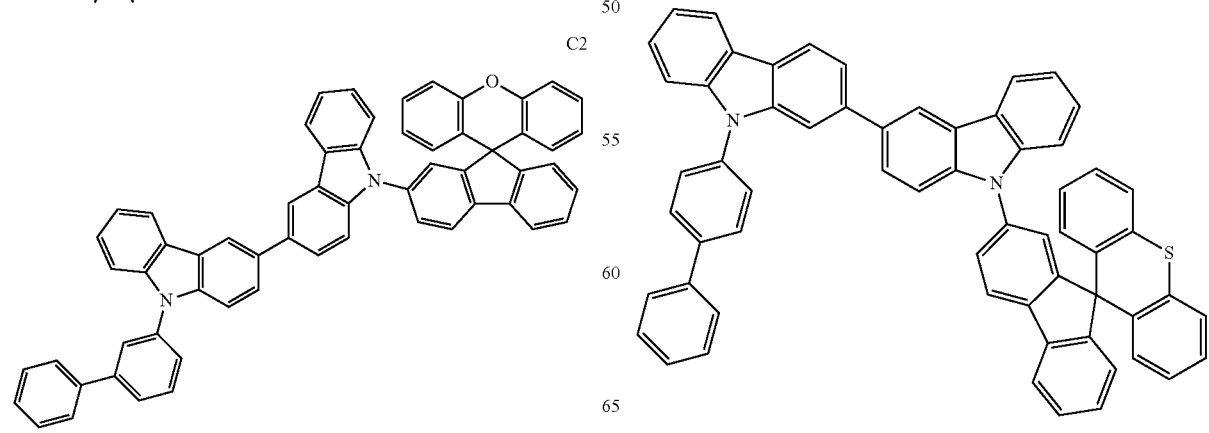
C4

(Compounds of Functional Layers)

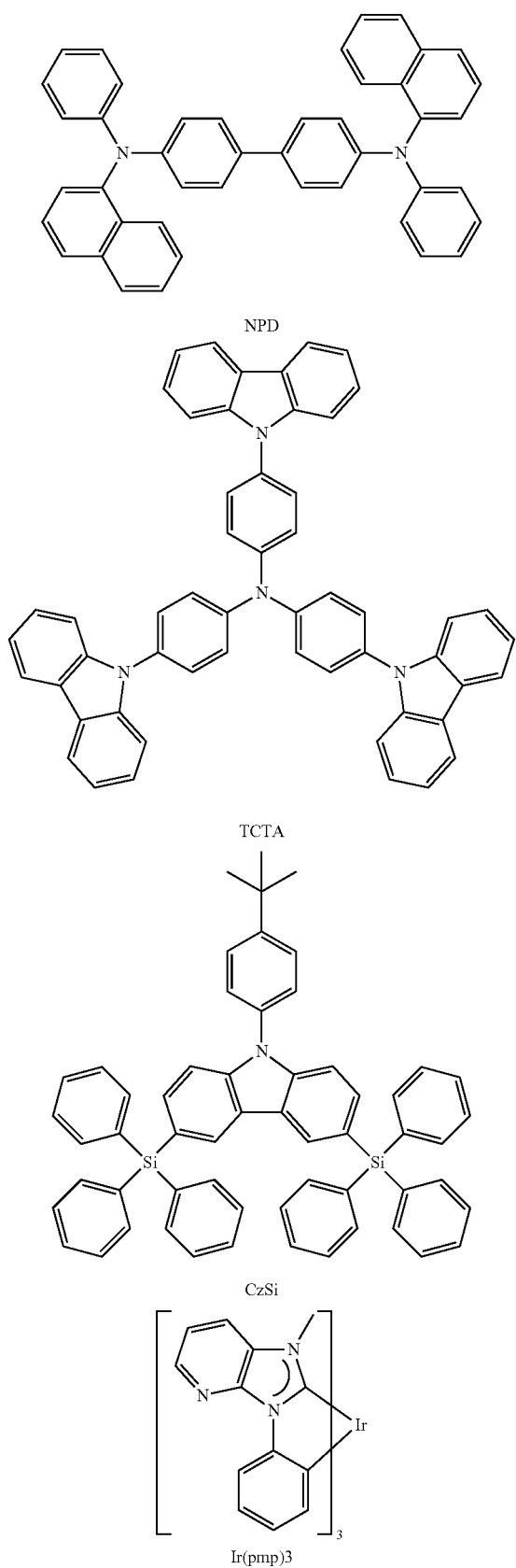

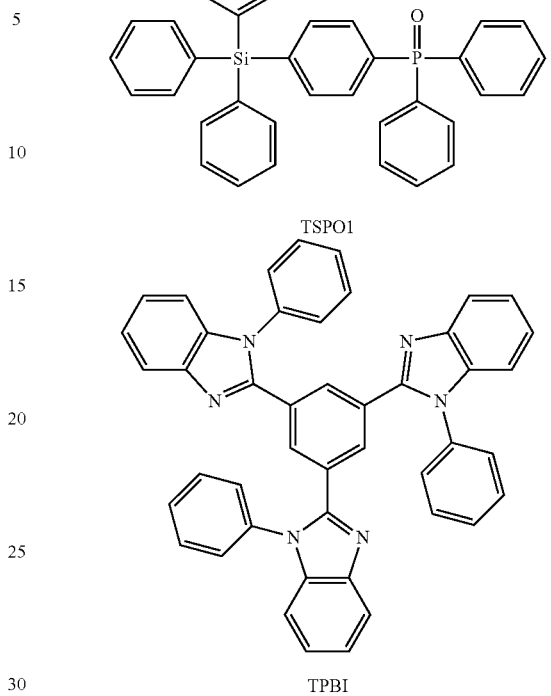

(Manufacture of Organic Electroluminescence Device)

Each of the organic electroluminescence devices of Examples 1 to 10 and Comparative Examples 1 to 4 was manufactured as follows. A glass substrate of ITO (Corning Co.) was cut into a size of about 50 mm×50 mm×0.7 mm, washed by ultrasonic waves using isopropyl alcohol and distilled water for 5 minutes, respectively, and washed by exposing to ultraviolet light and then ozone for about 30 minutes to form a first electrode EL1 with a thickness of about 1,200 Å in a vacuum deposition apparatus. A hole injection layer HIL was formed using NPD to a thickness of about 300 Å. A hole transport layer HTL was formed by depositing TCTA to a thickness of about 200 Å and an electron blocking layer EBL was formed by depositing CzSi to a thickness of about 100 Å. An emission layer EML was formed using each of the Example Compounds or the Comparative Compounds doped with 8% Ir(pmp)$_3$ to a thickness of about 250 Å, a hole blocking layer HBL was formed using diphenyl[4-(triphenylsilyl)phenyl]phosphine oxide (TSPO1) to a thickness of about 200 Å, and an electron transport layer ETL was formed using TBPi to a thickness of about 300 Å. An electron injection layer EIL with a thickness of about 10 Å was formed using LiF, and a second electrode EL2 with a thickness of about 3,000 Å was formed using Al. Each layer was formed by a vacuum deposition method.

(Evaluation of Properties of Organic Electroluminescence Devices)

In order to evaluate the properties of the organic electroluminescence devices according to Examples 1 to 10 and Comparative Examples 1 to 4, a driving voltage, the maximum value of external quantum efficiency, and emission color were measured. The voltage and current density of the organic electroluminescence device were measured using a source meter (Keithley Instrument Co., 2400 series), and the external quantum efficiency was measured using an external quantum efficiency measurement apparatus, C9920-12 of HAMAMATSU Photonics Co. For evaluating the maximum quantum efficiency, luminance/current density were measured using a brightness photometer of which wavelength sensitivity was calibrated, and the maximum quantum efficiency was converted supposing angular luminance distribution introducing a perfect diffusion reflecting diffuser (Lambertian). The evaluation results of the properties of the organic electroluminescence devices are shown in Table 2 below. In Table 2 below, a driving voltage and current efficiency at a current density of 2.3 mA/cm$^2$ are shown.

TABLE 2

| Device manufacturing example | Emission layer host | Driving voltage (V) | Maximum quantum efficiency (%) | Triplet energy (eV) |
| --- | --- | --- | --- | --- |
| Example 1 | Example Compound 2 | 4.2 | 20.5 | 3.07 |
| Example 2 | Example Compound 3 | 3.9 | 17.7 | 2.98 |
| Example 3 | Example Compound 6 | 4.1 | 19.8 | 3.04 |
| Example 4 | Example Compound 13 | 4.4 | 17.3 | 2.95 |
| Example 5 | Example Compound 15 | 4.1 | 18.6 | 3.04 |
| Example 6 | Example Compound 19 | 3.6 | 21.2 | 3.03 |
| Example 7 | Example Compound 26 | 4.2 | 18.9 | 3.05 |
| Example 8 | Example Compound 30 | 4.0 | 15.9 | 2.85 |
| Example 9 | Example Compound 37 | 3.8 | 19.1 | 3.05 |
| Example 10 | Example Compound 43 | 4.1 | 17.7 | 3.03 |
| Comparative Example 1 | Comparative Compound C1 | 4.4 | 17.1 | 2.89 |
| Comparative Example 2 | Comparative Compound C2 | 4.6 | 15.3 | 2.81 |
| Comparative Example 3 | Comparative Compound C3 | 4.7 | 15.6 | 2.85 |
| Comparative Example 4 | Comparative Compound C4 | 5.1 | 14.3 | 2.75 |

As shown in Table 2, the organic electroluminescence devices 10 of Examples 1 to 10, which used the polycyclic compound as the blue host material of the emission layer EML, showed lower driving voltage and improved efficiency when compared with the organic electroluminescence devices of Comparative Examples 1 to 4. In addition, it was confirmed that the organic electroluminescence devices using the compound in the emission layer showed blue emission with high color purity.

For example, if the compound is used as the material for the emission layer of a device, excellent driving voltage and efficiency may be attained, and the device may be suitable for emitting blue light.

In the Example Compounds, a bicarbazole group which is an electron donating group, represented by Formula 2 is substituted at a spirocyclic group represented by Formula 1, and hole transport capacity is improved. Accordingly, a hole transport degree in an emission layer may increase, a driving voltage may decrease, and charge balance properties may be improved, thereby improving emission efficiency. Particularly, in the bicarbazole group of the Example Compounds, nitrogen at position 9 of a carbazole substituent is bonded to a carbazole substituted. Accordingly, electron donating properties are thought to be further improved when compared with the Comparative Compounds in which a bond is formed between benzene rings of two carbazole groups. In addition, since the polycyclic compounds of the embodiments have higher lowest triplet excitation energy (T1) than the Comparative Compounds, the emission efficiency of the organic electroluminescence devices may be improved. The compound according to an embodiment may easily control the energy level and polarity of a molecule of the compound according to the introduction of various substituents and the change of a substitution position. The organic electroluminescence device of an embodiment includes the above-described polycyclic compound represented by Formula 1 as a material for an emission layer. Accordingly, the organic electroluminescence device of an embodiment may achieve high efficiency and a low driving voltage.

The polycyclic compound of an embodiment, represented by Formula 1 may be applied to an organic electroluminescence device and may achieve high efficiency and a low driving voltage.

The organic electroluminescence device according to an embodiment may achieve high efficiency and a low driving voltage.

The polycyclic compound according to an embodiment may be applied to an organic electroluminescence device to achieve high efficiency and a low driving voltage.

Although the embodiments of the invention have been described, it is understood that the invention should not be limited to these embodiments but various changes and modifications can be made by one ordinary skilled in the art within the spirit and scope of the invention as hereinafter claimed.

What is claimed is:

1. An organic electroluminescence device, comprising:
a first electrode;
a second electrode disposed on the first electrode; and
an emission layer disposed between the first electrode and the second electrode,
wherein the first electrode and the second electrode each independently comprise at least one selected from the group consisting of Ag, Mg, Cu, Al, Pt, Pd, Au, Ni, Nd, Ir, Cr, Li, Ca, LiF/Ca, LiF/Al, Mo, Ti, In, Sn, Zn, an oxide thereof, a compound thereof, and a mixture thereof, wherein the emission layer comprises a polycyclic compound represented by Formula 1:

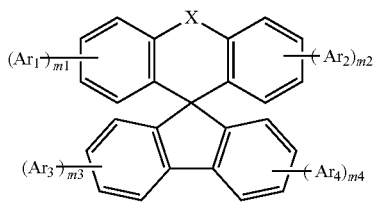

[Formula 1]

wherein in Formula 1,
X is O, S, CR$_1$R$_2$, NR$_3$, or SiR$_4$R$_5$,
R$_1$ to R$_5$ are each independently a hydrogen atom, a deuterium atom, a substituted or unsubstituted alkyl group of 1 to 20 carbon atoms, or a substituted or unsubstituted aryl group of 6 to 30 carbon atoms for forming a ring,
at least one of Ar$_1$ to Ar$_4$ is represented by Formula 2 and the remainder are each independently a hydrogen atom, a deuterium atom, a substituted or unsubstituted alkyl group of 1 to 20 carbon atoms, or a substituted or unsubstituted aryl group of 6 to 30 carbon atoms for forming a ring, and
m1 to m4 are each independently an integer from 0 to 4, where at least one of m1 to m4 is an integer from 1 to 4:

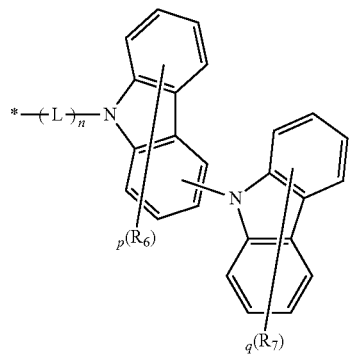

[Formula 2]

wherein in Formula 2,
R$_6$ and R$_7$ are each independently a hydrogen atom, a deuterium atom, a substituted or unsubstituted alkyl group of 1 to 20 carbon atoms, a substituted or unsubstituted silyl group, a substituted or unsubstituted aryl group of 6 to 30 carbon atoms for forming a ring, or a substituted or unsubstituted heteroaryl group of 2 to 30 carbon atoms for forming a ring,
L is a direct linkage, a substituted or unsubstituted divalent alkyl group of 1 to 20 carbon atoms, a substituted or unsubstituted arylene group of 6 to 30 carbon atoms, or a substituted or unsubstituted heteroarylene group of 2 to 30 carbon atoms,
n is 0 or 1,
p is an integer from 0 to 7, and
q is an integer from 0 to 8.

2. The organic electroluminescence device of claim 1, wherein
Ar$_1$ to Ar$_4$ are each independently represented by Formula 2.

3. The organic electroluminescence device of claim 1, wherein Formula 1 is represented by Formula 1-1 to Formula 1-5:

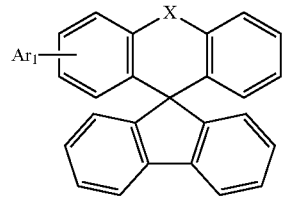

[Formula 1-1]

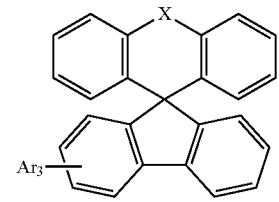

[Formula 1-2]

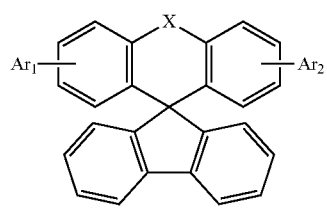

[Formula 1-3]

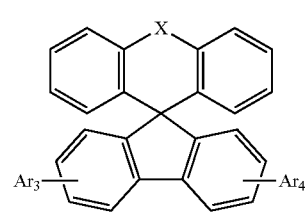

[Formula 1-4]

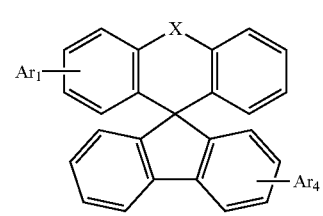

[Formula 1-5]

wherein in Formula 1-1 to Formula 1-5,
Ar$_1$ to Ar$_4$ are each independently represented by Formula 2.

4. The organic electroluminescence device of claim 1, wherein Formula 2 is represented by Formula 2-1:

[Formula 2-1]

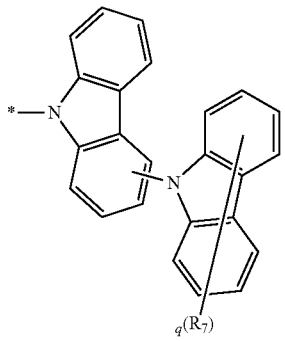

wherein in Formula 2-1,
$R_7$ and q are the same as defined in Formula 2.

5. The organic electroluminescence device of claim 1, wherein $R_1$ to $R_5$ are each independently substituted or unsubstituted alkyl groups of 1 to 5 carbon atoms, or substituted or unsubstituted phenyl groups.

6. The organic electroluminescence device of claim 1, wherein $R_7$ is a hydrogen atom, a t-butyl group, an aryl silyl group, a substituted or unsubstituted phenyl group, a substituted or unsubstituted naphthyl group, a substituted or unsubstituted dibenzofuran group, or a substituted or unsubstituted dibenzothiophene group.

7. The organic electroluminescence device of claim 1, wherein
the emission layer comprises a host and a dopant, and
the host comprises the polycyclic compound.

8. The organic electroluminescence device of claim 7, wherein the dopant is a phosphorescence dopant, or a thermally activated delayed fluorescence dopant.

9. The organic electroluminescence device of claim 1, wherein the emission layer emits blue light.

10. The organic electroluminescence device of claim 1, wherein the emission layer comprises at least one among compounds represented by Compound Group 1:

[Compound Group 1]

1
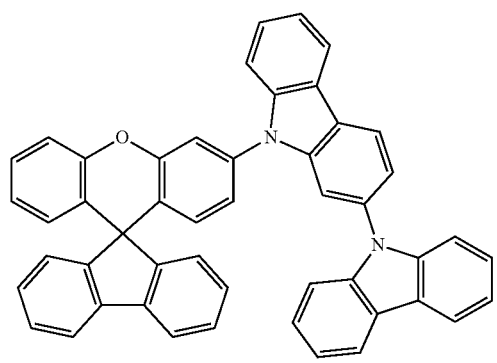

2
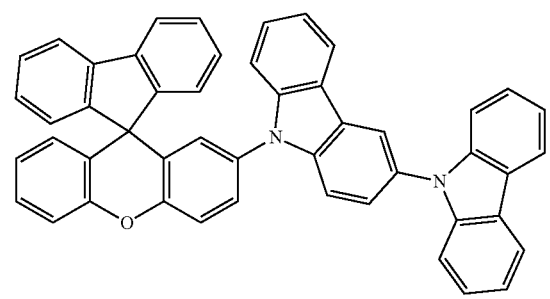

3
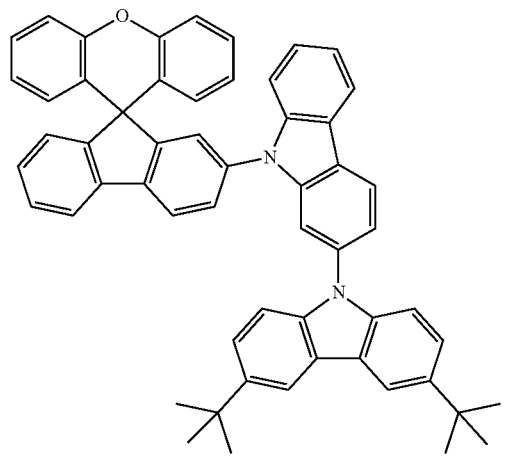

4
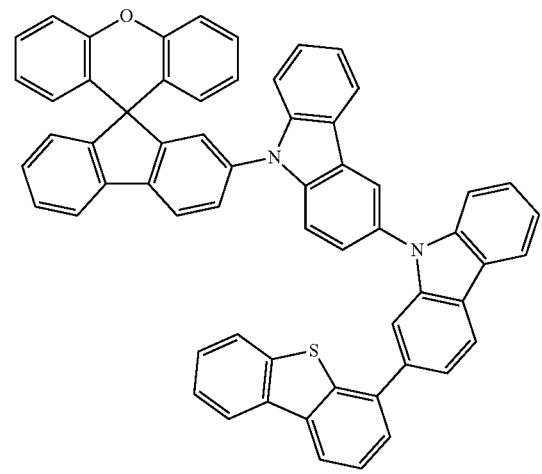

5
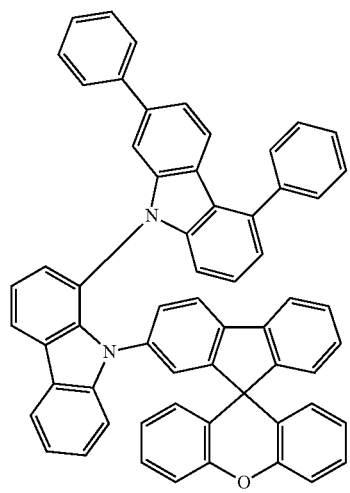
6
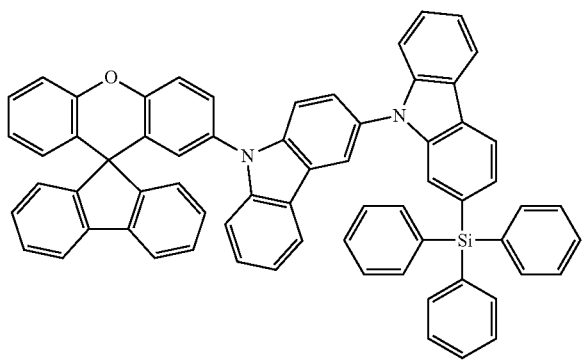
7
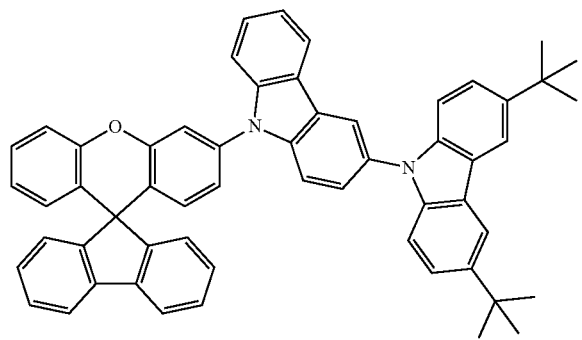
8
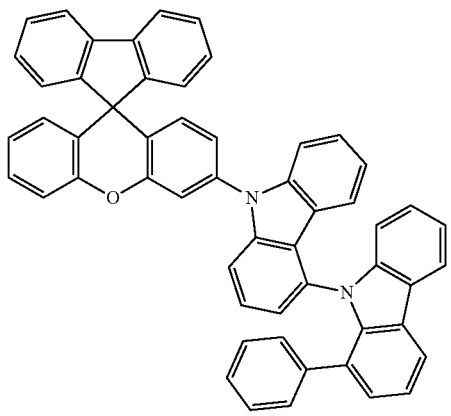
9
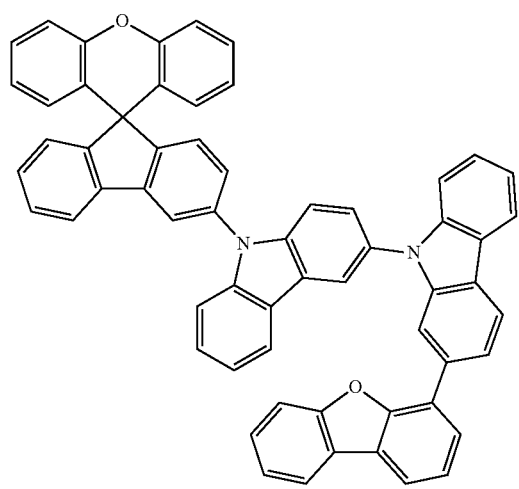
10
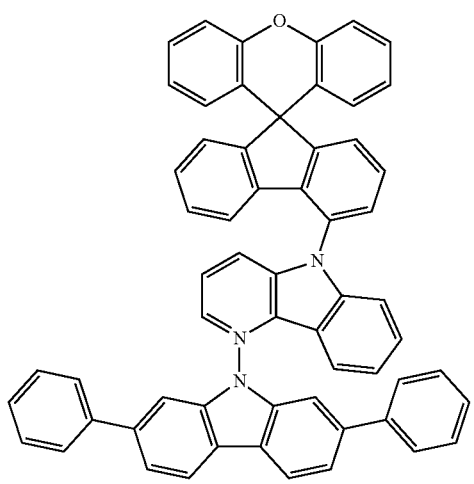

-continued
11
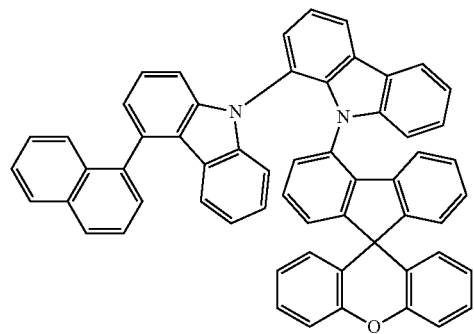
12
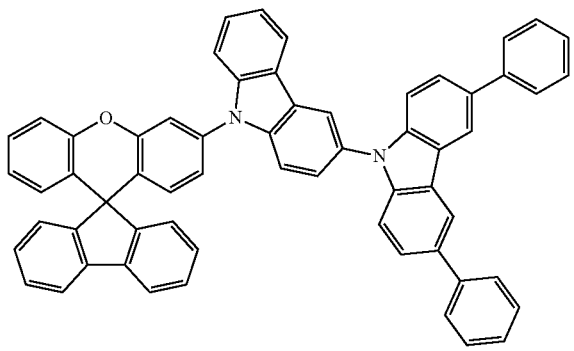
13
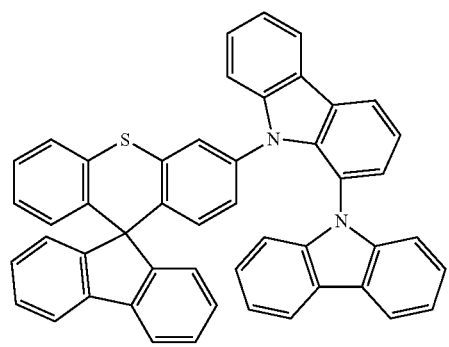
14
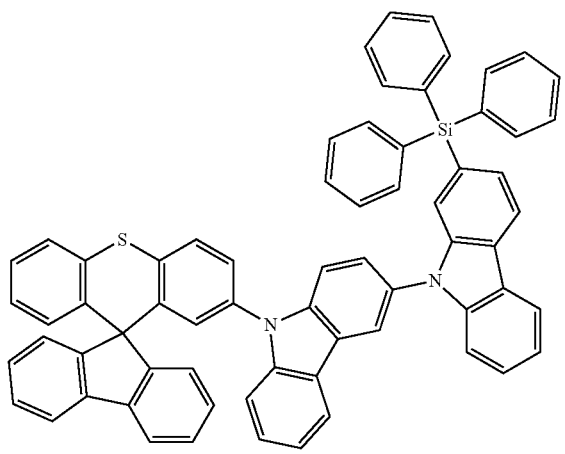
15
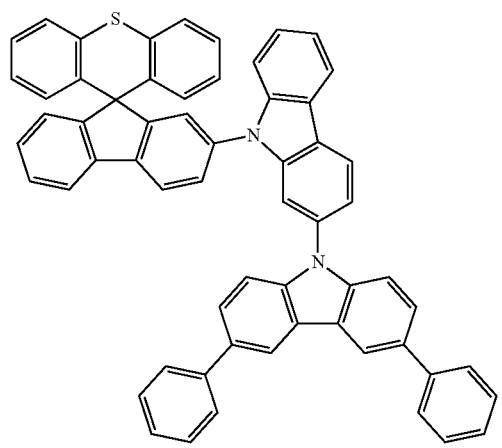
16
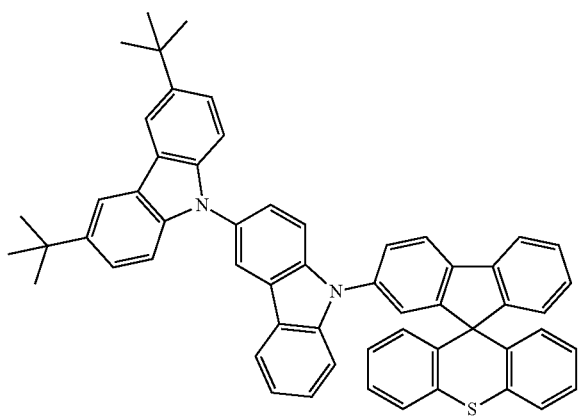

-continued
17
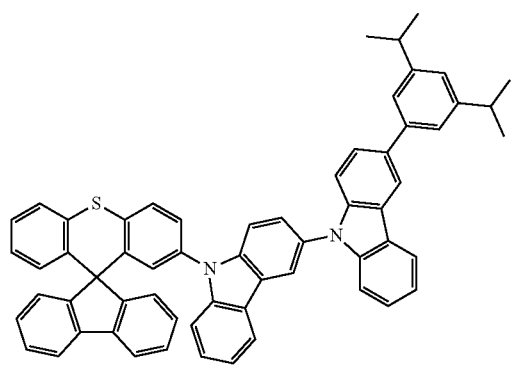
18
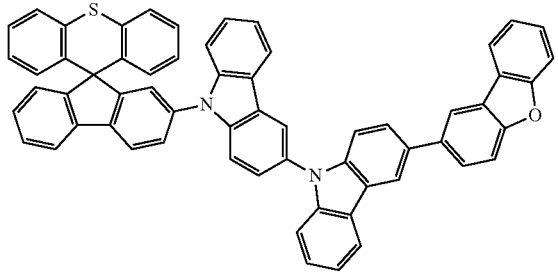
19
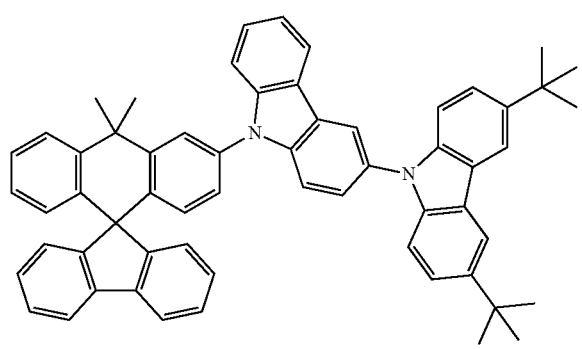
20
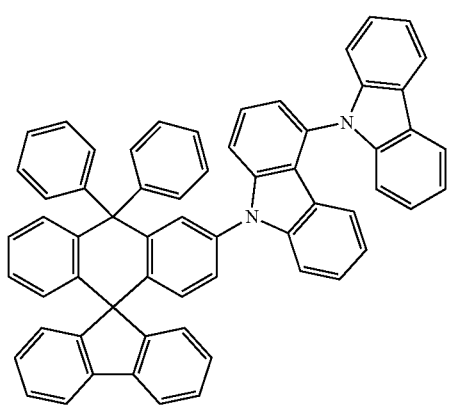
21
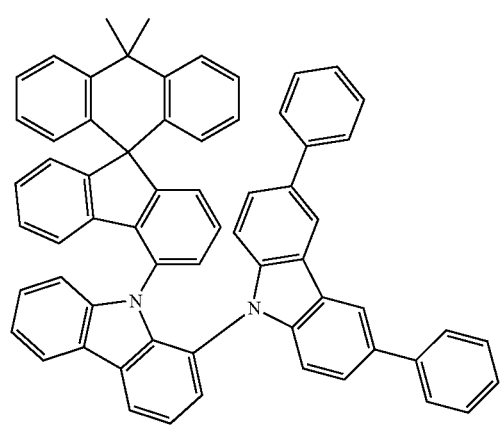
22
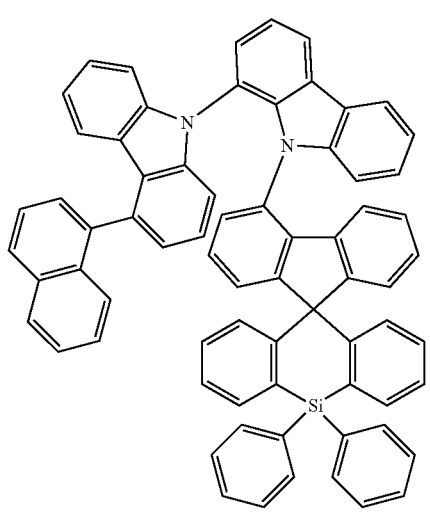
23
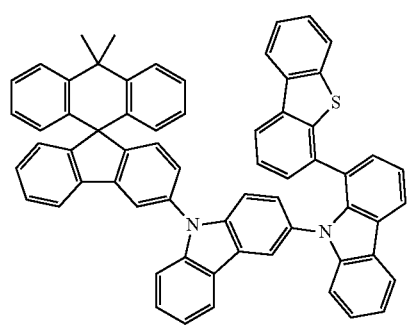
24
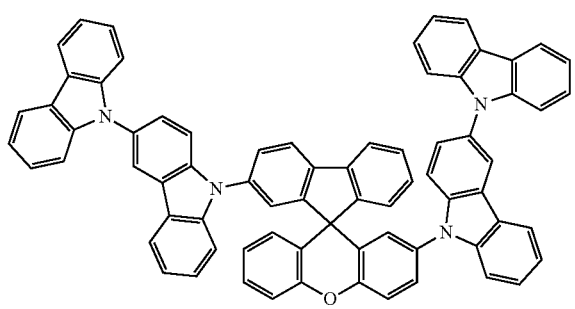

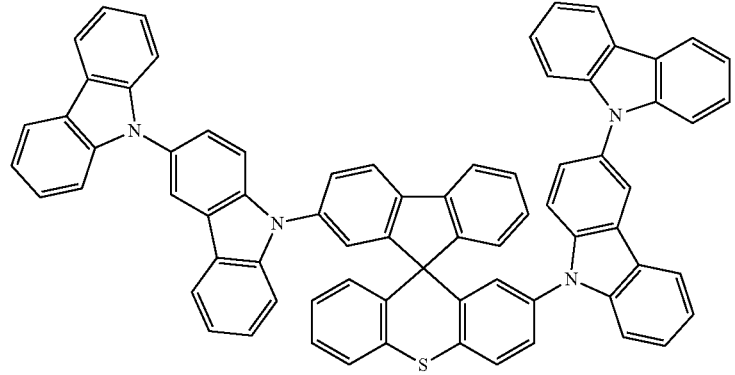
25
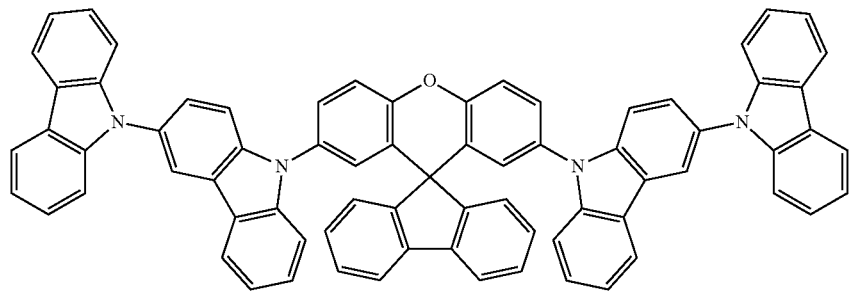
26
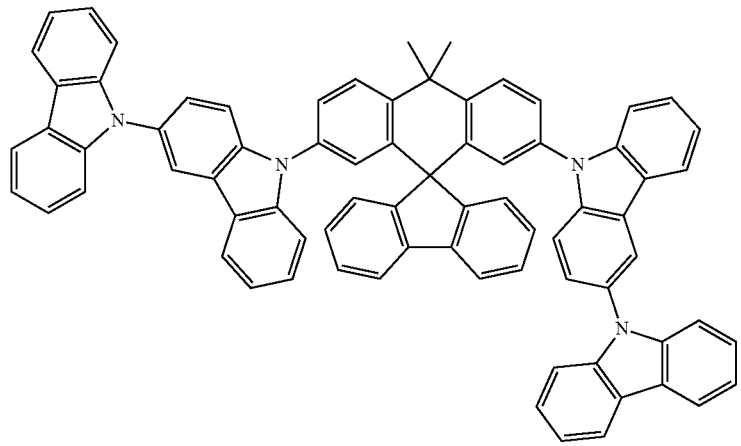
27
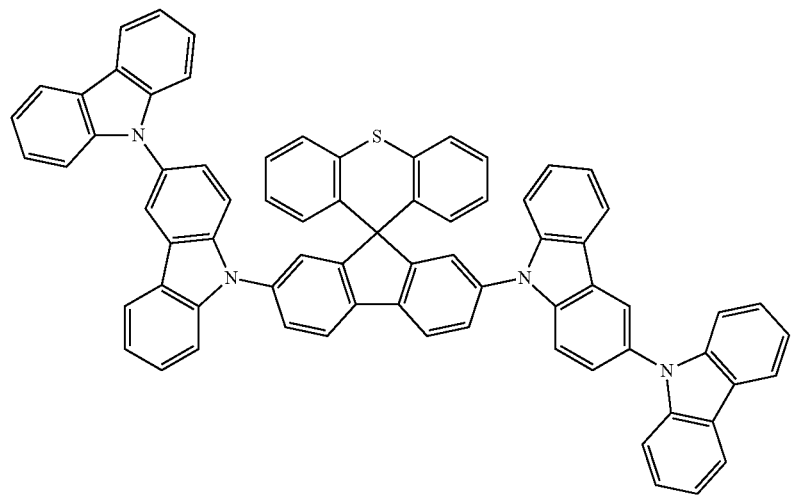
28

-continued
29
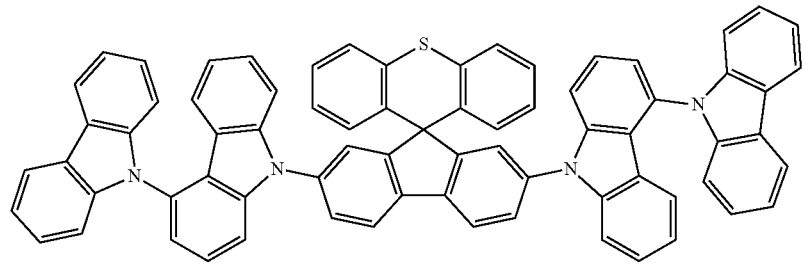
30
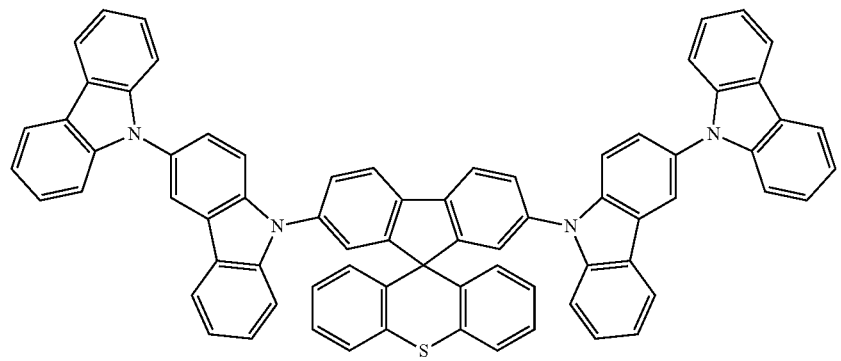
31
32
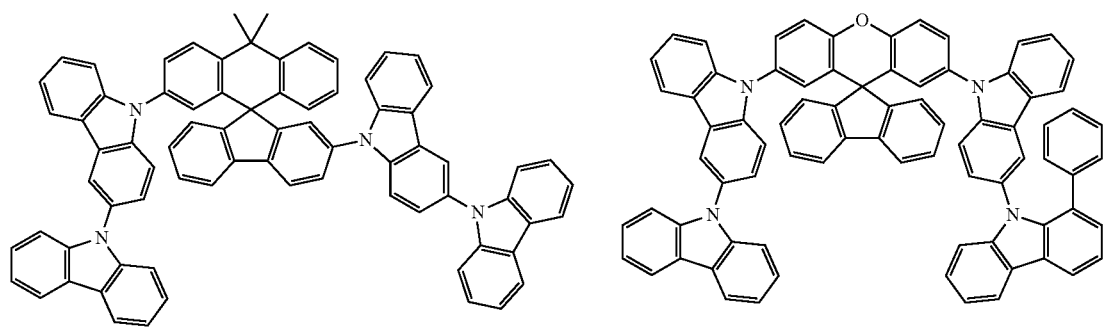
33
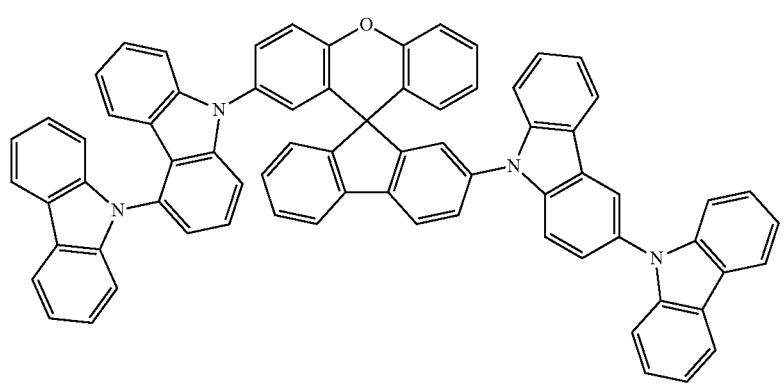

34
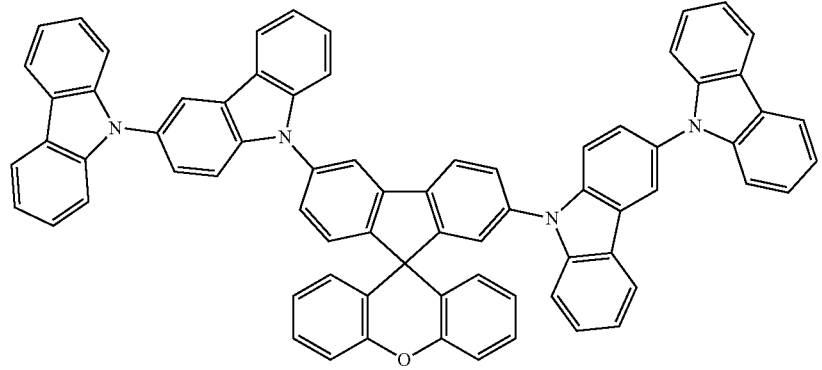
35
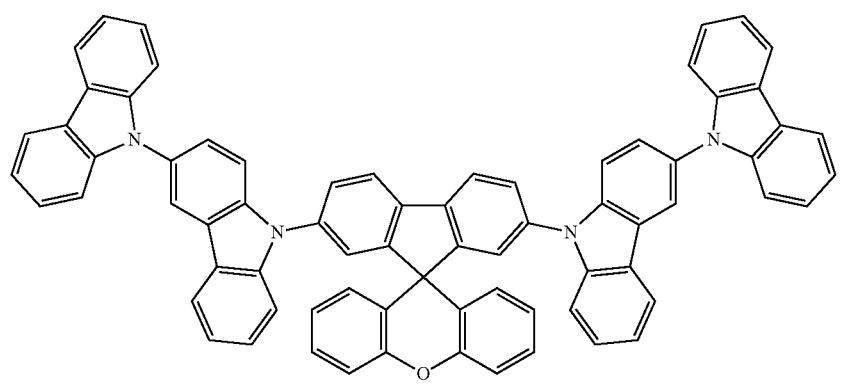
36
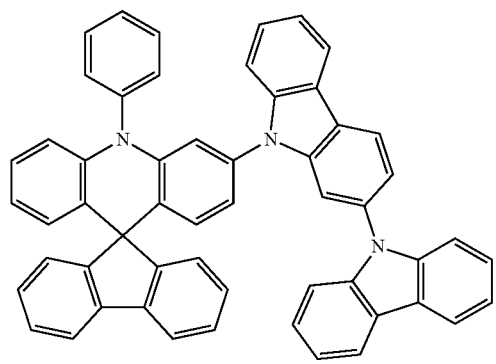
37
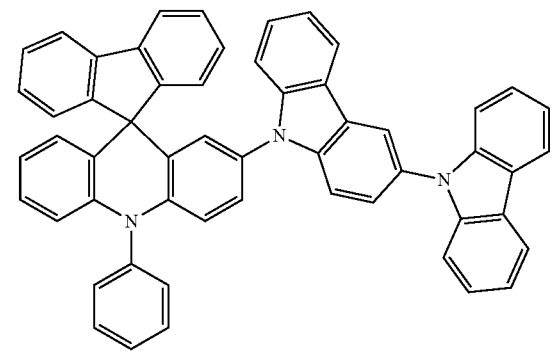

38
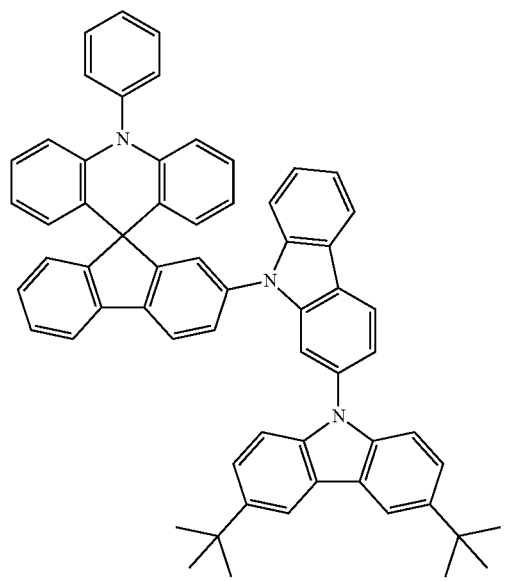
39
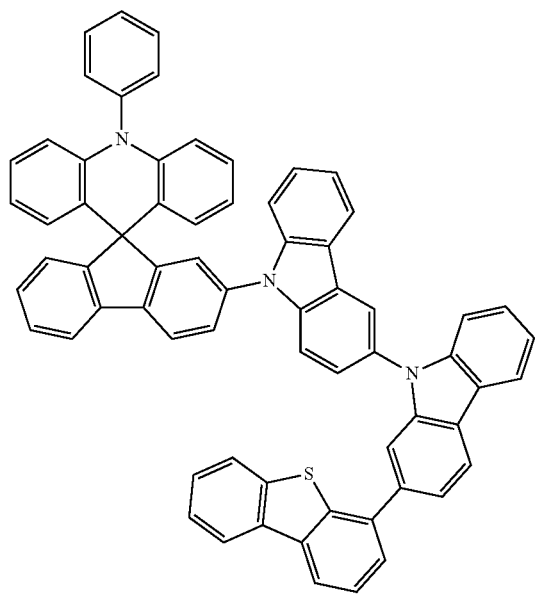
40
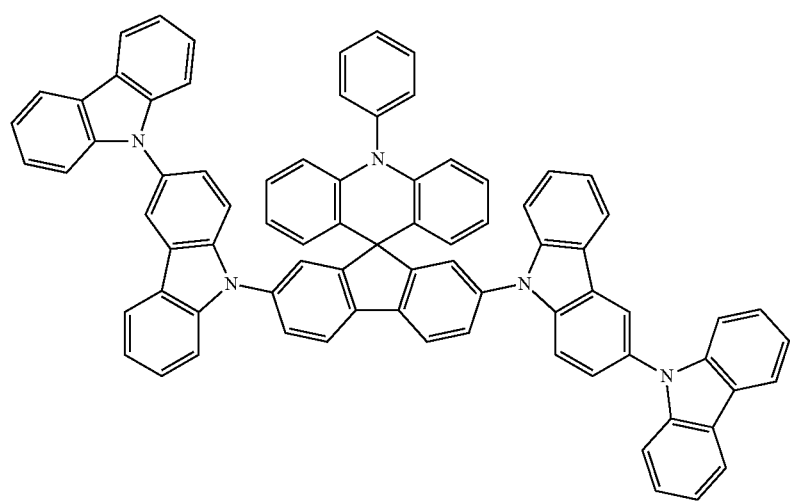

-continued
41
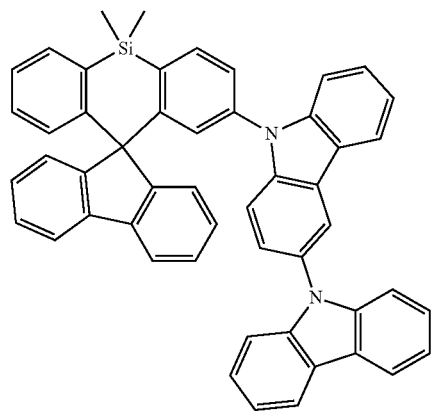
42
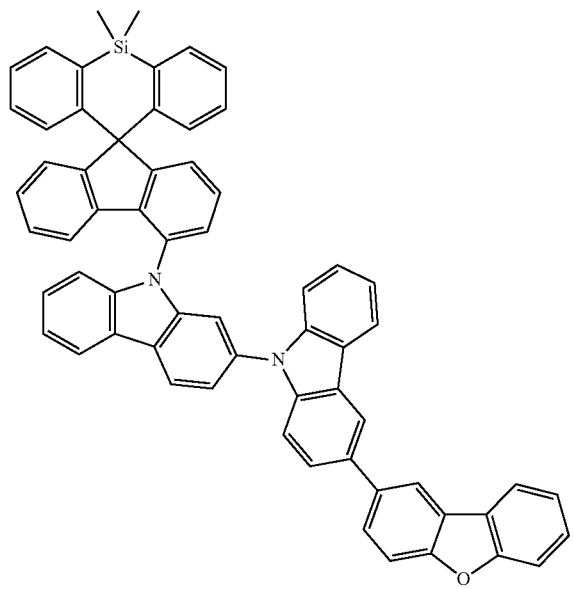
43
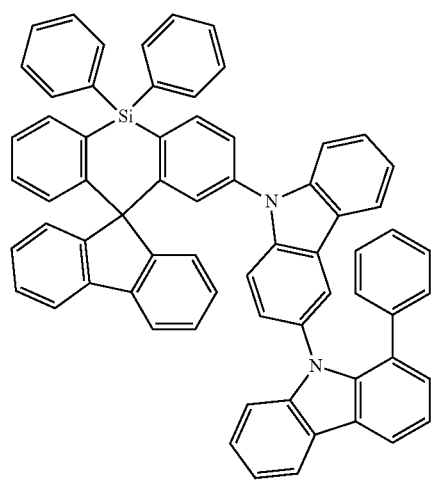
44
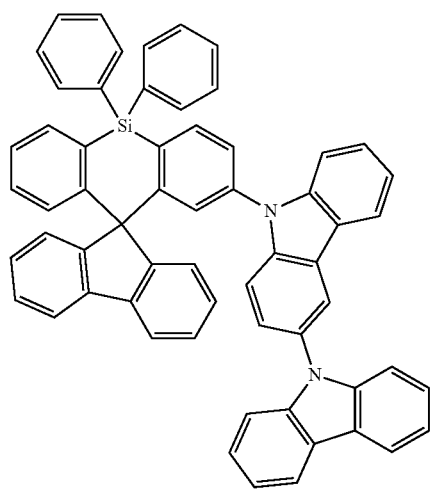
45
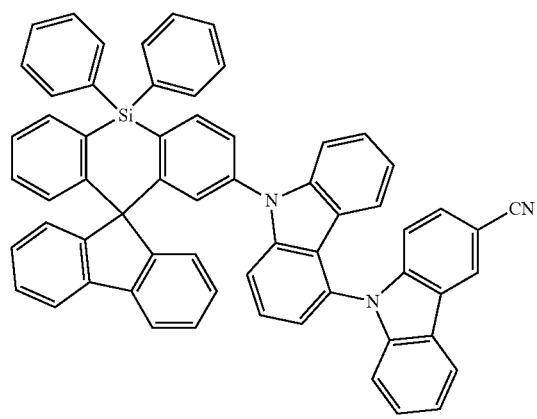
46
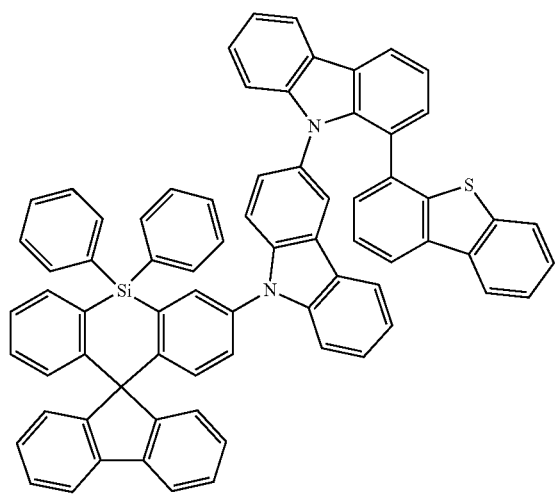

-continued

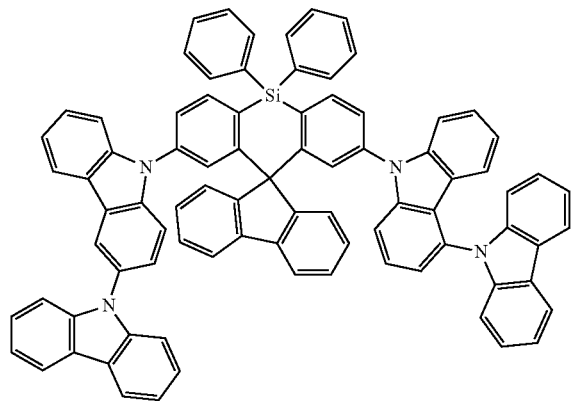
47

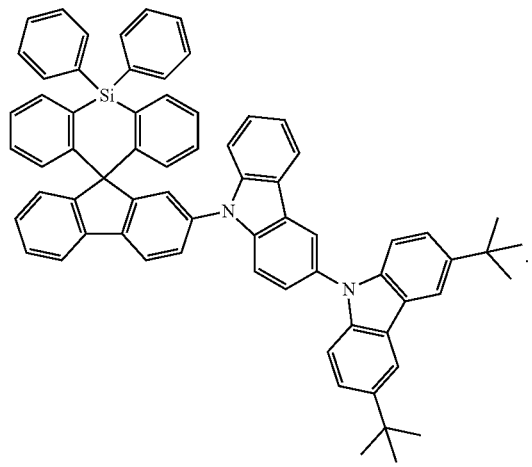
48

11. A polycyclic compound represented by Formula 1:

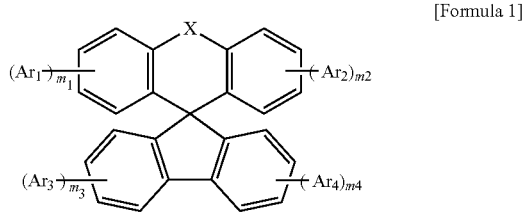

[Formula 1]

wherein in Formula 1, X is O, S, CR₁R₂, NR₃, or SiR₄R₅,
R₁ to R₅ are each independently a hydrogen atom, a deuterium atom, a substituted or unsubstituted alkyl group of 1 to 20 carbon atoms, or a substituted or unsubstituted aryl group of 6 to 30 carbon atoms for forming a ring,
at least one of Ar₁ to Ar₄ is represented by Formula 2 and the remainder are each independently a hydrogen atom, a deuterium atom, a substituted or unsubstituted alkyl group of 1 to 20 carbon atoms, or a substituted or unsubstituted aryl group of 6 to 30 carbon atoms for forming a ring, and
m1 to m4 are each independently an integer from 0 to 4, where at least one of m1 to m4 is an integer from 1 to 4:

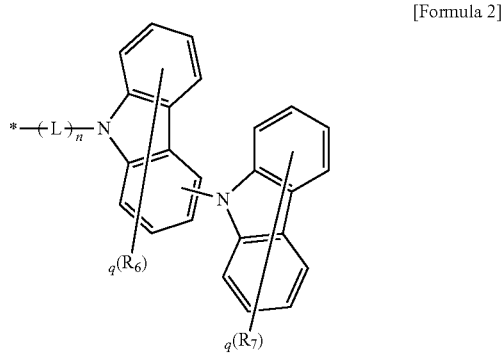

[Formula 2]

wherein in Formula 2,
R₆ and R₇ are each independently a hydrogen atom, a deuterium atom, a substituted or unsubstituted alkyl group of 1 to 20 carbon atoms, a substituted or unsubstituted silyl group, a substituted or unsubstituted aryl group of 6 to 30 carbon atoms for forming a ring, or a substituted or unsubstituted heteroaryl group of 2 to 30 carbon atoms for forming a ring,
L is a direct linkage, a substituted or unsubstituted divalent alkyl group of 1 to 20 carbon atoms, a substituted or unsubstituted arylene group of 6 to 30 carbon atoms, or a substituted or unsubstituted heteroarylene group of 2 to 30 carbon atoms,
n is 0 or 1,
p is an integer from 0 to 7, and
q is an integer from 0 to 8.

12. The polycyclic compound of claim 11, wherein Ar₁ to Ar₄ are each independently represented by Formula 2.

13. The polycyclic compound of claim 11, wherein Formula 1 is represented by Formula 1-1 to Formula 1-5:

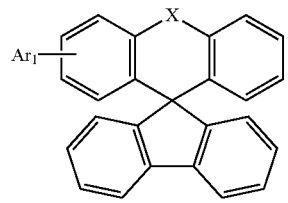

[Formula 1-1]

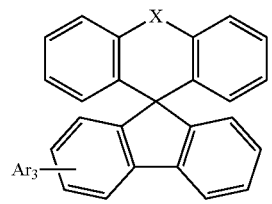

[Formula 1-2]

[Formula 1-3]

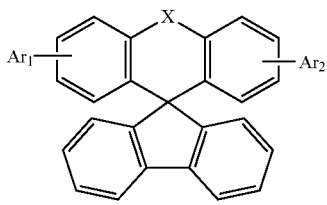

[Formula 1-4]

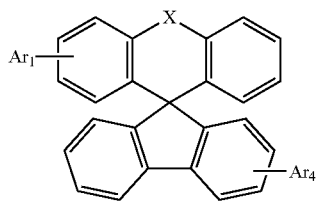

[Formula 1-5]

wherein in Formula 1-1 to Formula 1-5,
Ar₁ to Ar₄ are each independently represented by Formula 2 above.

14. The polycyclic compound of claim 11, wherein Formula 2 is represented by Formula 2-1:

[Formula 2-1]

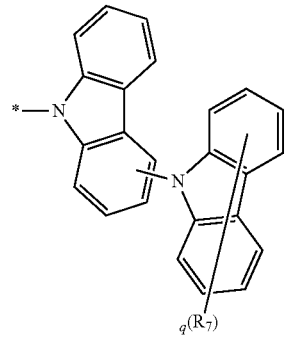

wherein in Formula 2-1,
$R_7$ and q are the same as defined in Formula 2.

15. The polycyclic compound of claim 11, wherein $R_1$ to $R_5$ are each independently substituted or unsubstituted alkyl groups of 1 to 5 carbon atoms, or substituted or unsubstituted phenyl groups.

16. The polycyclic compound of claim 11, wherein $R_7$ is a hydrogen atom, a t-butyl group, an aryl silyl group, a substituted or unsubstituted phenyl group, a substituted or unsubstituted naphthyl group, a substituted or unsubstituted dibenzofuran group, or a substituted or unsubstituted dibenzothiophene group.

17. The polycyclic compound of claim 11, wherein Formula 1 is any one among compounds represented by Compound Group 1:

[Compound Group 1]

1

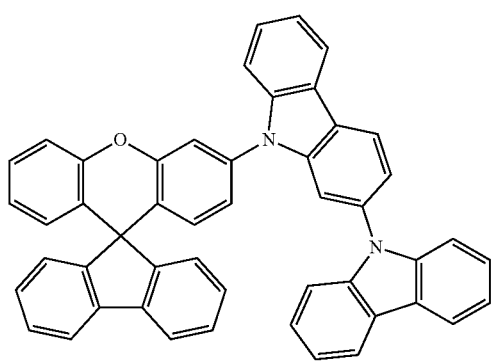

2

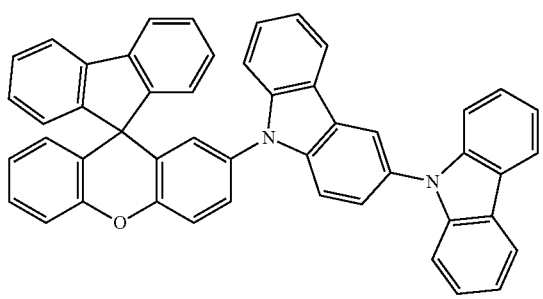

-continued
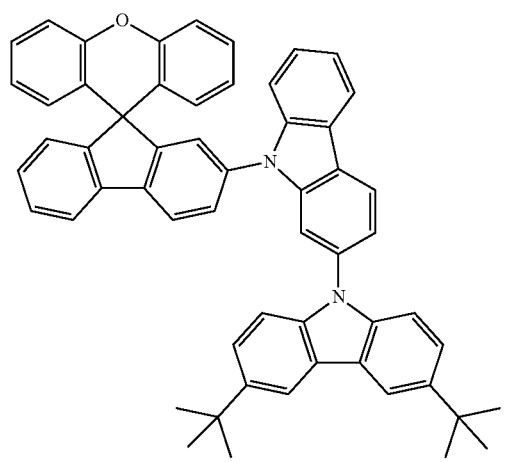
3
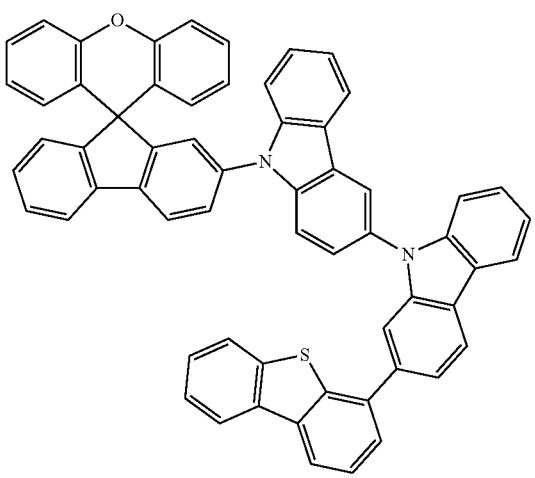
4
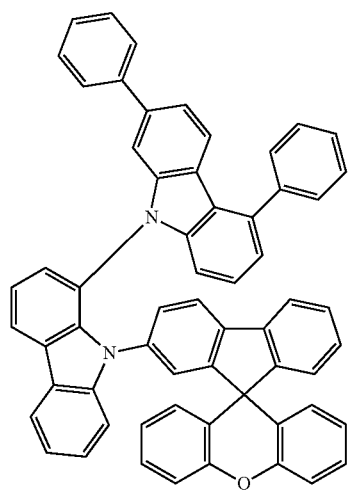
5
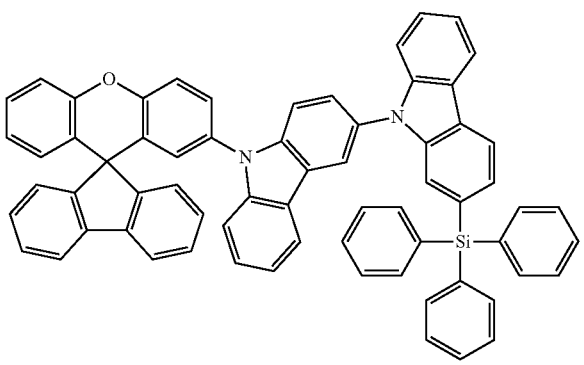
6
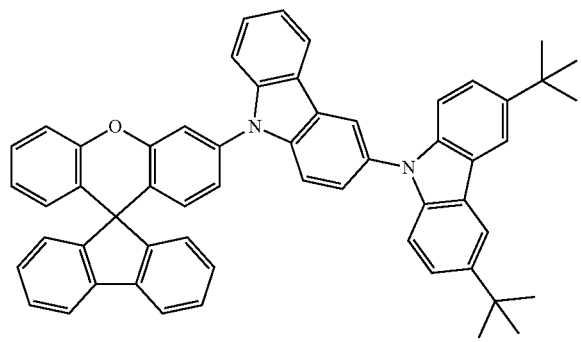
7
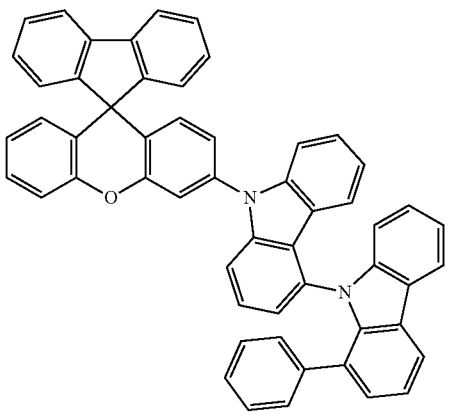
8

-continued
9
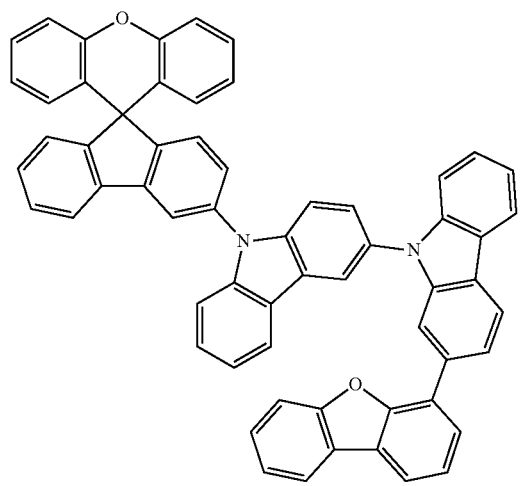
10
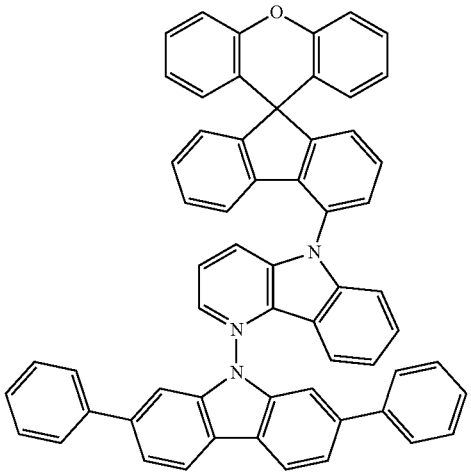
11
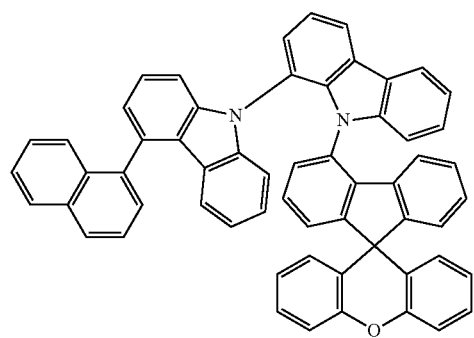
12
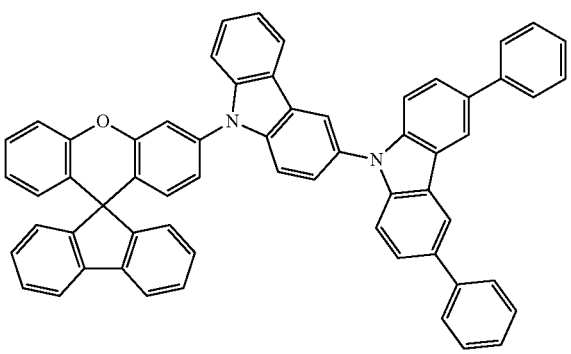
13
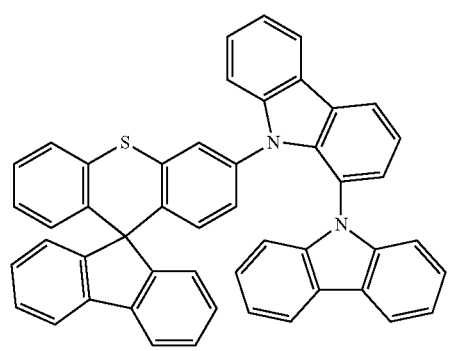
14
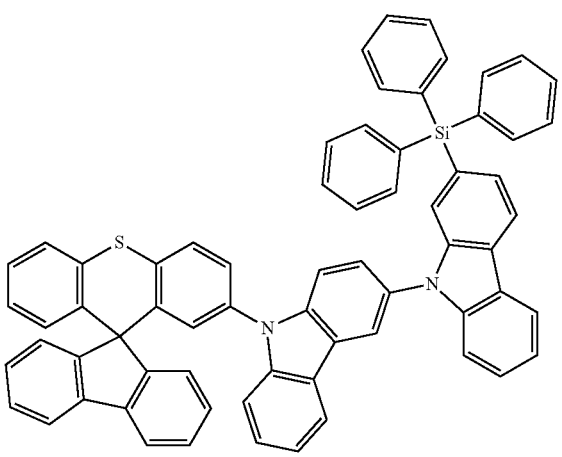

15
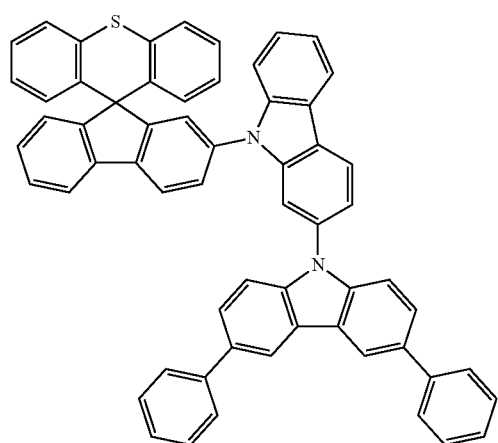
16
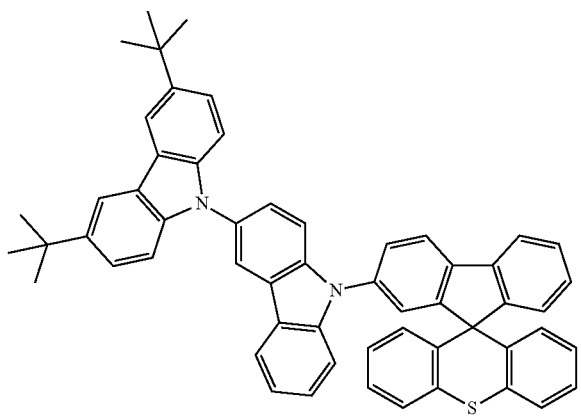
17
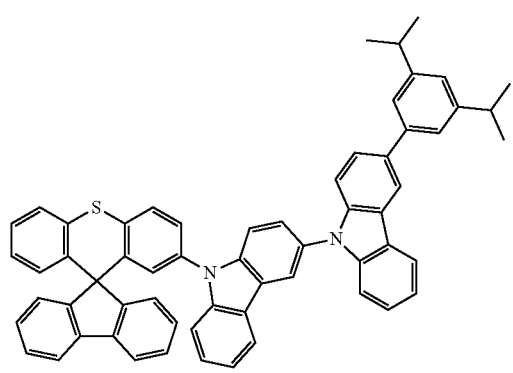
18
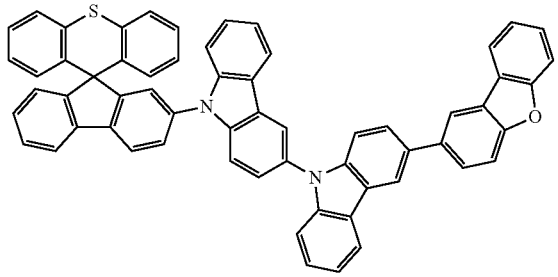
19
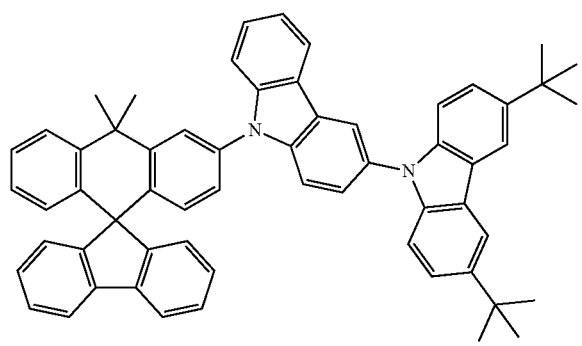
20
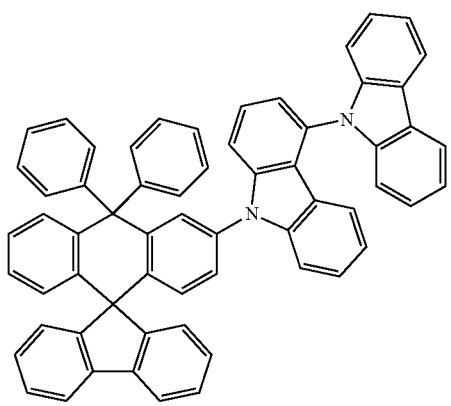

-continued
21
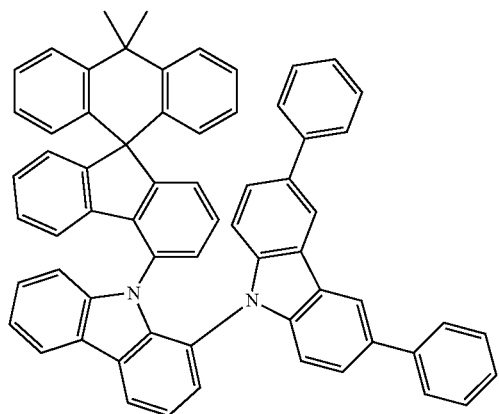
22
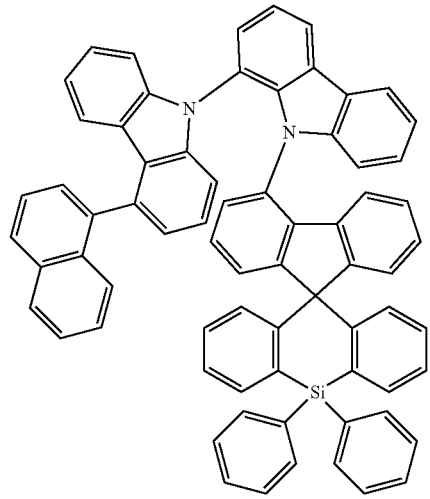
23
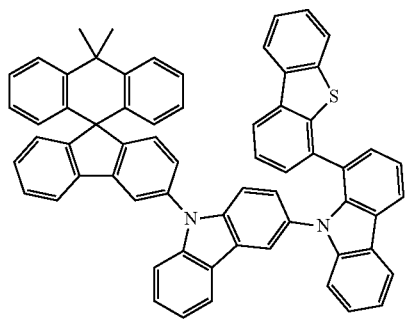
24
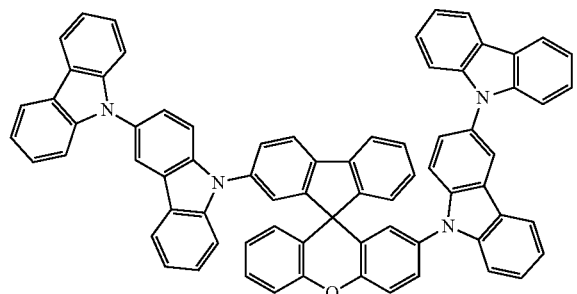
25
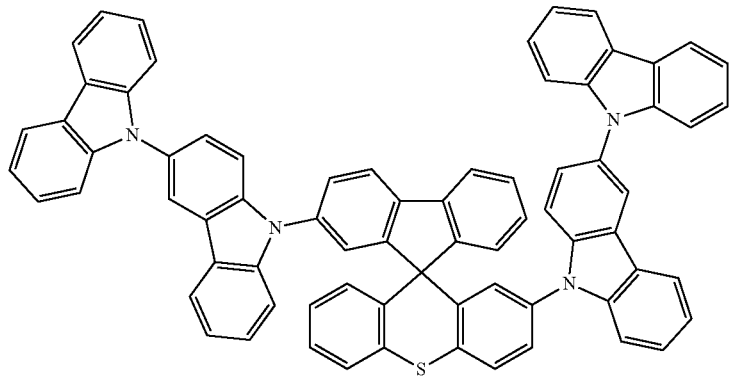
26
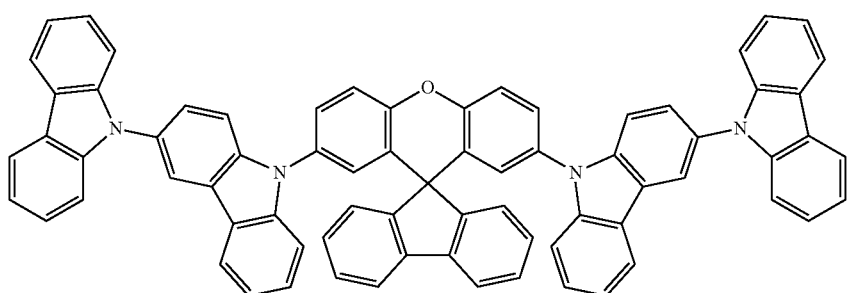

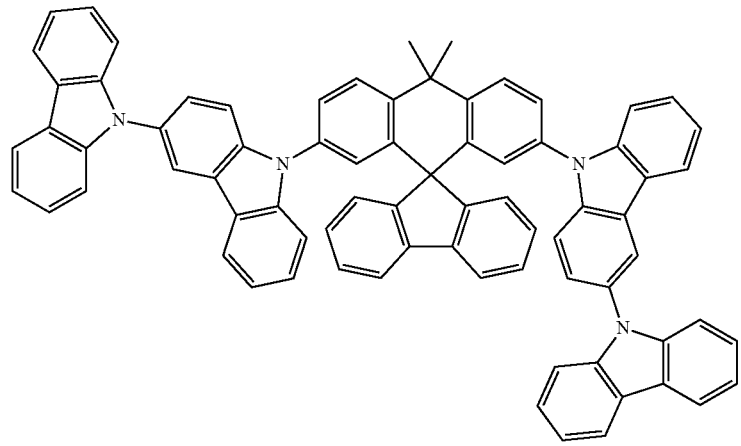
27
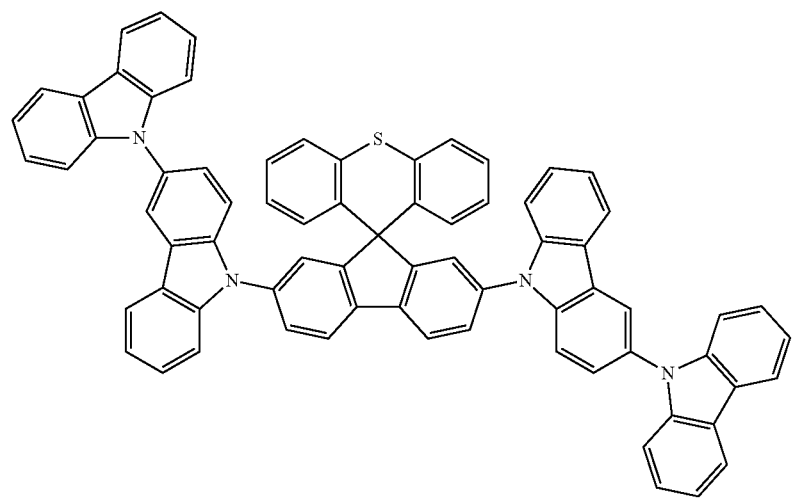
28
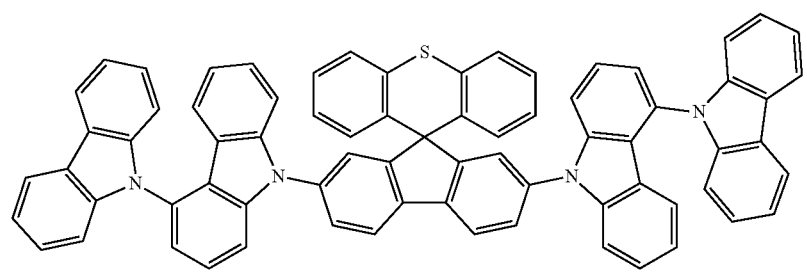
29
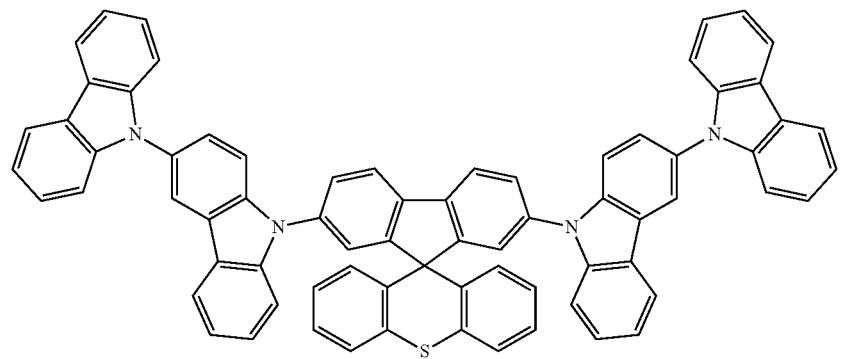
30

-continued
31
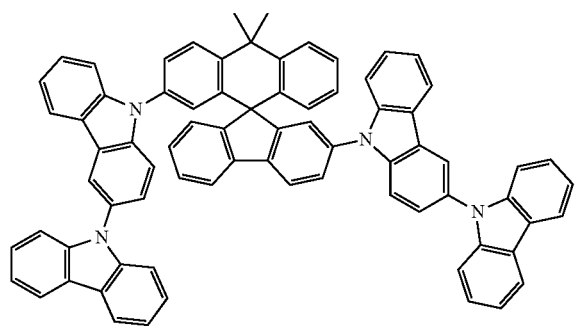
32
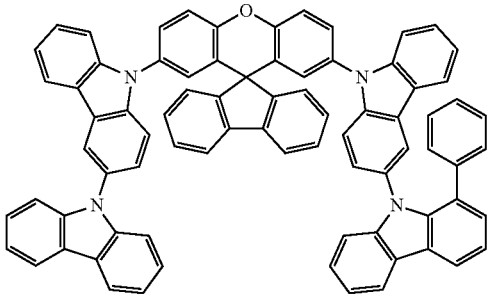
33
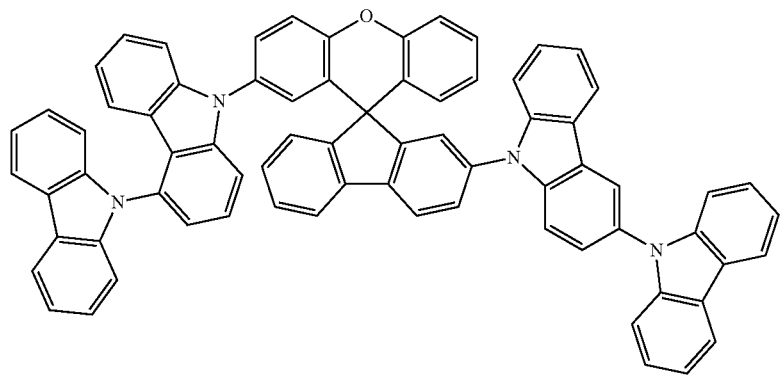
34
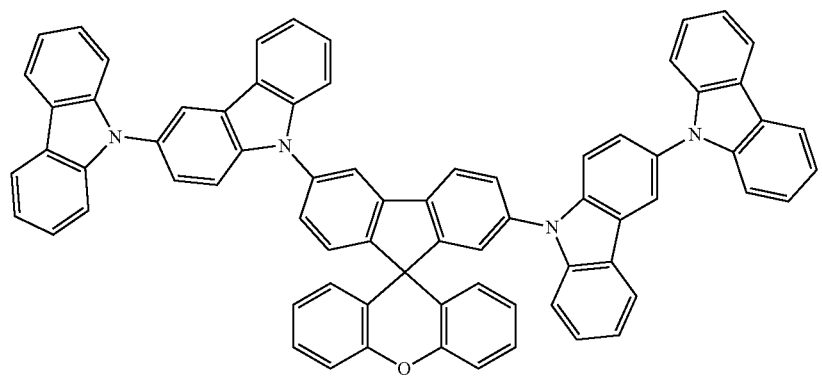
35
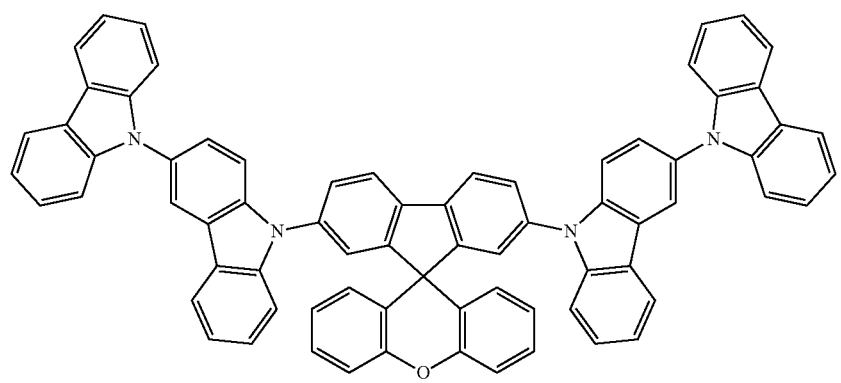

-continued
36
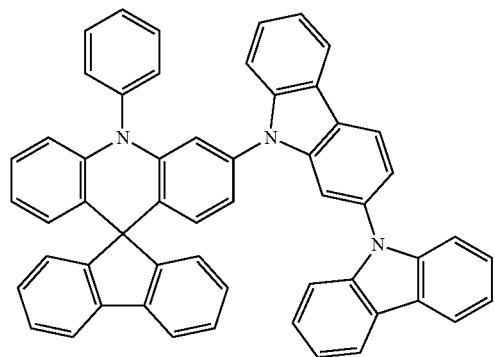
37
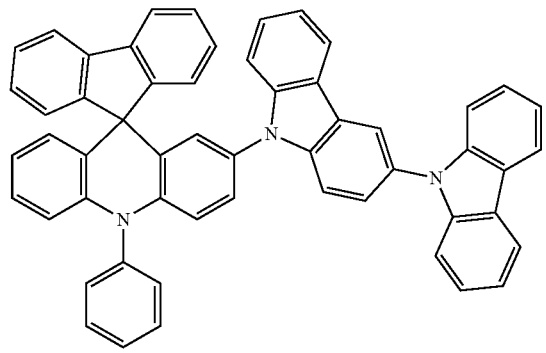
38
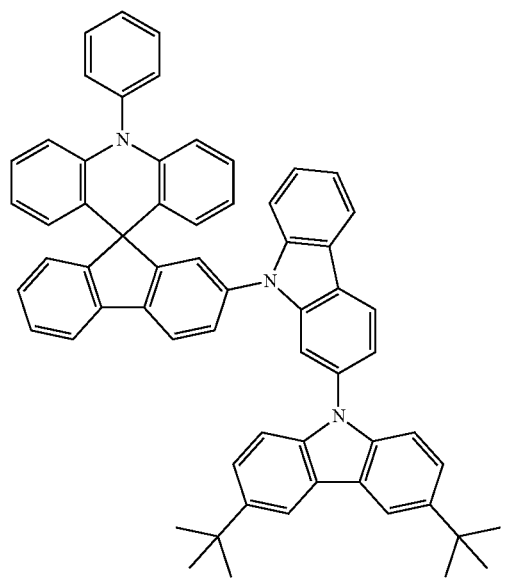
39
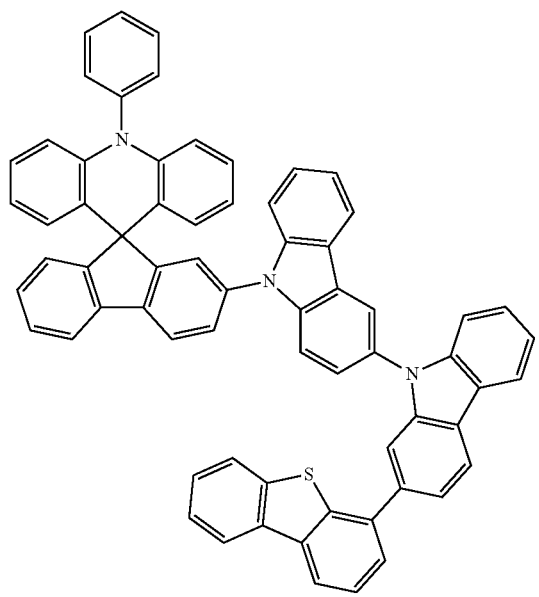
40
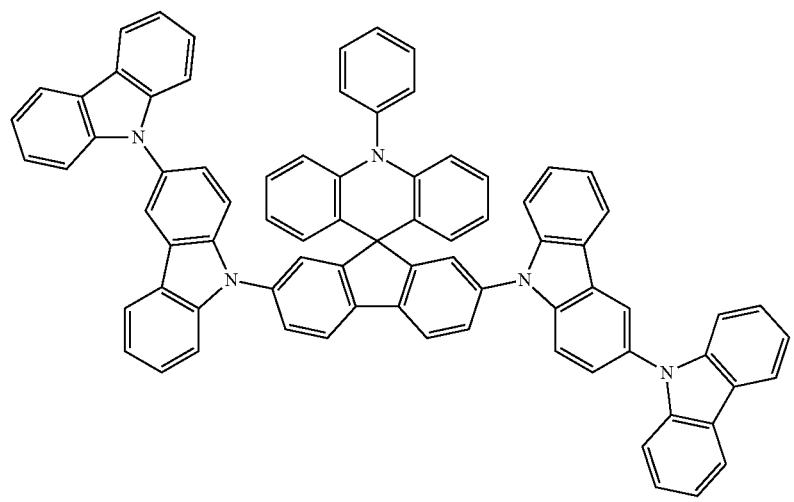

-continued
41
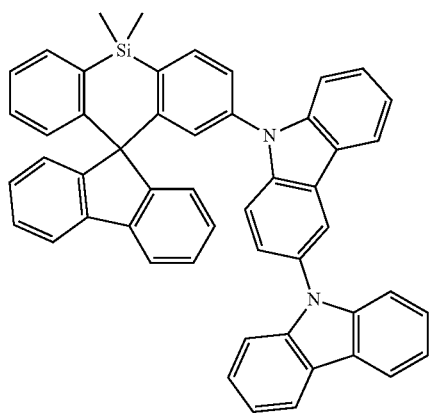
42
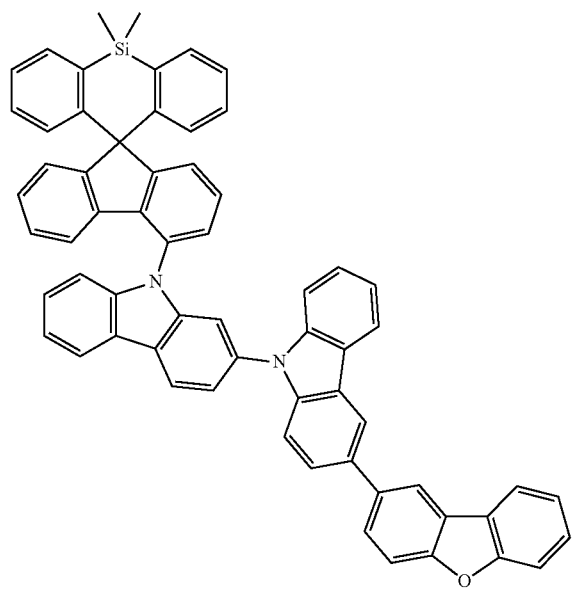
43
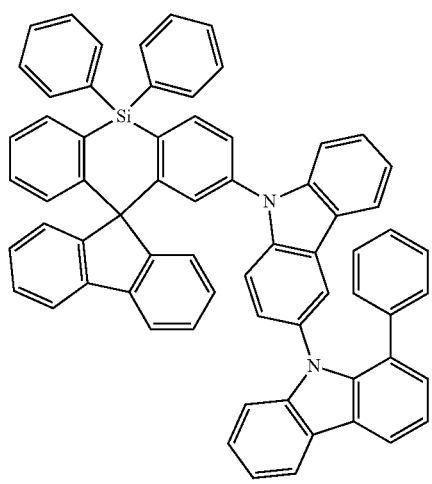
44
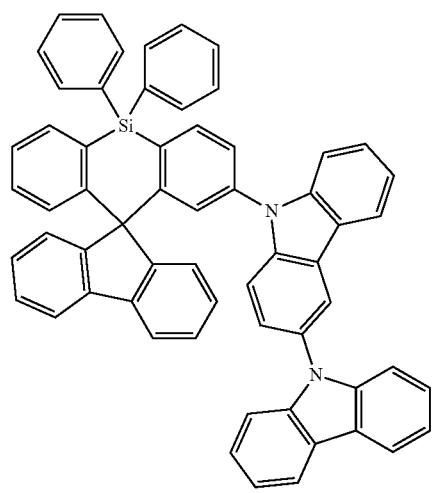
45
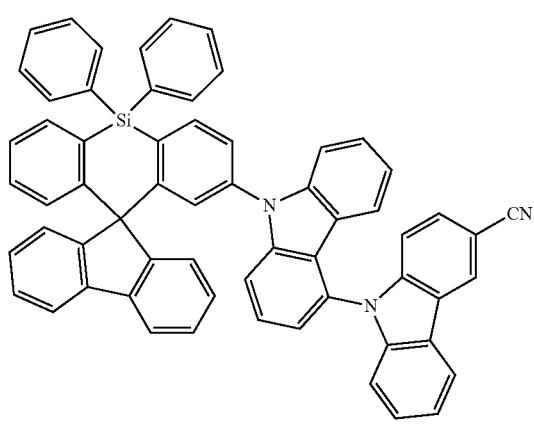
46
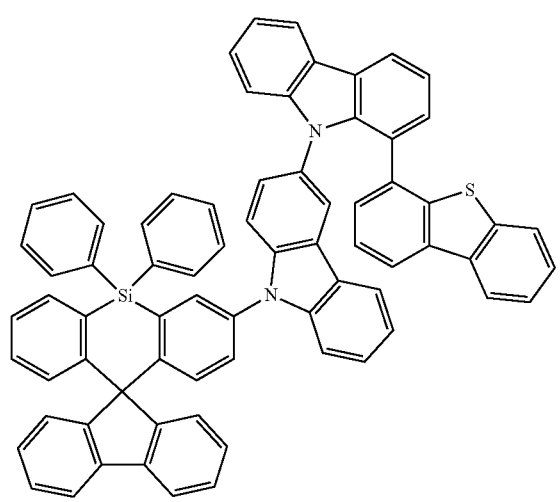

47

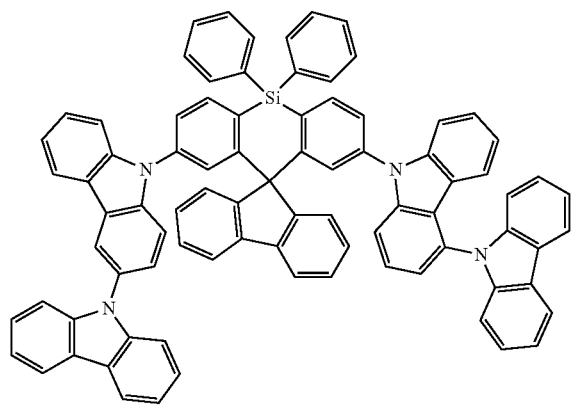

48

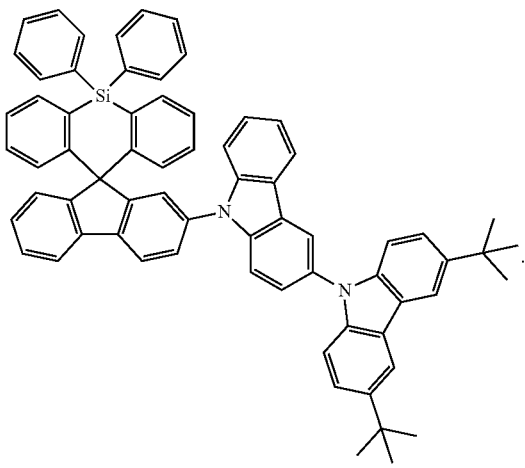

18. A polycyclic compound represented by Formula 3:

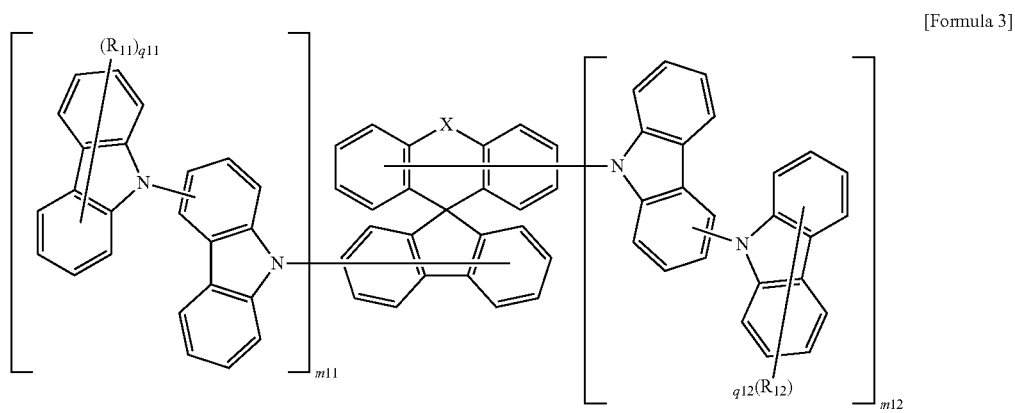

[Formula 3]

wherein in Formula 3,

X is O, S, $CR_1R_2$, $NR_3$, or $SiR_4R_5$, $R_1$ to $R_5$ are each independently a hydrogen atom, a deuterium atom, a substituted or unsubstituted alkyl group of 1 to 20 carbon atoms, or a substituted or unsubstituted aryl group of 6 to 30 carbon atoms for forming a ring, $R_{11}$ and $R_{12}$ are each independently a hydrogen atom, a deuterium atom, a substituted or unsubstituted alkyl group of 1 to 20 carbon atoms, a substituted or unsubstituted silyl group, a substituted or unsubstituted aryl group of 6 to 30 carbon atoms for forming a ring, or a substituted or unsubstituted heteroaryl group of 2 to 30 carbon atoms for forming a ring, q11 and q12 are each independently an integer from 0 to 8, and m11 and m12 are each independently an integer from 0 to 2, where at least one of m11 or m12 is 1 or 2.

19. The polycyclic compound of claim 18, wherein Formula 3 is represented by Formula 3-1:

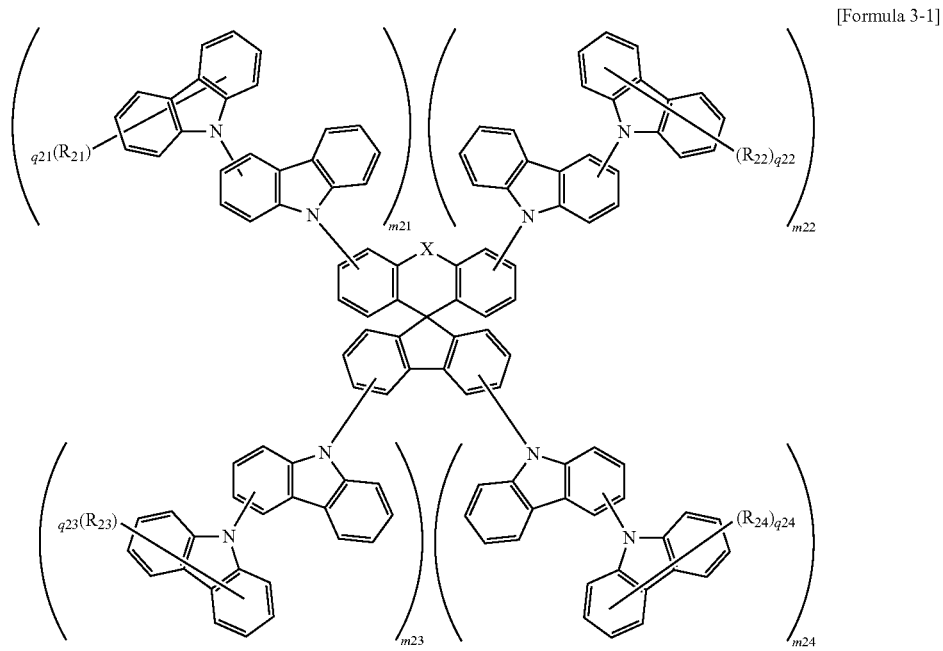

[Formula 3-1]

wherein in Formula 3-1, $R_{21}$ to $R_{24}$ are each independently a hydrogen atom, a deuterium atom, a substituted or unsubstituted alkyl group of 1 to 20 carbon atoms, a substituted or unsubstituted silyl group, a substituted or unsubstituted aryl group of 6 to 30 carbon atoms for forming a ring, or a substituted or unsubstituted heteroaryl group of 2 to 30 carbon atoms for forming a ring, m21 to m24 are each independently 0 or 1, where at least one of m21 to m24 is 1, q21 to q24 are each independently an integer from 0 to 8, and X is the same as defined in Formula 3.

20. The polycyclic compound of claim 18, wherein Formula 3 is any one among compounds represented by Compound Group 1:

[Compound Group 1]

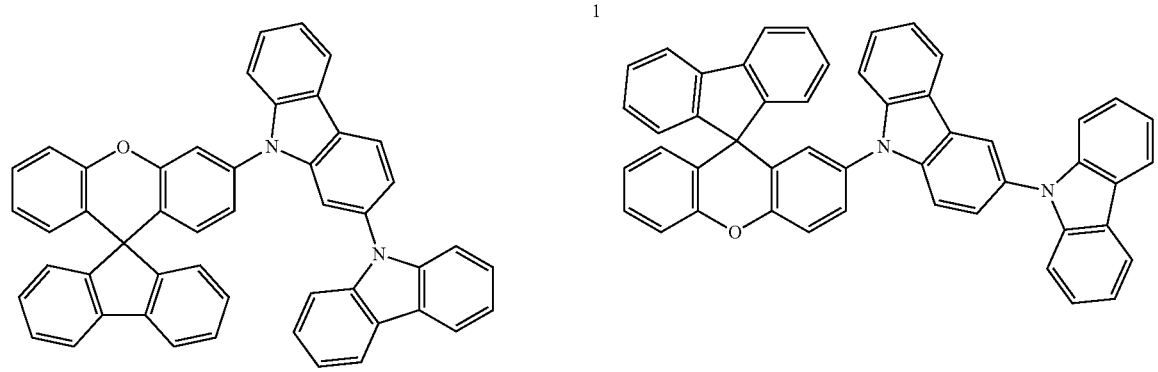

-continued
3
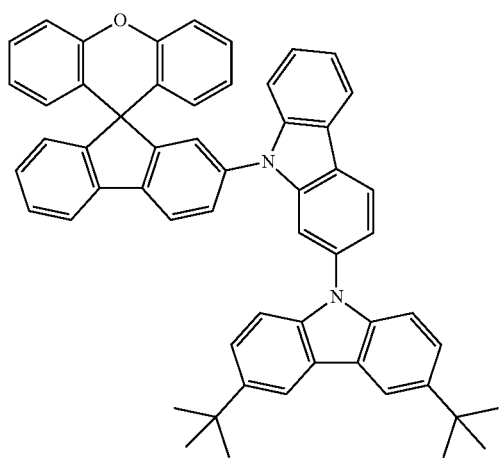
4
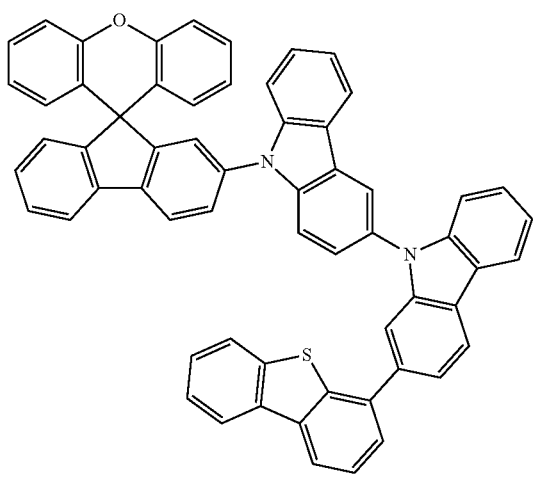
5
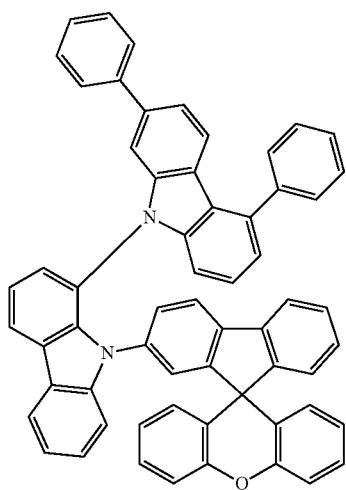
6
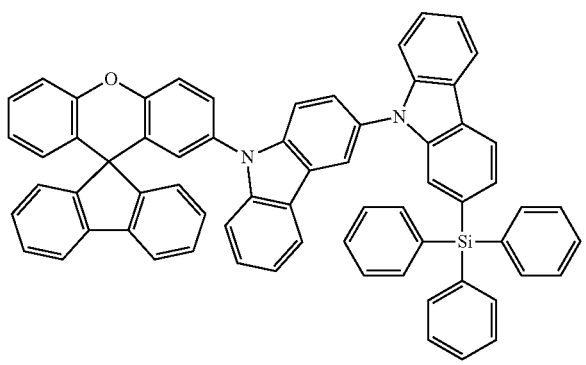
7
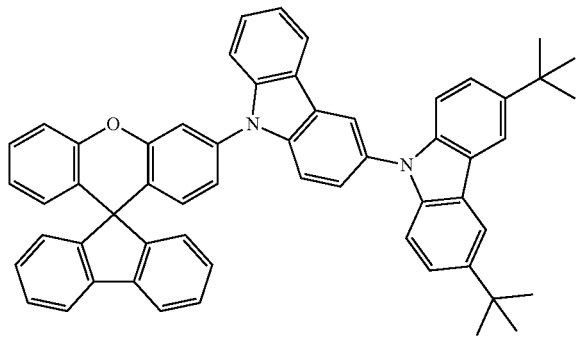
8
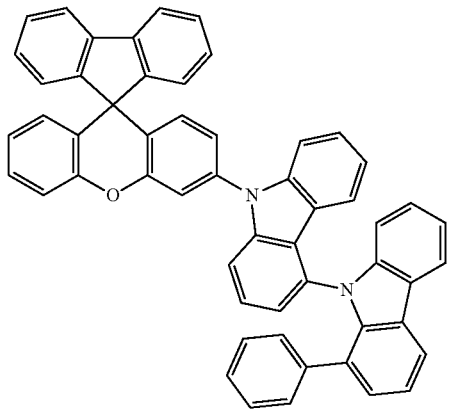

-continued
9
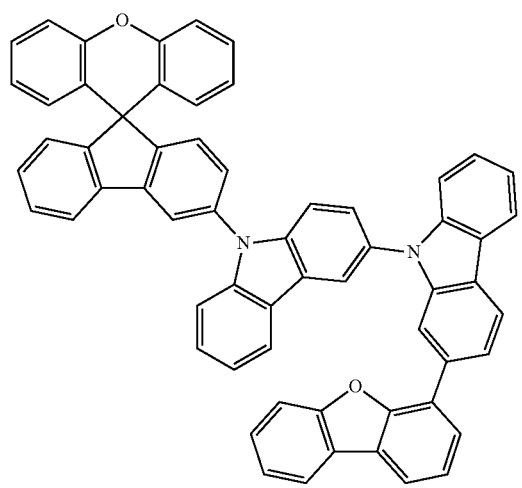
10
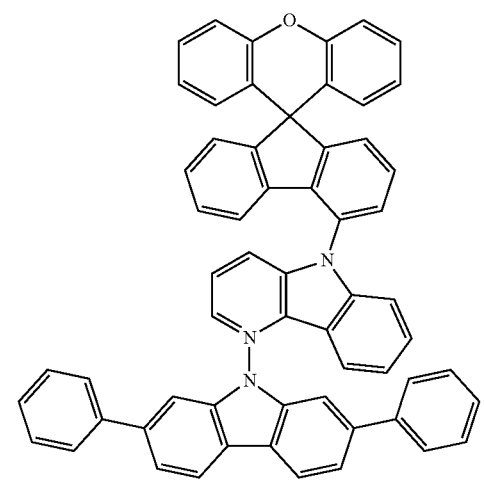
11
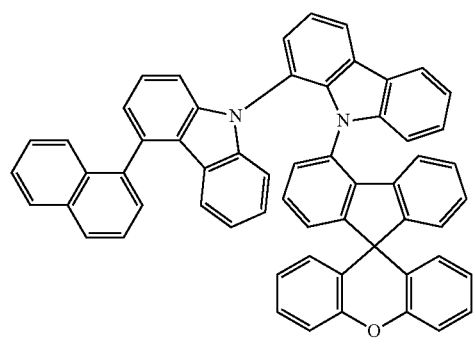
12
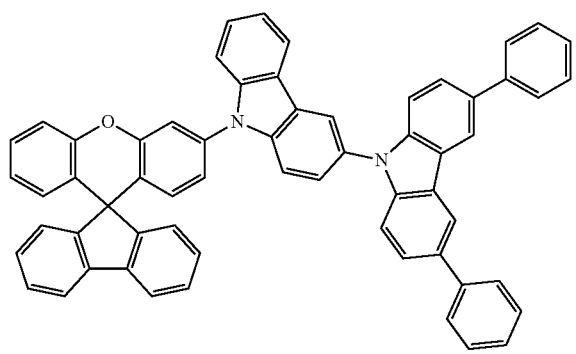
13
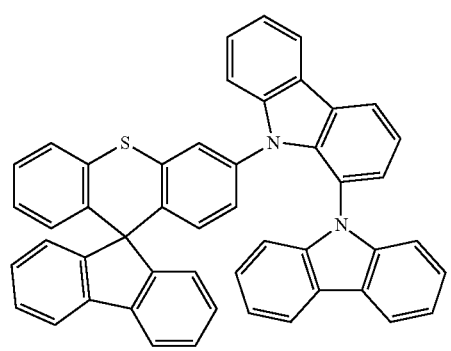
14
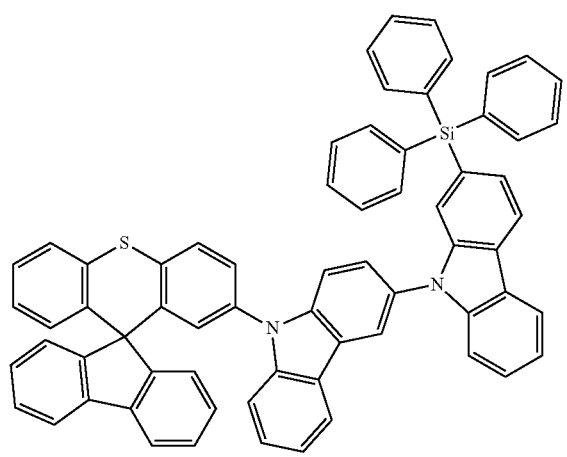

-continued
15
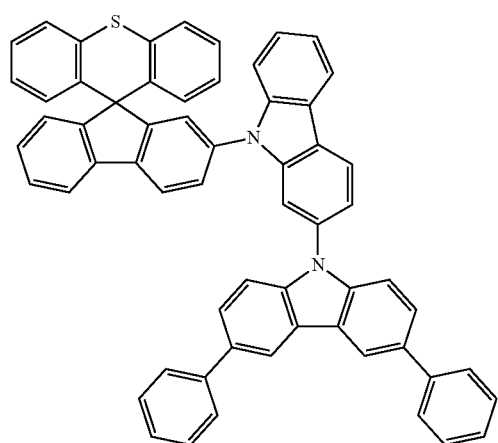
16
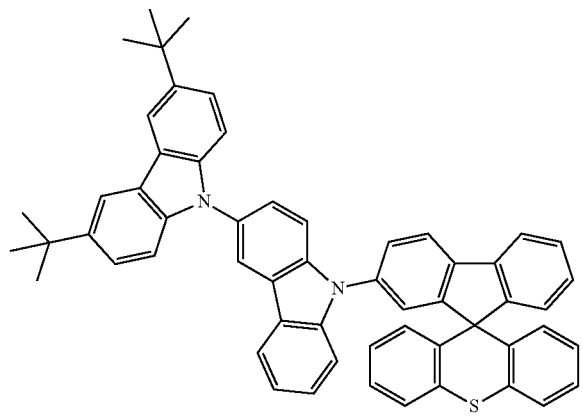
17
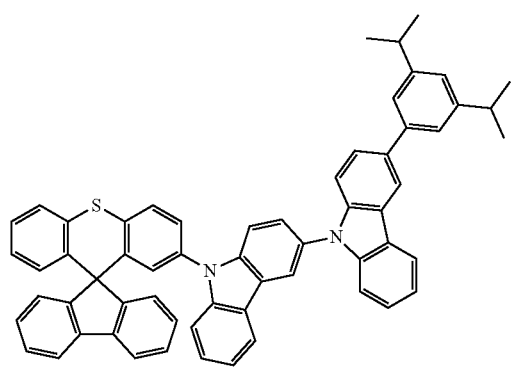
18
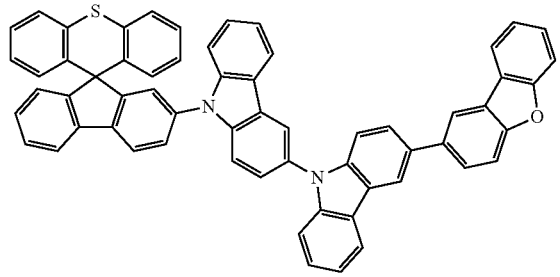
19
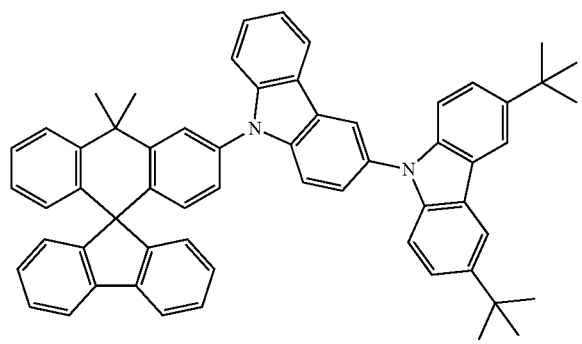
20
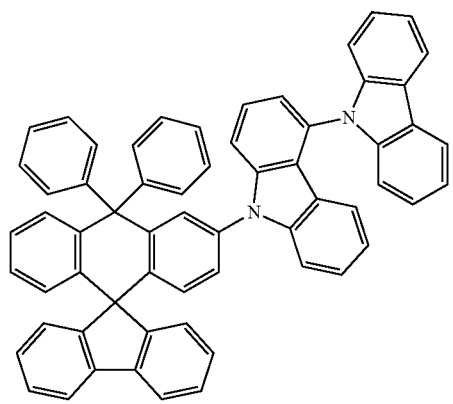

21
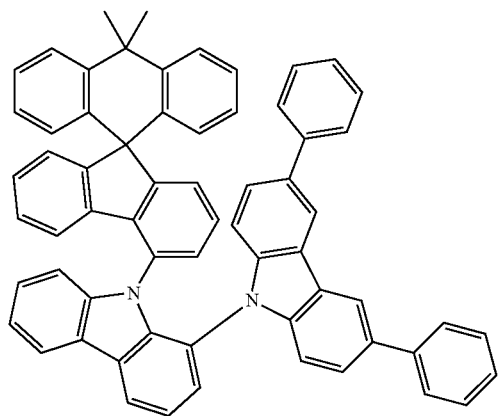
22
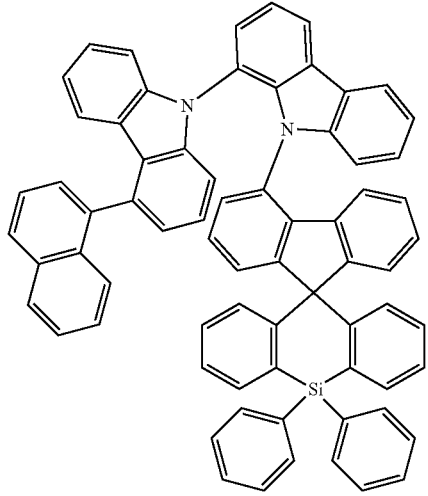
23
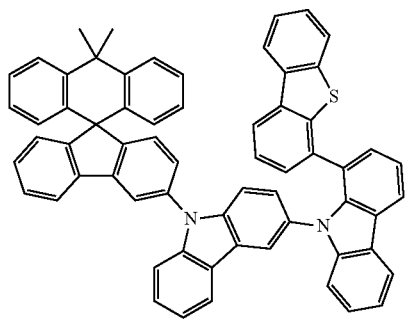
24
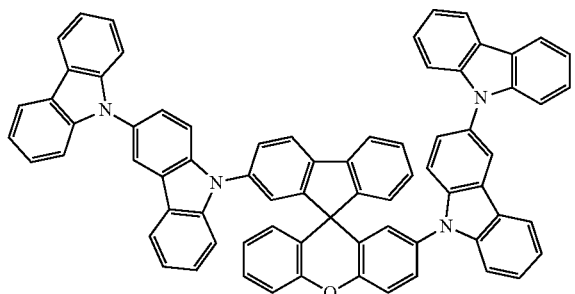
25
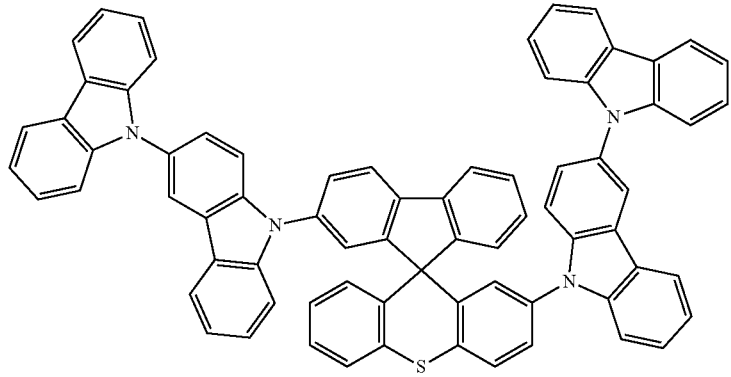
26
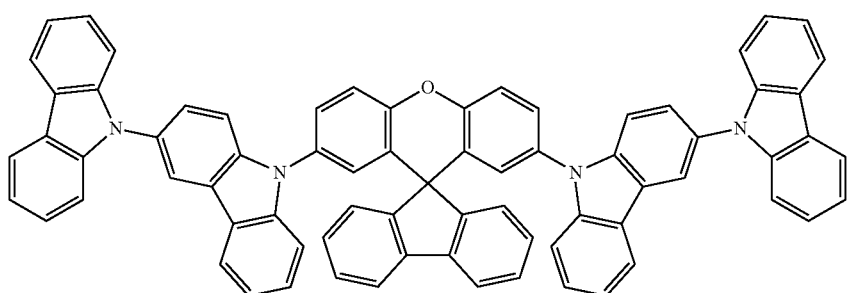

-continued
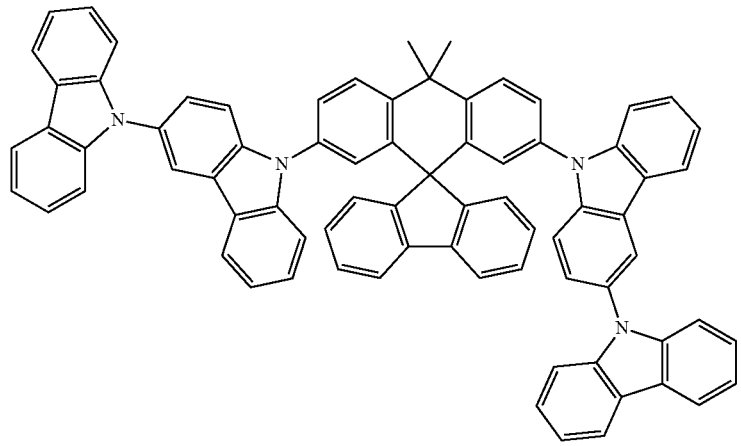
27
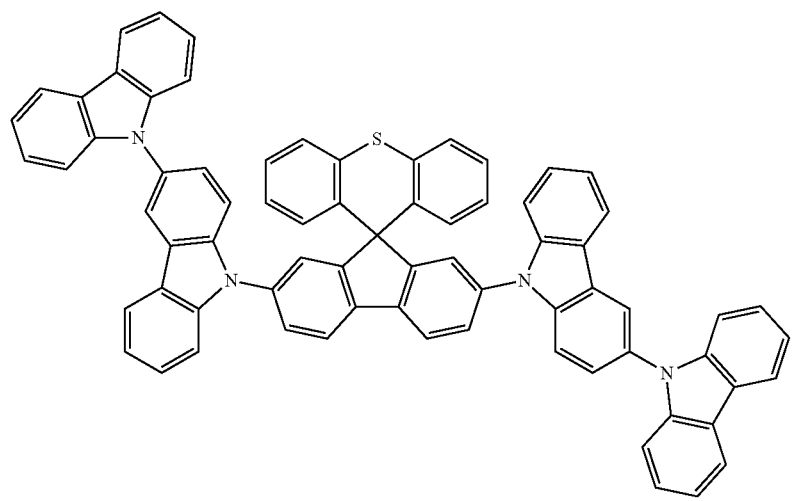
28
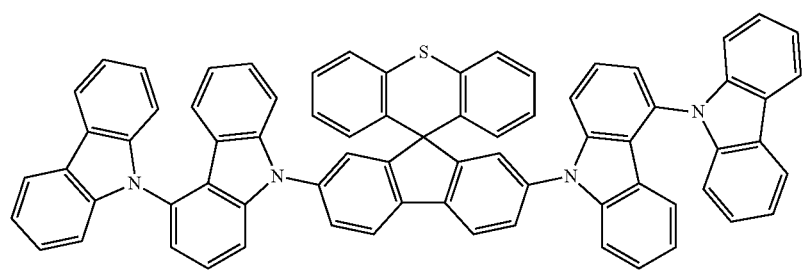
29
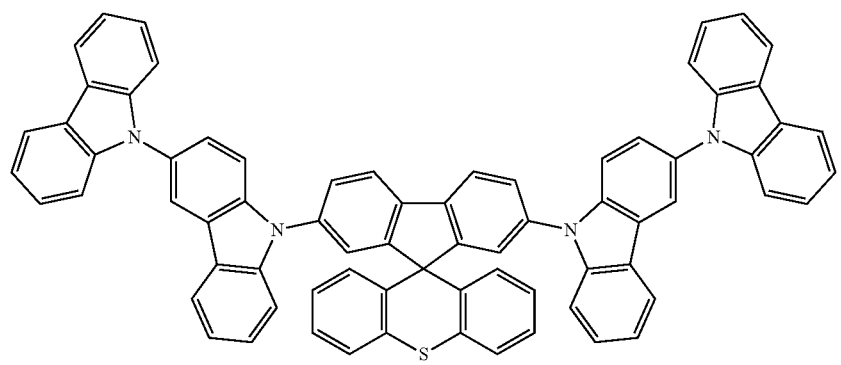
30

-continued
31
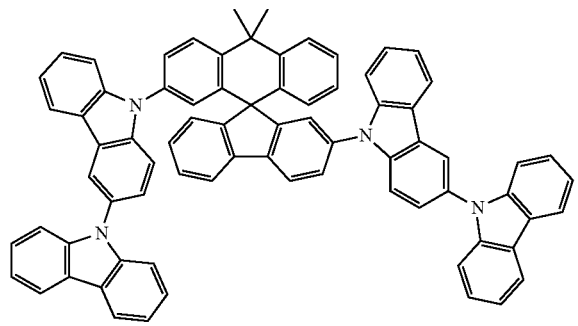
32
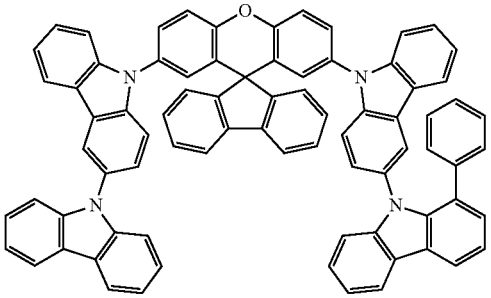
33
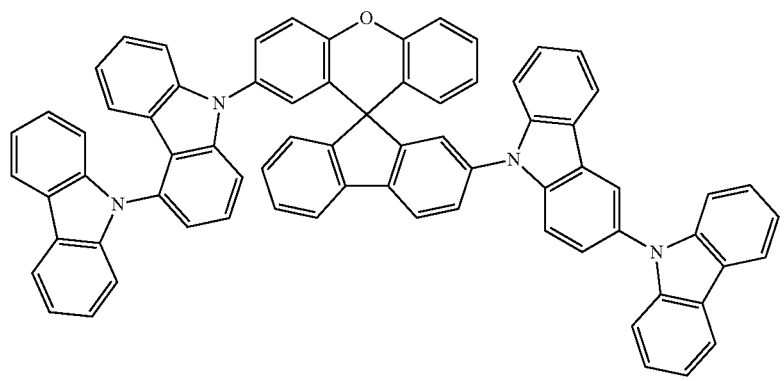
34
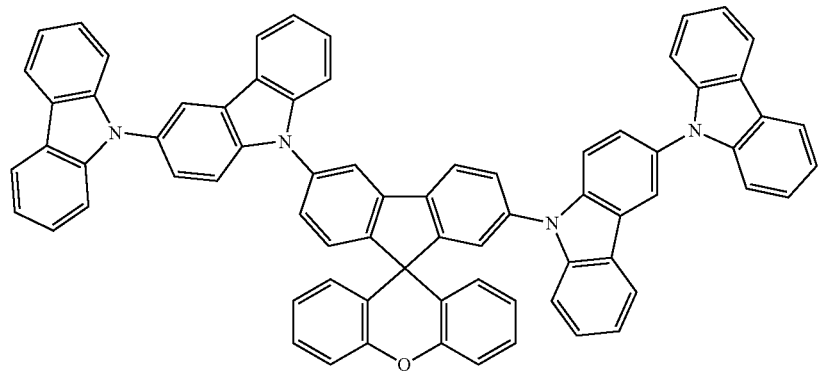
35
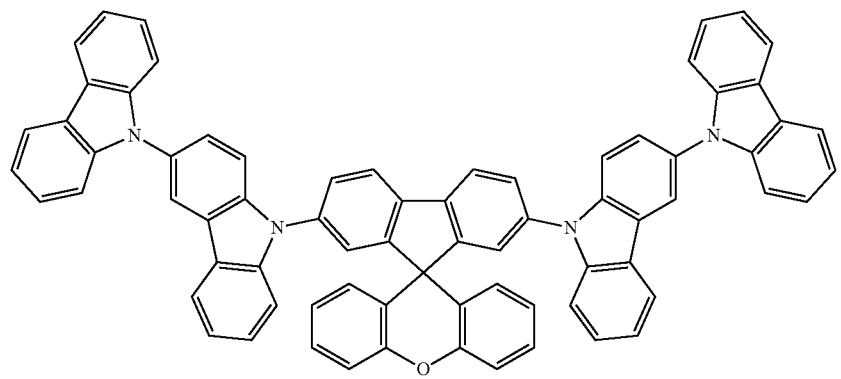

-continued
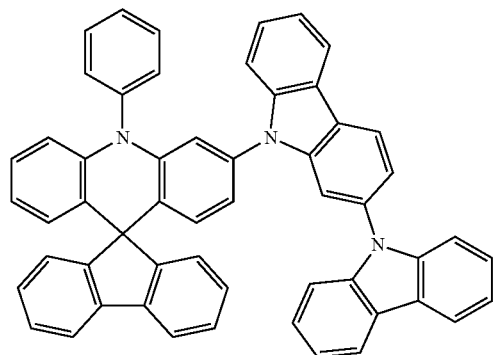
36
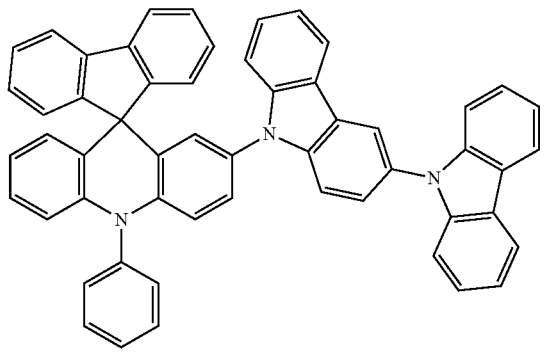
37
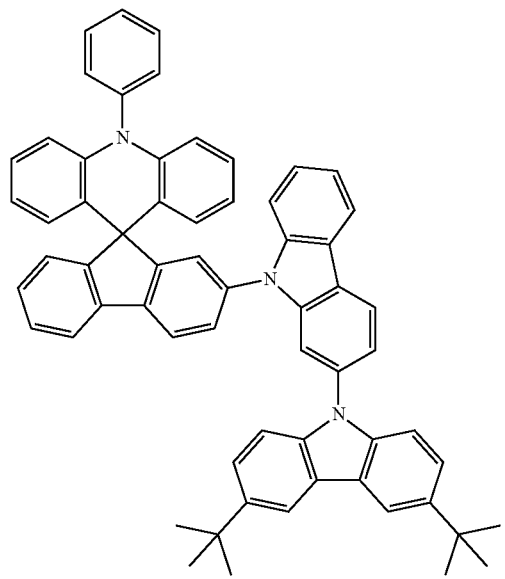
38
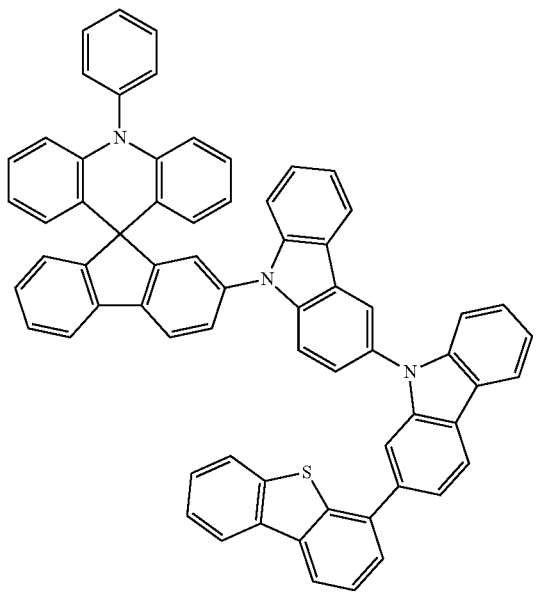
39
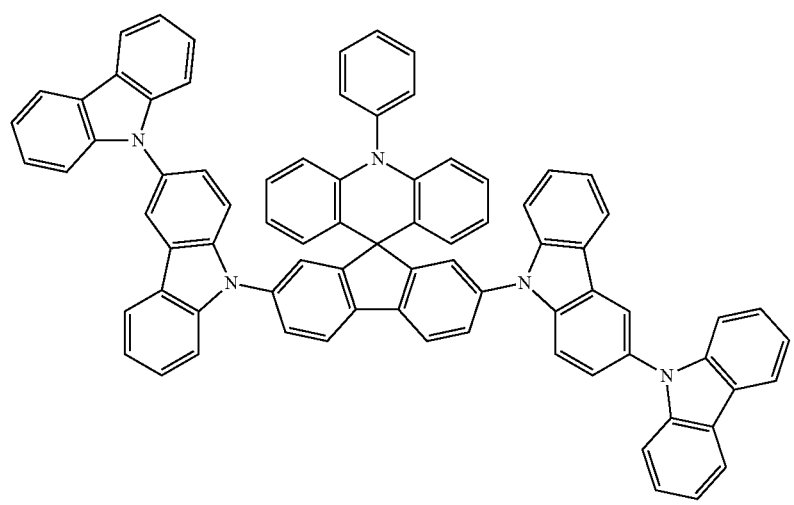
40

-continued
41
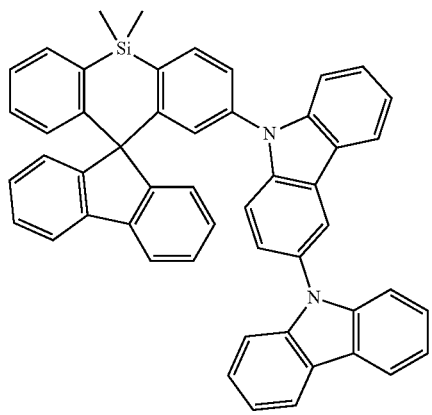
42
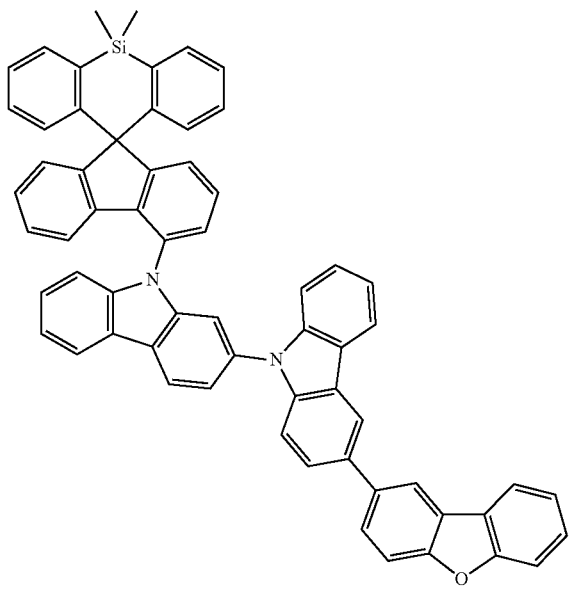
43
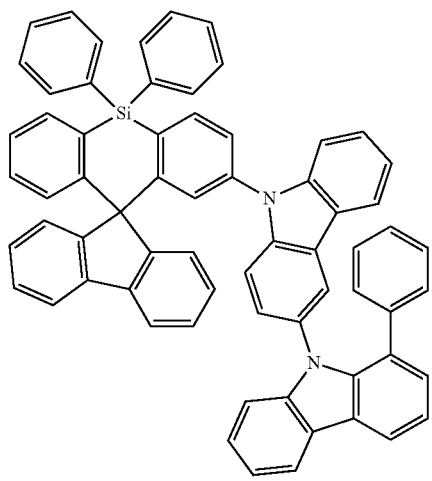
44
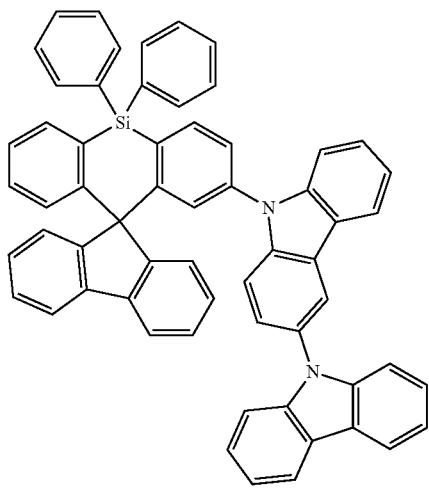
45
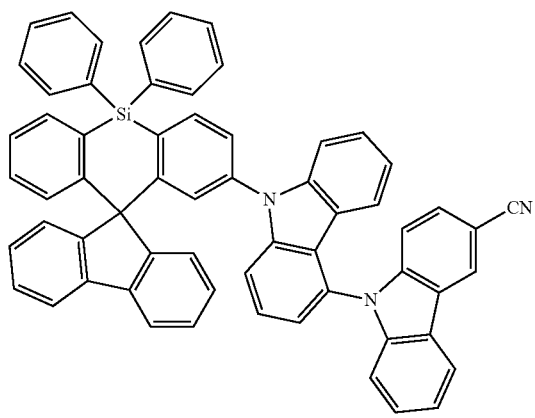
46
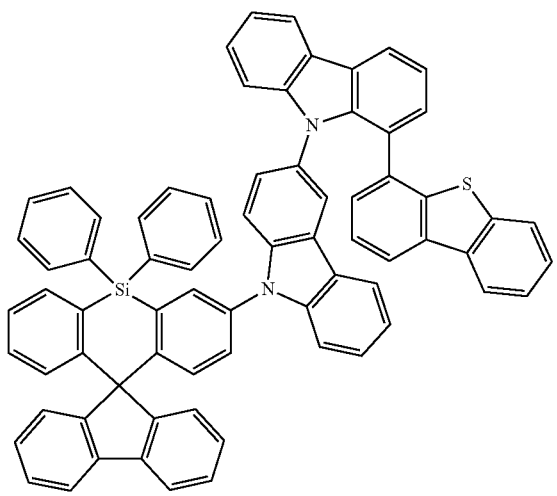

-continued
47
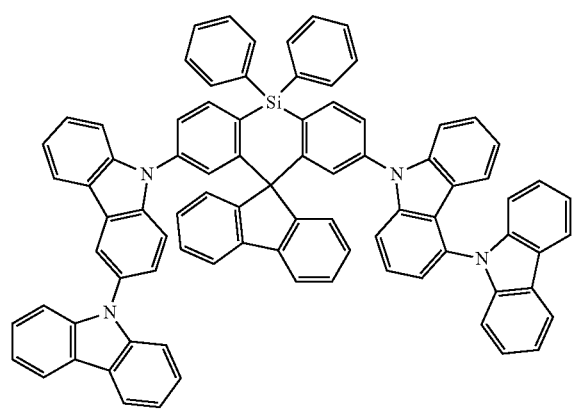
48
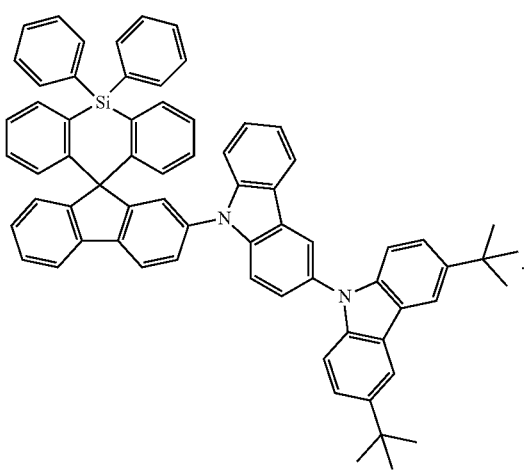
* * * * *